(12) United States Patent
Messersmith et al.

(10) Patent No.: US 8,841,408 B2
(45) Date of Patent: Sep. 23, 2014

(54) MACROMONOMERS AND HYDROGEL SYSTEMS USING NATIVE CHEMICAL LIGATION, AND THEIR METHODS OF PREPARATION

(75) Inventors: Phillip B Messersmith, Clarendon Hills, IL (US); Bi-Huang Hu, Chicago, IL (US); Jing Su, Chicago, IL (US)

(73) Assignee: Northwestern University, Evanston, IL (US)

( * ) Notice: Subject to any disclaimer, the term of this patent is extended or adjusted under 35 U.S.C. 154(b) by 585 days.

(21) Appl. No.: 12/106,429

(22) Filed: Apr. 21, 2008

(65) Prior Publication Data

US 2008/0274980 A1   Nov. 6, 2008

Related U.S. Application Data

(60) Provisional application No. 60/925,496, filed on Apr. 19, 2007.

(51) Int. Cl.
| | |
|---|---|
| *C08G 69/06* | (2006.01) |
| *C08G 69/40* | (2006.01) |
| *C08G 69/02* | (2006.01) |
| *C08G 69/04* | (2006.01) |
| *C08G 69/08* | (2006.01) |

(52) U.S. Cl.
CPC .............. *C08G 69/40* (2013.01); *C08G 69/02* (2013.01); *C08G 69/04* (2013.01); *C08G 69/08* (2013.01)
USPC ........... 528/350; 528/363; 528/364; 424/426; 424/486

(58) Field of Classification Search
None
See application file for complete search history.

(56) References Cited

PUBLICATIONS

Collagen from GenBank Accession No. BAA04483, pp. 1-3. Accessed Jul. 22, 2009.*
Albumin from *Mus musculus* from GenBank Accession No. CAC81903, pp. 1-2. Accessed Jul. 22, 2009.*
Human serum albumin from GenBank Accession No. CAA00606, pp. 1-3. Accessed Jul. 22, 2009.*
Malkoch M, Vestberg R, Gupta N, Mespouille L, Dubois P, Mason AF, Hedrick JL, Liao Q, Frank CW, Kingsbury K, Hawker CJ, "Synthesis of well-defined hydrogel networks using Click chemistry," Chem. Commun., 2006, 2774-2776.*
Akeson, et al., J. Biol. Chem., 1996, 271, 30517.
Weber, et al., Biomaterials 2007, 28 (19), 3004-3011.
Arnush, et al., J. Clin. Invest. 1998, 102(3), 516.
Barshes, et al., J. Leuk. Bio. 2005, 77, 587.
Bang, et al., Angew. Chem. Int. Edit. 2006, 45, 3985-3988.
Beck, et al., Nguyen Tissue Eng. 2007, 13, 589.
Bernkop-Schnurch, et al., J. Control. Release 2003, 93, 95-103.
Collier, et al., J. Am. Chem. Soc. 2001, 123, 9463-9464.
Cushing, et al., Science 2007, 316, 1133-1134.
Dawson, et al., Science 1994, 266, 776-779.
Dawson, et al., Annu. Rev. Biochem. 2000, 69, 923-960.
De Groot, et al., J. Surg. Res., 2004, 121,141-240.
DeVos, et al., Biomaterials, 1997, 18, 273.
Hennink, et al., Adv. Drug Deliv. Rev. 2002, 54, 13-36.
Hoffman, Adv. Drug Deliv. Rev. 2002, 54, 3-12.
Jackson, Nat. Med. 1996; 2, 637-638.
Jackson, Am. J. Surg. 2001, 182, 1S-7S.
Jakubowski, Nucleic Acids Res. 1995, 23, 4608-4615.
Jeong, et al., Nature 1997, 388, 860-862.
Johnson, et al., J. Am. Chem. Soc. 2006, 128, 6640-6646.
Kavanagh, et al., Prog. Polym. Sci. 1998, 23, 533-562.
Kemp, Biopolymers 1981, 20, 1793-1804.
Kumar, et al., Adv. Polym. Sci. 2002, 160, 45-117.
Lee, et al., Chem. Rev. 2001, 101, 1869-1879.
Luo, et al., Proc Natl Acad Sci U S A. 2007, 104: 2821-2826.
Macmillan, Angew. Chem. Int. Edit. 2006, 45, 7668-7672.
Morikawa, Am. J. Surg. 2001, 182, 29S-35S.
Wieland, et al., Ann. Chem. 1953, 583, 129-149.
O'Shea, Sun Diabetes, 1986, 35, 943.
Wieland, Chimia 1974, 28, 496-499.
Peppas, et al., Adv. Mater. 2006, 18, 1345-1360.
Rabinovitch, et al., Biochem. Pharmacol, 1998, 55, 1139.
Ross-Murphy, Polymer Gels and Networks 1994, 2, 229-237.
Spotnitz, Am. J. Surg. 2001, 182, 8S-14S.
Sanborn, et al., Biomaterials 2002, 23, 2703-2710.
Sawhney, et al., Macromolecules 1993, 26, 581-587.
Stetsenko, et al., J.Org. Chem. 2000, 65, 4900-4908.
Tam, et al., Biopolymers 2000, 51, 311-332.
Teramura et al., Biomaterials, 2007, 28, 4818.
VanSchilfgaarde, et al., J. Mol. Med., 1999, 77, 199-205.
Wang, Nat. Biotech. 1997, 15, 358-362.
Wathier, et al., J. Am. Chem. Soc. 2004, 126, 12744-12745.
Weber, et al., J. Mol. Evol. 1979, 13, 193-202.
Wiegand, et al., Transplantation, 1993, 56, 1206.

* cited by examiner

*Primary Examiner* — James H Alstrum Acevedo
*Assistant Examiner* — Fred Reynolds
(74) *Attorney, Agent, or Firm* — Quarles & Brady, LLP

(57) ABSTRACT

Biocompatible macromonomers, hydrogels, methods of synthesis and methods of use thereof are provided. The biocompatible hydrogels of the present invention are prepared using native chemical ligation (NCL), in which a thioester readily reacts with a N-terminal thiol (cysteine) through transesterification and rearrangement to form an amide bond through a five-member ring intermediate.

11 Claims, 15 Drawing Sheets

Formula I

Formula II

Formula III

A. Control gel
B. 1% GRGDSPG on gel
C. 1% GRGDSPG + 1% IL-1RIP on gel

SEQUENCE LISTING

<160> NUMBER OF SEQ ID NOS: 2

<210> SEQ ID NO 1
<211> LENGTH: 7
<212> TYPE: PRT
<213> ORGANISM: ARTIFICIAL

```
<220> FEATURE:
<223> OTHER INFORMATION: SYNTHETIC PEPTIDE

<400> SEQUENCE: 1

Gly Arg Gly Asp Ser Pro Gly
1               5

<210> SEQ ID NO 2
<211> LENGTH: 11
<212> TYPE: PRT
<213> ORGANISM: ARTIFICIAL
<220> FEATURE:
<223> OTHER INFORMATION: SYNTHETIC PEPTIDE

<400> SEQUENCE: 2

Phe Glu Trp Thr Pro Gly Trp Tyr Gln Pro Tyr
1               5                   10
```

US 8,841,408 B2

MACROMONOMERS AND HYDROGEL SYSTEMS USING NATIVE CHEMICAL LIGATION, AND THEIR METHODS OF PREPARATION

CROSS-REFERENCE TO RELATED APPLICATIONS

This application claims priority to U.S. Provisional Application No. 60/925,496, filed Apr. 19, 2007, the entirety of which is hereby incorporated by reference for all purposes.

STATEMENT REGARDING FEDERALLY-SPONSORED RESEARCH

This invention was made in part with government support under grant numbers DE013030 and EB003806 awarded by the National Institutes of Health. The government has certain rights in this invention.

FIELD OF THE INVENTION

This invention is directed to new biocompatible hydrogels, specifically covalently cross-linked polymer hydrogels, as well as methods of synthesis and use of the new hydrogels.

BACKGROUND OF THE INVENTION

Hydrogels are hydrophilic polymeric networks which can absorb and retain large amounts of water (Hoffman, 2002; Peppas, 1987; Peppas, 2006; Okano, 1998). Hydrogels are useful in controlled release systems for drug delivery (Kumar, 2002), tissue repair, tissue engineering (Cushing, 2007; Lee, 2001) and as surgical sealants and adhesives (Jackson, 1996; Spotnitz, 2001). Although great progress in medical applications of hydrogels has been made, it remains challenging to develop cross-linking methods that satisfy the demanding biological and handling requirements for medical treatment (Hennink, 2002). Accordingly, there is a long-felt, unmet need for biocompatible hydrogels capable of deployment by minimally invasive methods and solidification under physiological conditions.

Native chemical ligation (NCL) is a widely used technique for constructing a large polypeptide from two or more unprotected peptides. In NCL, a peptide containing a C-terminal thioester reacts with another peptide containing an N-terminal cysteine in the presence of an added thiol catalyst. In a freely reversible first step, a transthioesterification occurs to yield a thioester-linked intermediate; this intermediate rearranges irreversibly under the usual reaction conditions to form a native amide bond at the ligation site. Thioesters, for example, have proven useful in the chemical synthesis of large peptides and proteins using NCL (Dawson, 1994; Tam, 2000; Dawson, 2000; Macmillan, 2006; Paramonov, 2005). In nature, thioesters participate in the synthesis of a number of cellular components, and can be prepared as activated building blocks through chemical synthesis (Tam, 2000; Jakubowski, 1995; Kemp, 1981). Although relatively unreactive to aminolysis, thioesters readily react with a thiol group through transesterification to form a new thioester (Weber, 1979; Wieland, 1974; Wieland, 1953). The reaction between a thioester and an N-terminal-Cys yields an S-acyl covalent intermediate that spontaneously undergoes an S- to N-acyl migration to form an amide bond through a five-member ring intermediate (FIG. 15).

However, NCL has not been shown to successfully form hydrogels from soluble macromolecular precursors. NCL offers several advantages as a potential hydrogel cross-linking method, including chemoselectivity and high efficiency under physiological conditions without involving catalysts, initiators or other potentially toxic compounds. Further, NCL provides synthetic access to large peptides and proteins otherwise impossible to make, due to length or decoration by posttranslational modification. Further still, NCL cross-linking increases the stiffness of pre-assembled peptide hydrogels (Jung, 2008).

Accordingly, there is a long-felt, unmet need for biocompatible hydrogels and methods of synthesis and use thereof, where the hydrogels are synthesized using NCL.

SUMMARY OF THE INVENTION

The present invention provides novel biocompatible macromonomers, hydrogels, methods of synthesis using native chemical ligation and methods of use thereof.

In a first embodiment, the invention provides a biocompatible macromonomer according to the following structure:

(Formula I)

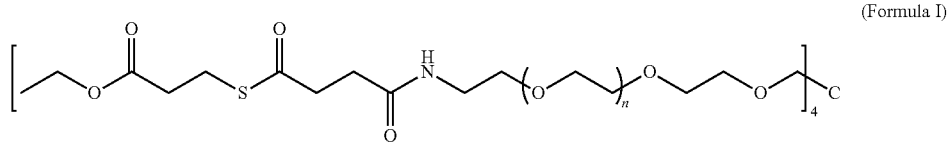

wherein each "n" has a value in the range of 0 to 200.

In a second embodiment, the invention provides a biocompatible macromonomer according to the following structure:

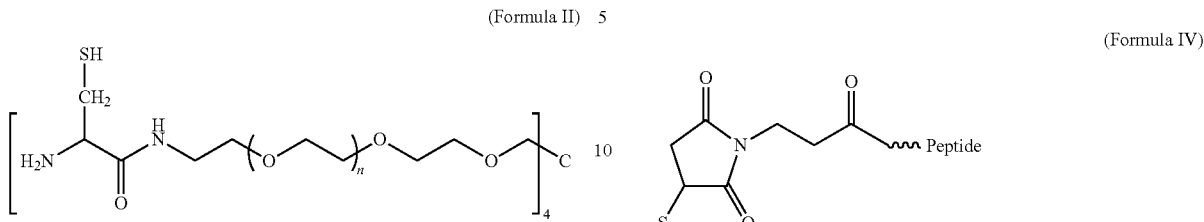

(Formula II)

wherein each "n" has a value in the range of 0 to 200.

In a third embodiment, the invention provides a biocompatible macromonomer according to the following structure:

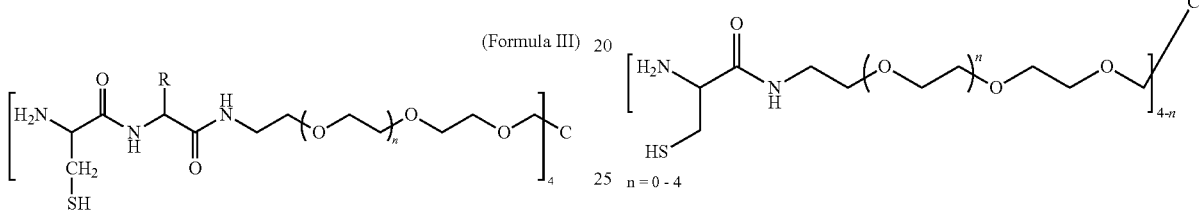

(Formula III)

wherein each "n" has a value in the range of 0 to 200 and wherein "R" is selected from the group consisting of H, $CH_2CH_2COOH$, $CH_2COOH$,

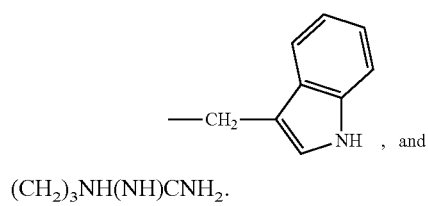, and $(CH_2)_3NH(NH)CNH_2$.

In a fourth embodiment, the invention provides a biocompatible macromonomer according to the following structure:

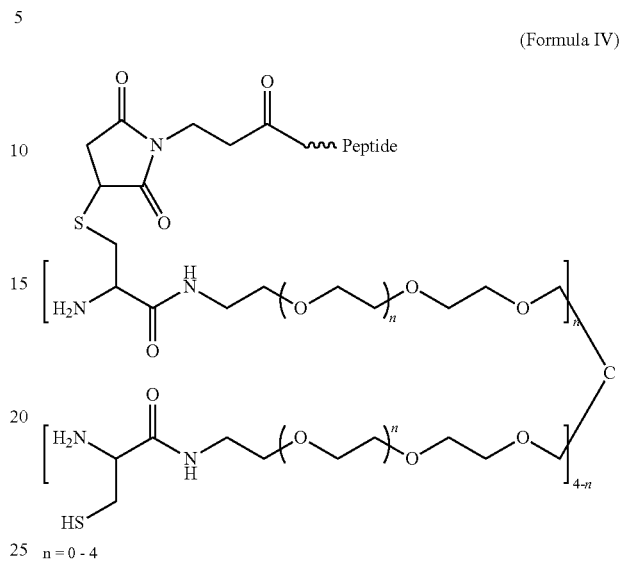

(Formula IV)

n = 0 - 4 wherein each "n" has a value in the range of 0 to 200 and wherein the peptide is selected from the group consisting of GRGDSPG-$NH_2$ (SEQ ID NO: 1) or OEG2-FEWTPGW-YQPY-$NH_2$ (SEQ ID NO: 2).

In an alternative embodiment the present invention provides novel, biocompatible hydrogels. In a first embodiment the hydrogel has the following structure:

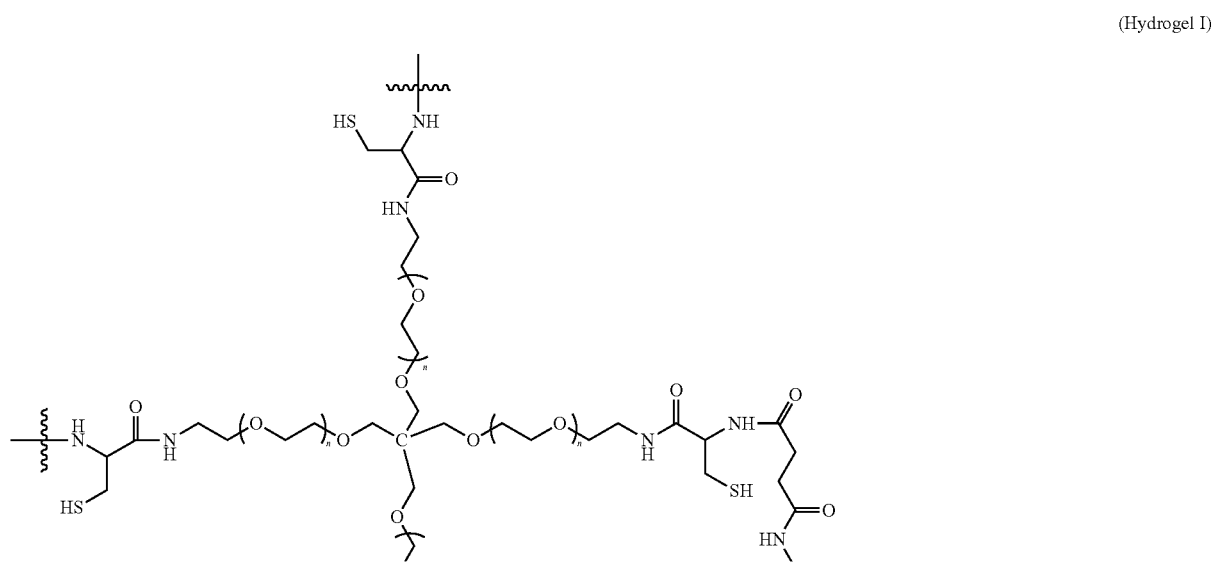

(Hydrogel I)

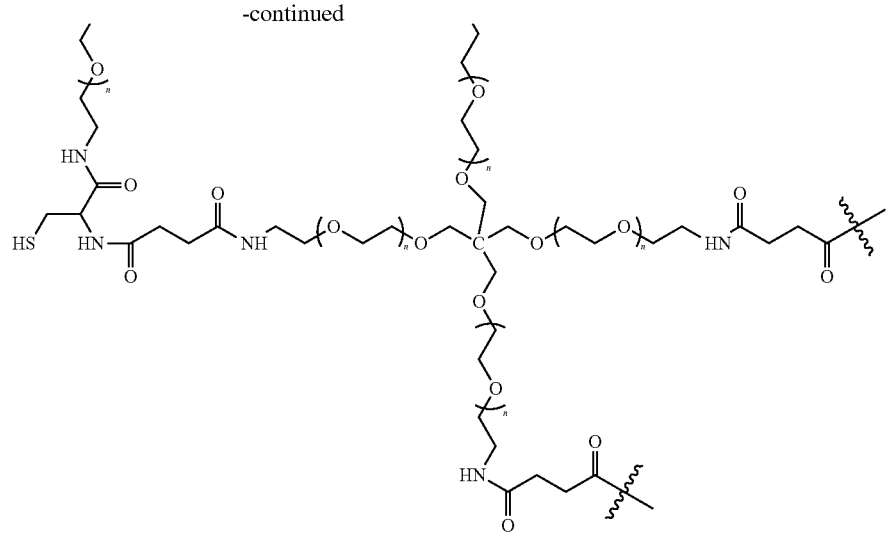
wherein each "n" has a value in the range of 0 to 200.
In a second embodiment, the hydrogel has the following structure:
(Hydrogel II)
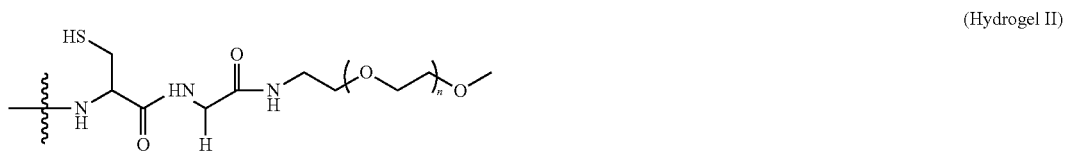
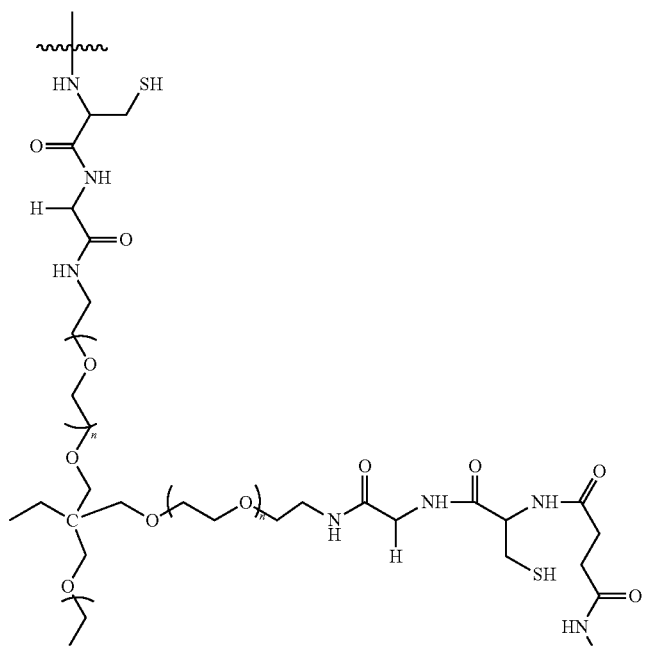

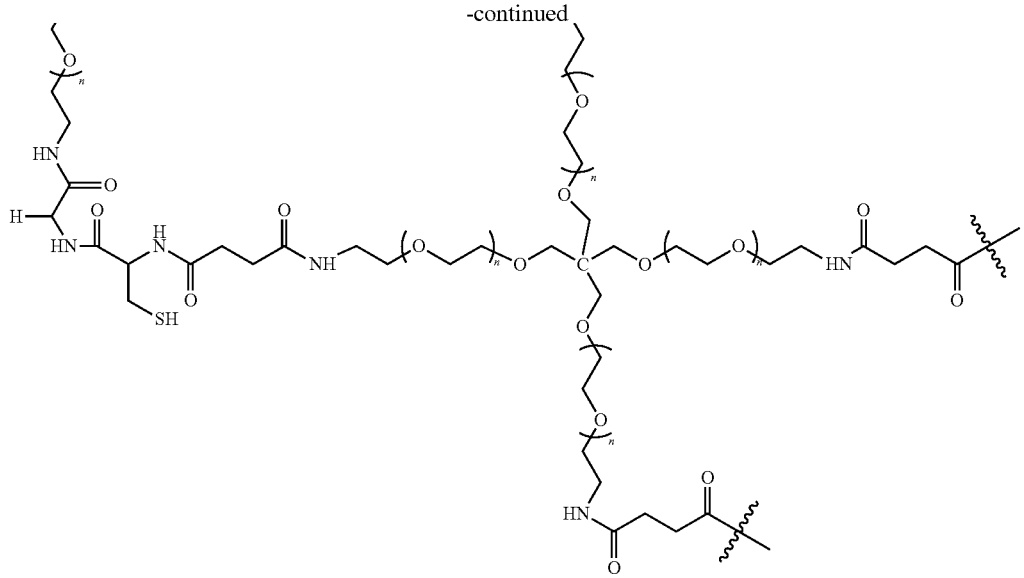
wherein each "n" has a value in the range of 0 to 200.
In a third embodiment, the hydrogel has the following structure:
(Hydrogel III)
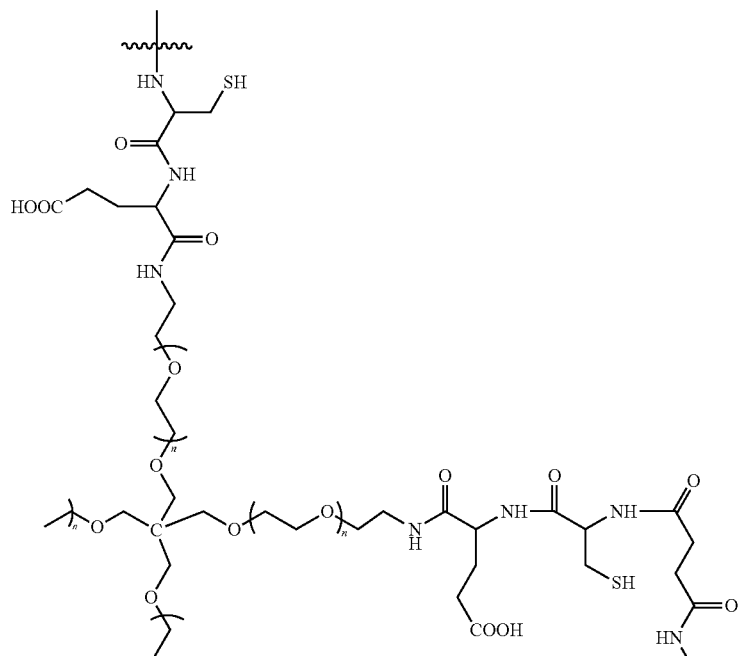

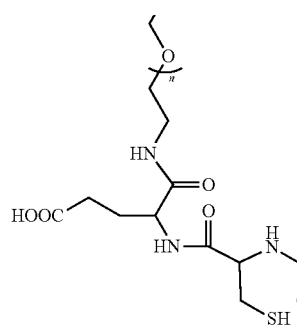
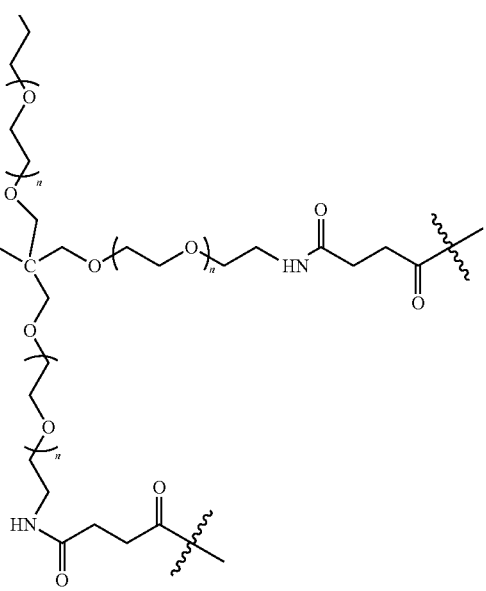
wherein each "n" has a value in the range of 0 to 200.
In a fourth embodiment, the hydrogel has the following structure:
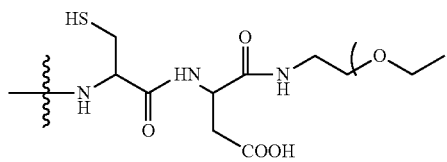
(Hydrogel IV)
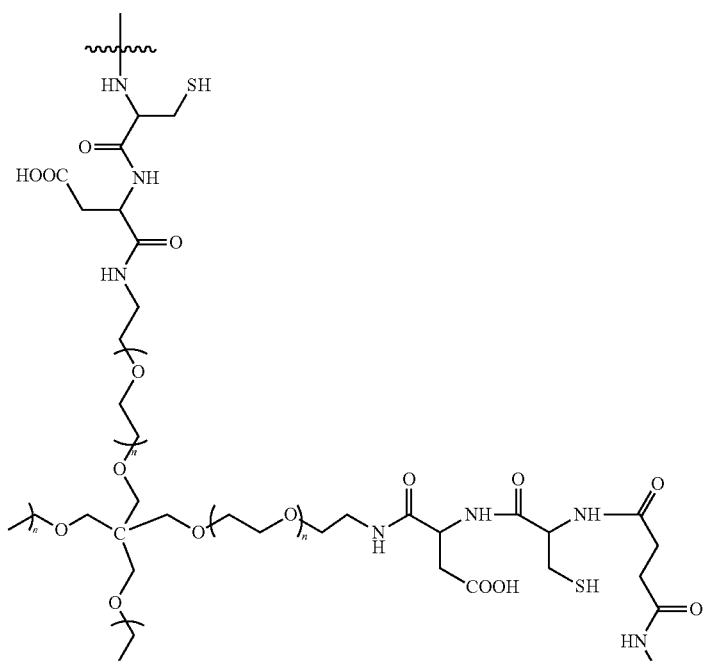

-continued
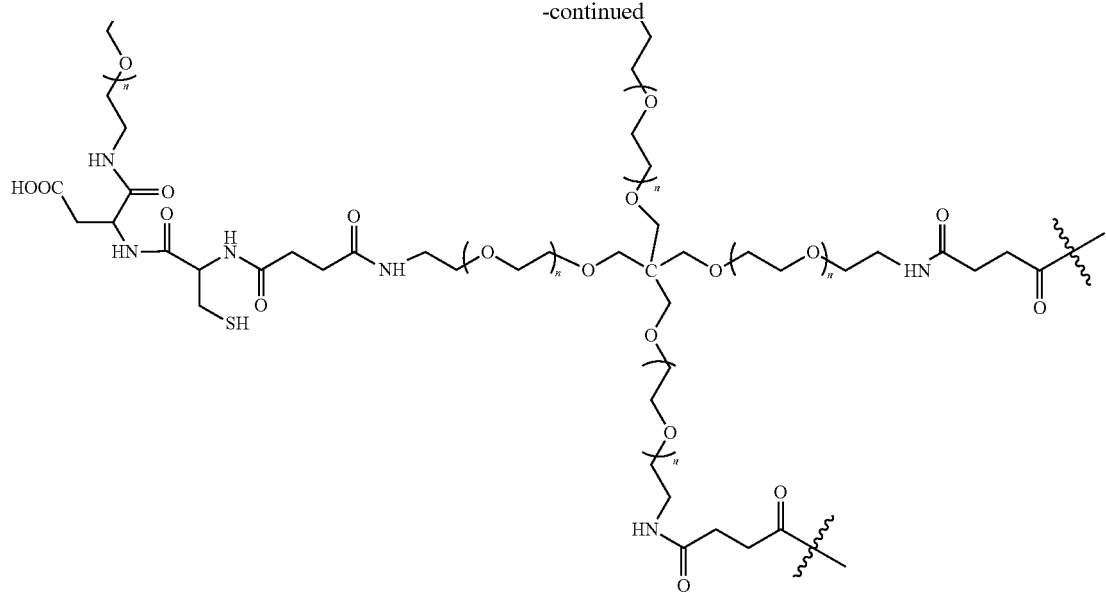
(25)
wherein each "n" has a value in the range of 0 to 200.
In a fifth embodiment, the hydrogel has the following structure:
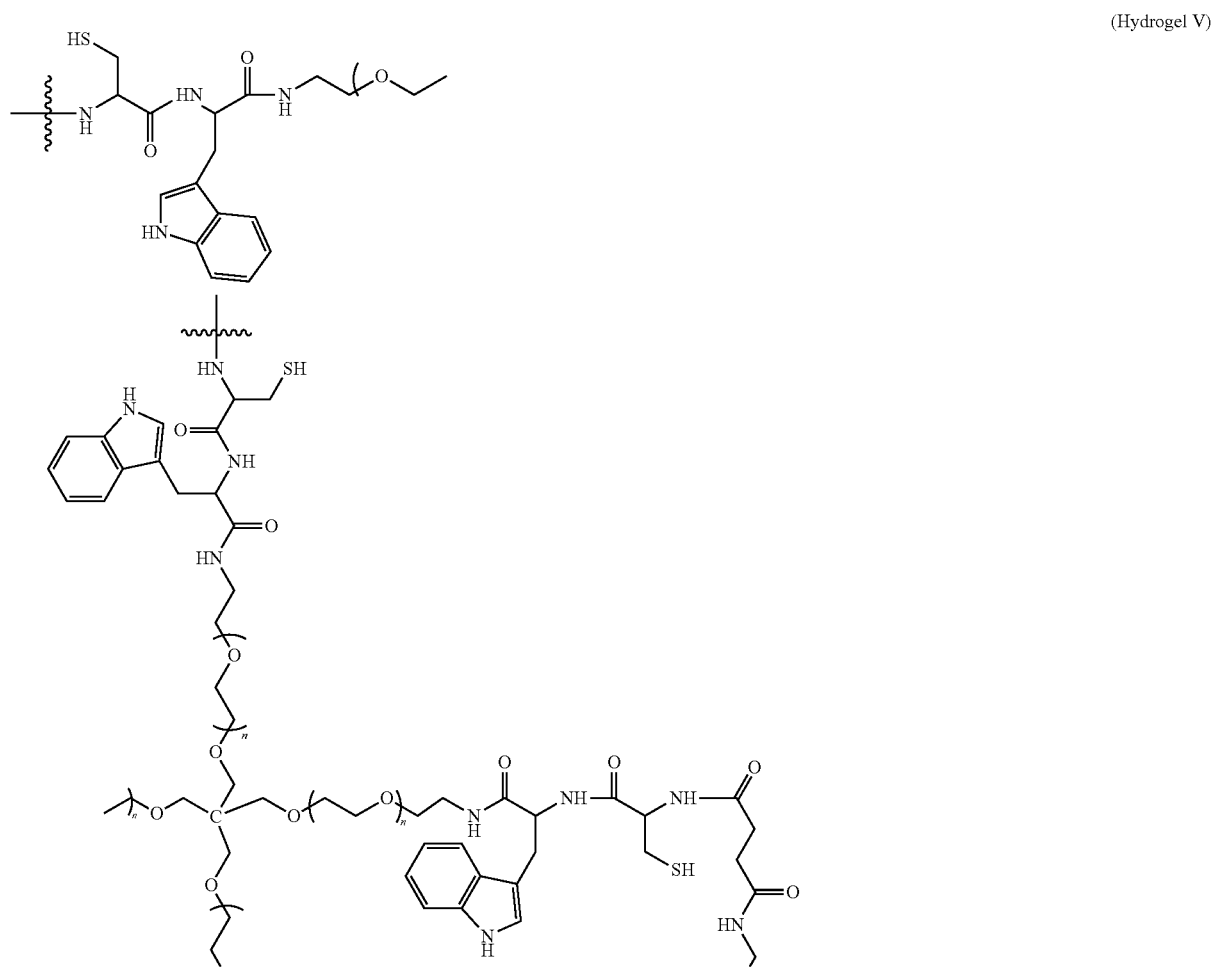
(Hydrogel V)

-continued
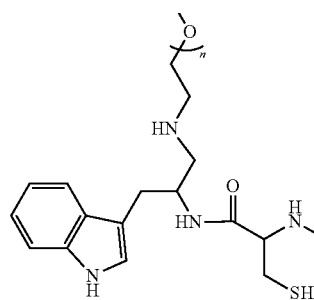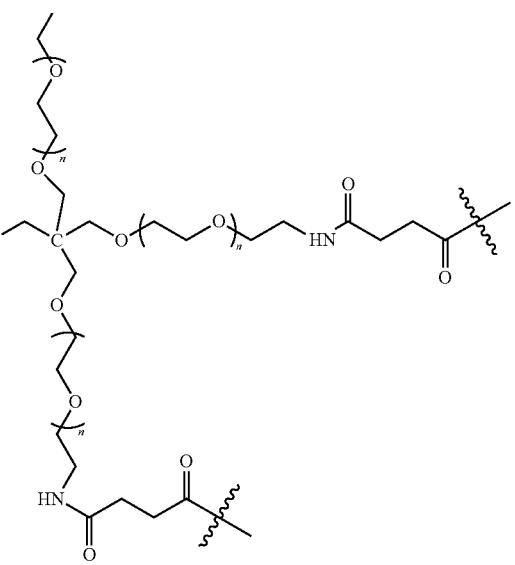
wherein each "n" has a value in the range of 0 to 200.
In a sixth embodiment, the hydrogel has the following structure:
(Hydrogel VI)
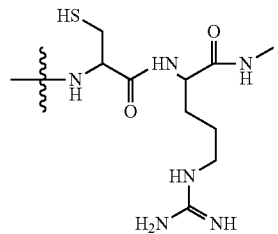
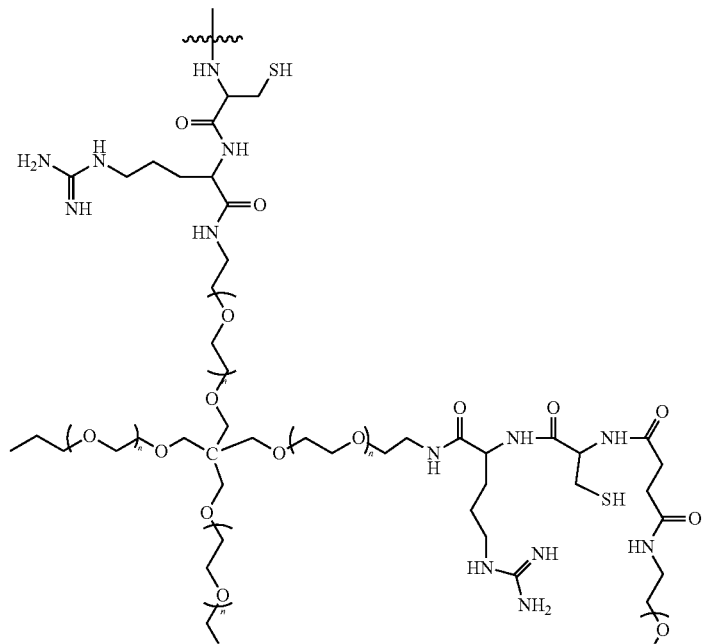

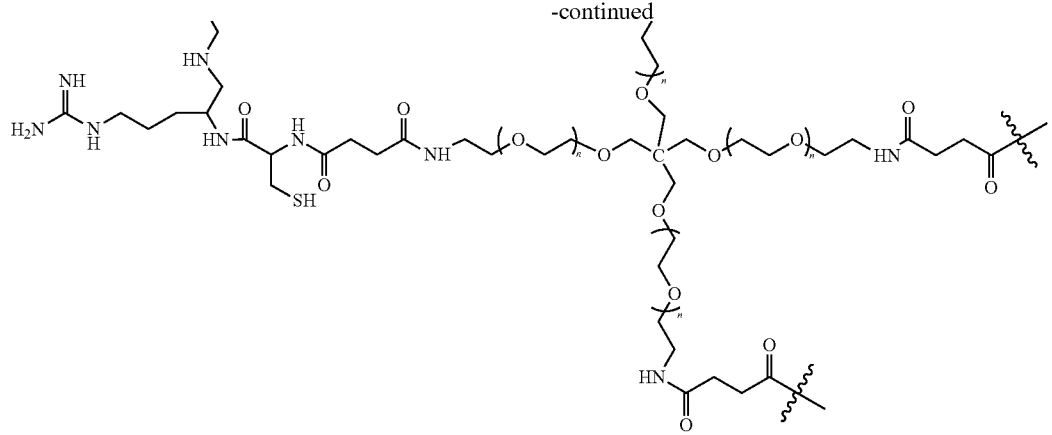
wherein each "n" has a value in the range of 0 to 200.
In an alternate embodiment, the hydrogel has the following structure:
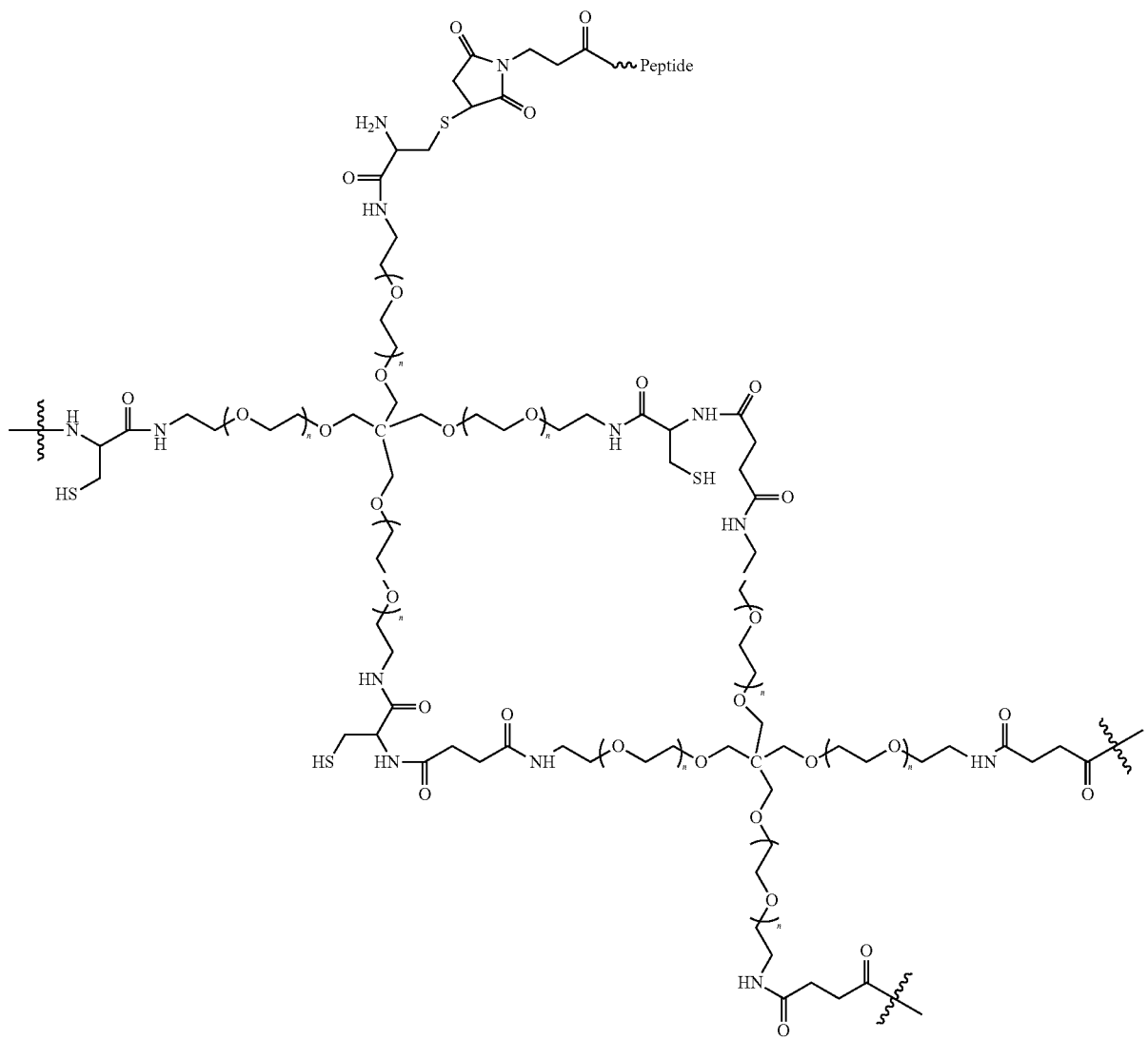
(Hydrogel VII)

wherein each "n" has a value in the range of 0 to 200 and wherein the peptide is a maleimide-terminated peptide.

The present invention also provides methods of synthesis for the above-discussed macromonomers and hydrogels. In a first embodiment, a method of synthesizing a novel, biocompatible hydrogel having the following structure is provided:

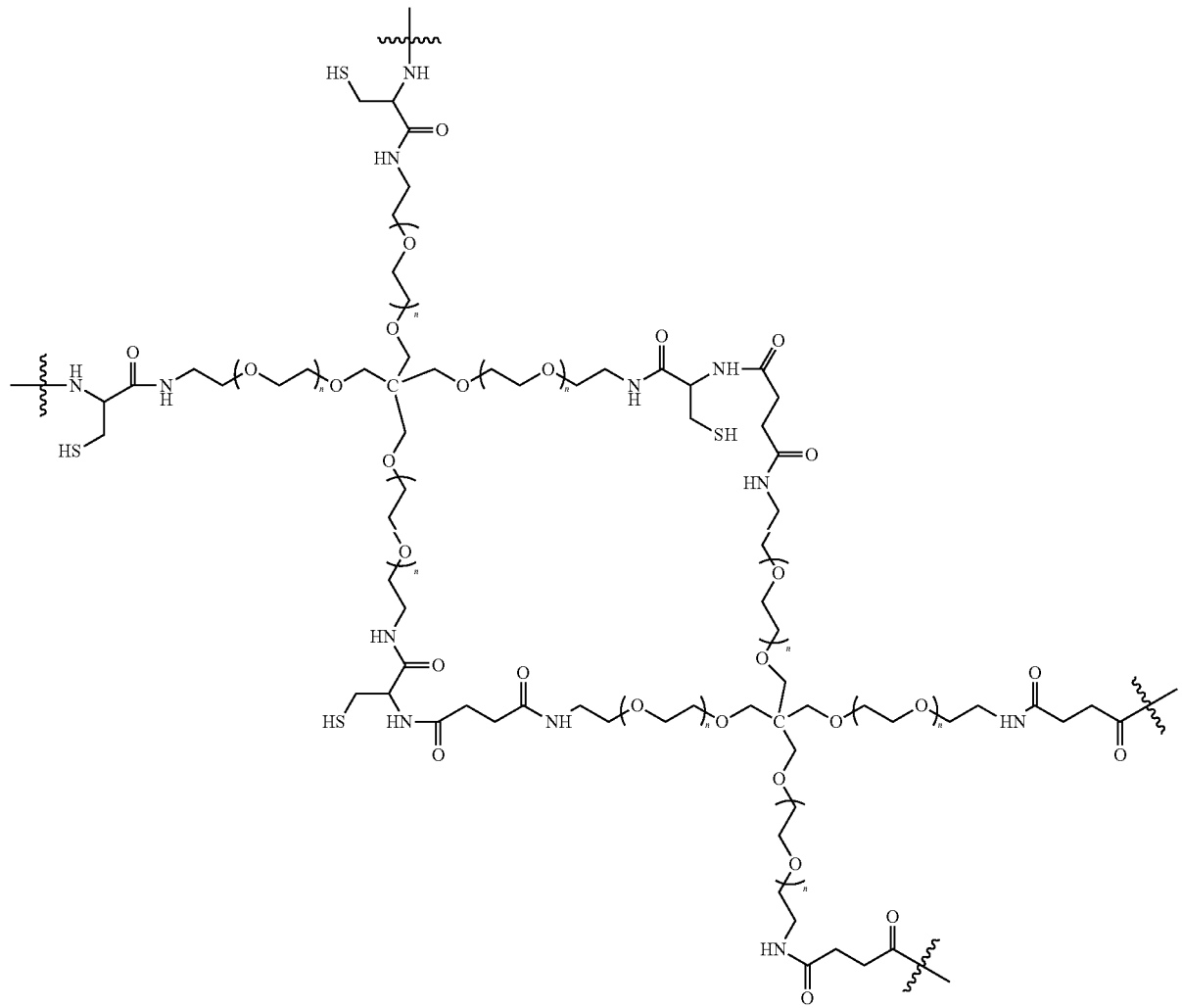

(Hydrogel I)

the method comprising the steps of covalently crosslinking an effective amount of a first macromonomer with an effective amount of a second macromonomer, wherein a hydrogel is formed. In a preferred embodiment, the first macromonomer is a macromonomer according to Formula I and the second macromonomer is a macromonomer according to Formula II. Preferably, equivalent amounts of macromonomers are used, and the macromonomers are covalently crosslinked using native chemical ligation.

In an alternative preferred embodiment, the invention provides a method of synthesizing a biocompatible hydrogel comprising covalently crosslinking through native chemical ligation an effective amount of a first macromonomer having a structure according to Formula I with an effective amount of a second macromonomer selected from the group consisting of Formula III, wherein a biocompatible hydrogel is formed.

For instance, where the second macromonomer has a structure according to Formula III:

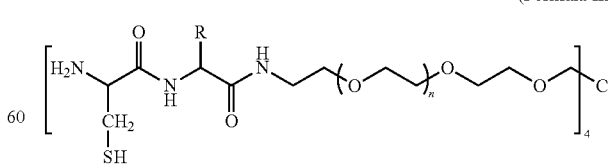

(Formula III)

wherein "R" is hydrogen, a hydrogel according to the following structure is formed:

(Hydrogel II)
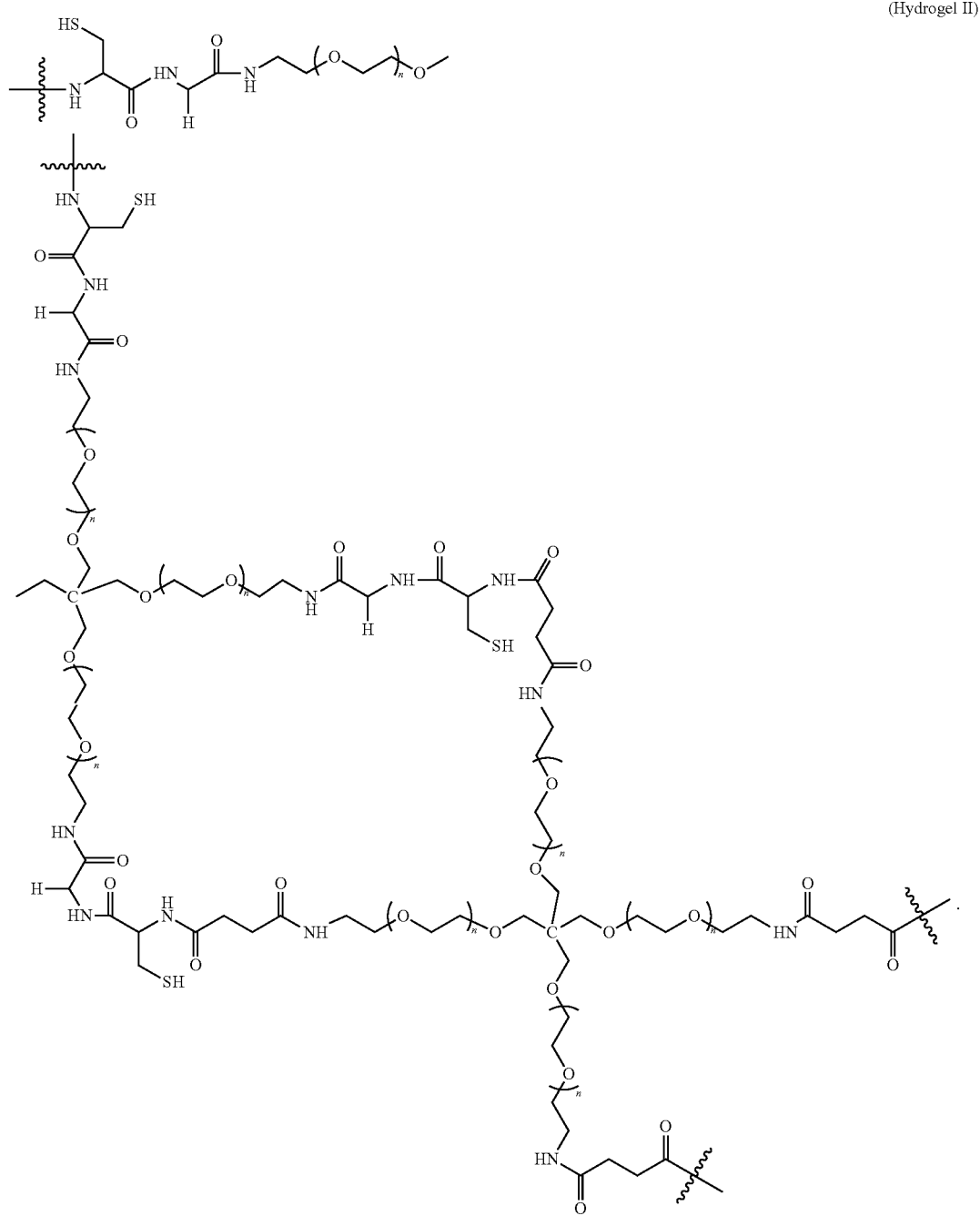
When "R" is CH₂CH₂COOH, a hydrogel according to the following structure is formed:
(Hydrogel III)
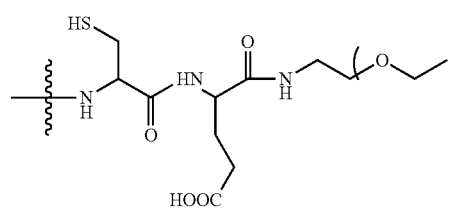

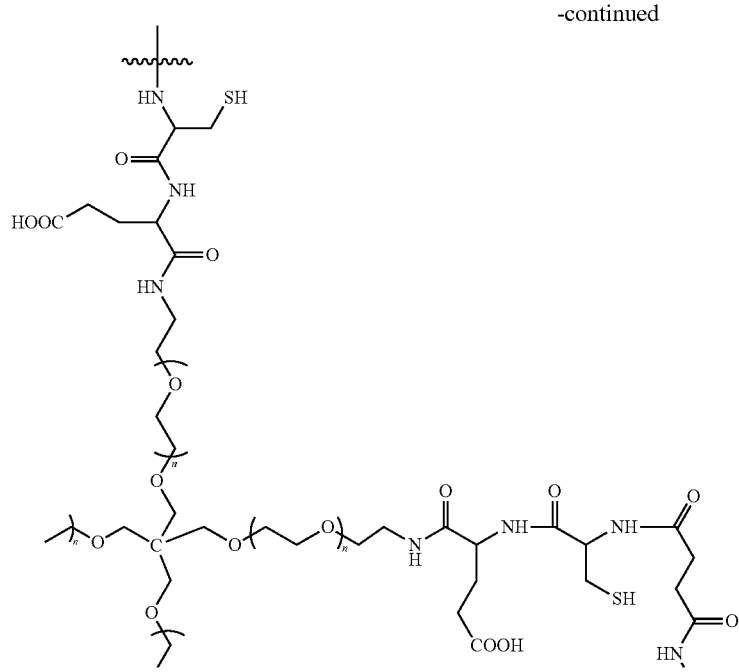
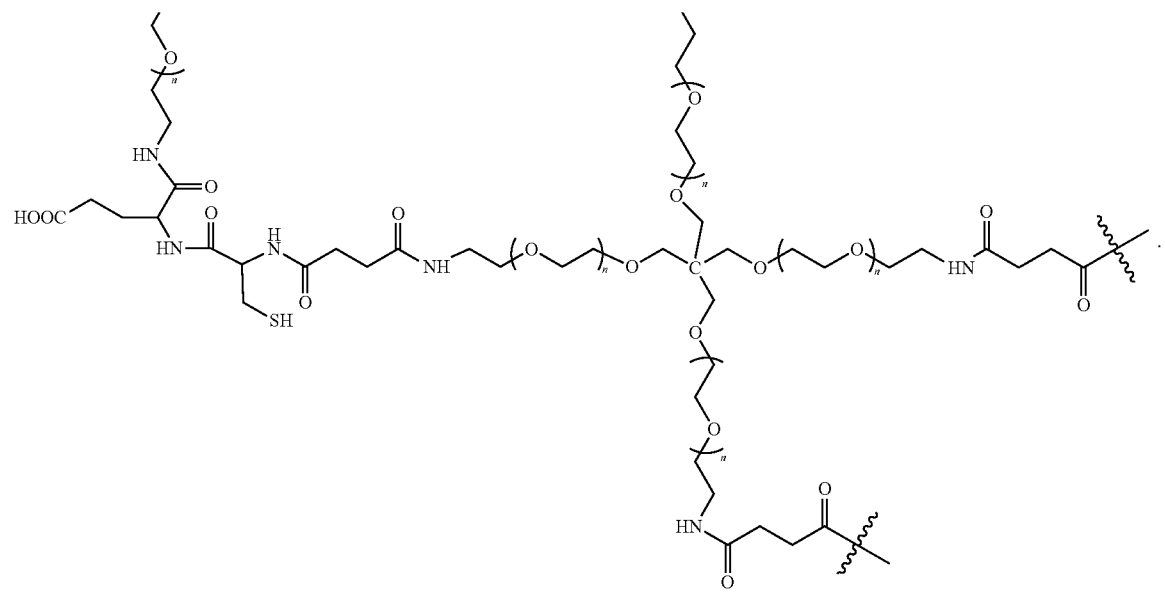
When "R" is CH$_2$COOH, a hydrogel according to the following structure is formed:
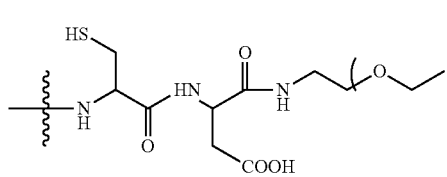
(Hydrogel IV)

-continued
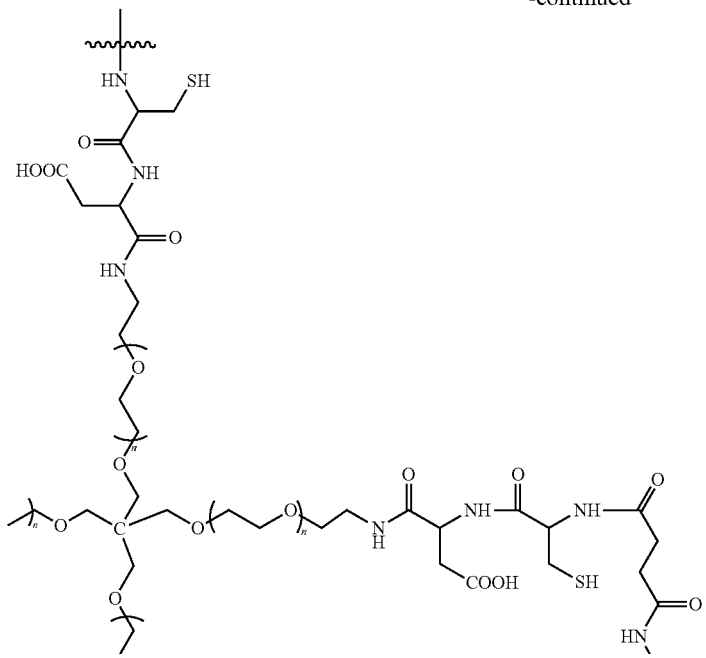
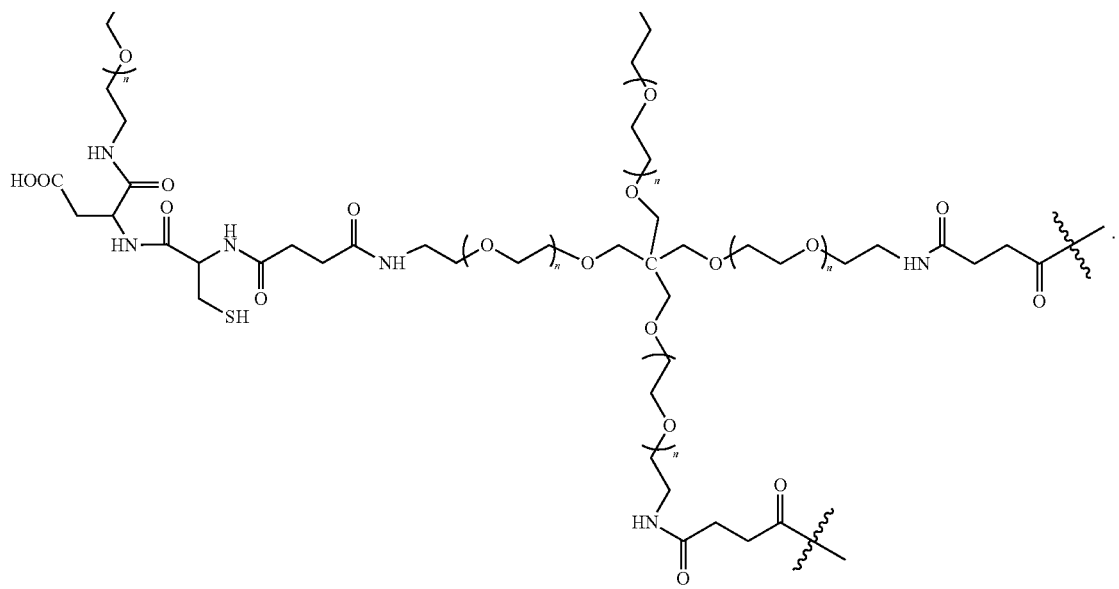
When "R" is
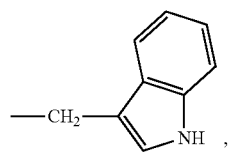
a hydrogel according to the following structure is formed:

(Hydrogel V)
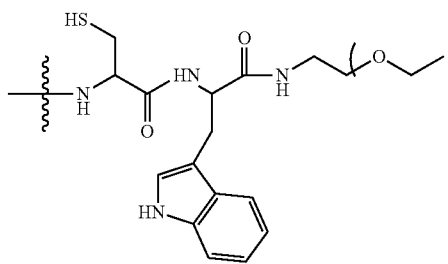
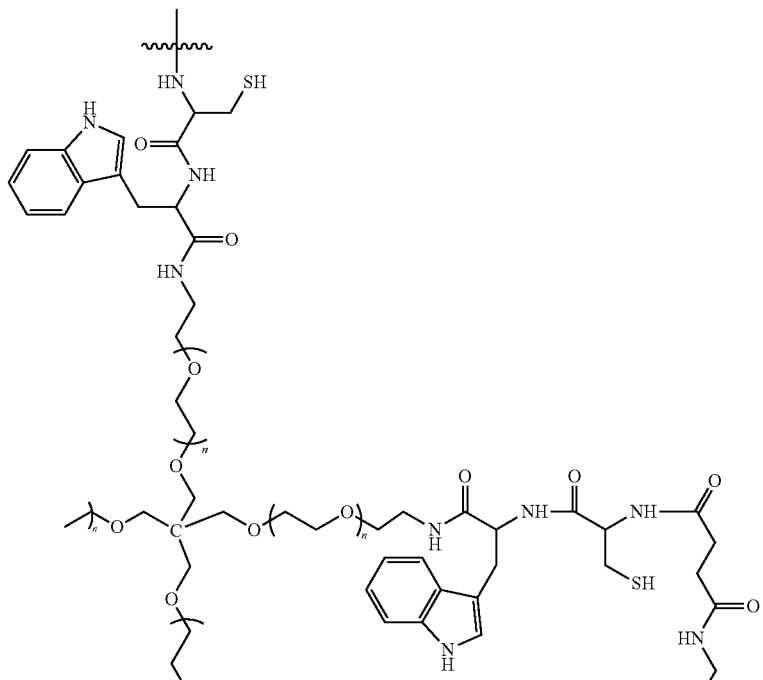
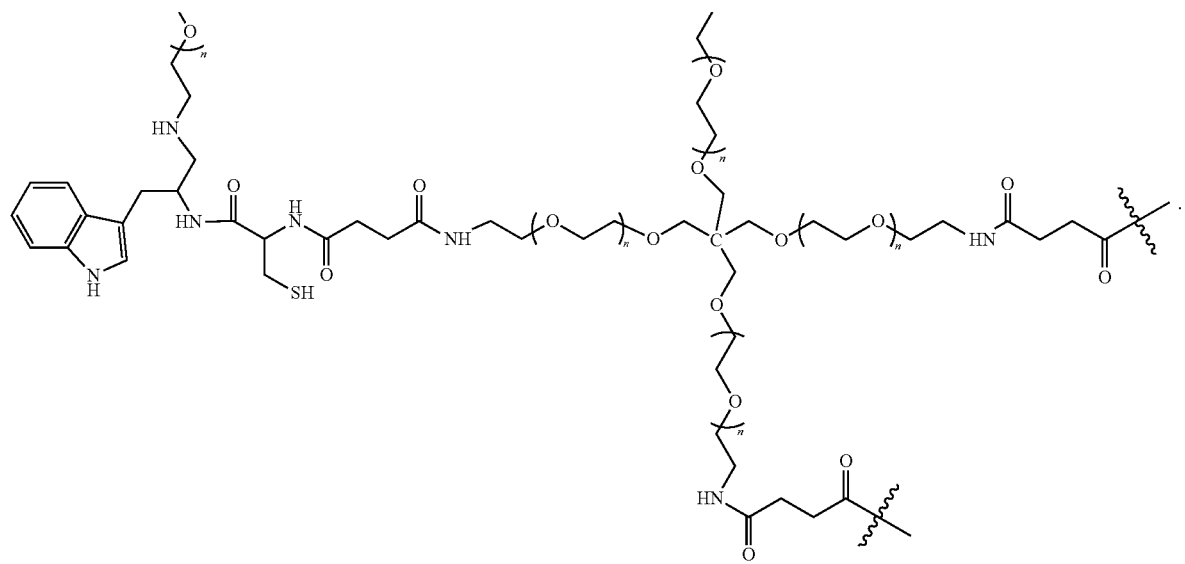

When "R" is $(CH_2)_3NH(NH)CNH_2$, a hydrogel according to the following structure is formed:
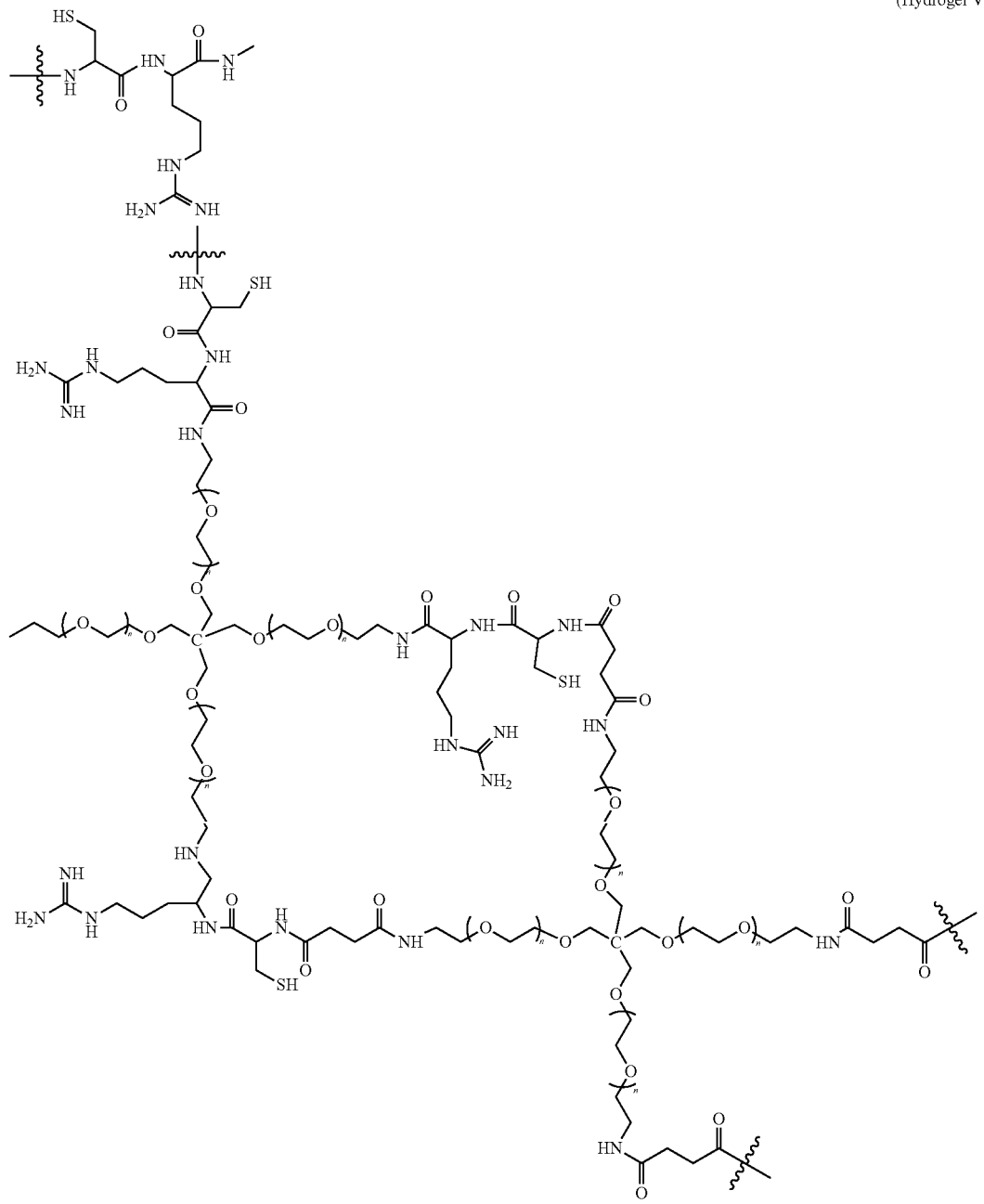
(Hydrogel VI)
The present invention also provides methods of synthesis of the biocompatible macromonomers described above. In a first embodiment, the invention provides a method of synthesizing a macromonomer having the structure:
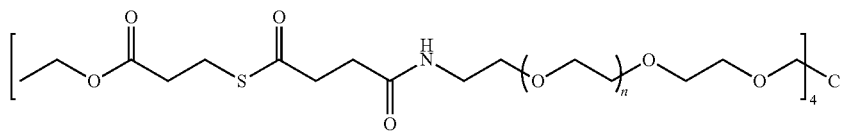
(Formula I)

wherein each "n" has a value in the range of from 0 to 200, the method comprising the steps of (a) preparing a thioester; and (b) coupling the thioester with an amine-terminated 4-armed poly(ethylene glycol), wherein the macromonomer is formed. In a preferred embodiment, the thioester is selected from the group consisting of

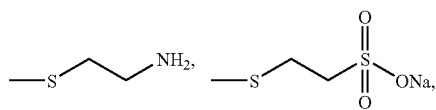

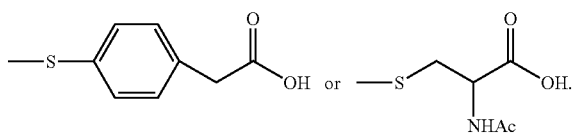

In a second embodiment, the invention provides a method of synthesizing a macromonomer having the structure:

(Formula II)

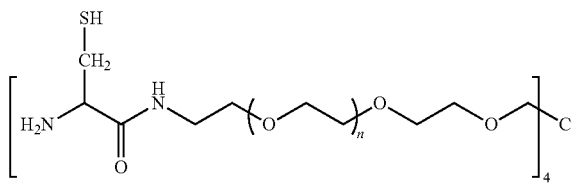

wherein each "n" has a value in the range of from 0 to 200, the method comprising coupling cysteine with an amine-terminated 4-armed poly(ethylene glycol), wherein the macromonomer is formed. In a preferred embodiment, the amine-terminated 4-armed poly(ethylene glycol) is PEG4.

In a third embodiment, the invention provides a method of synthesizing a macromonomer having the structure:

(Formula III)

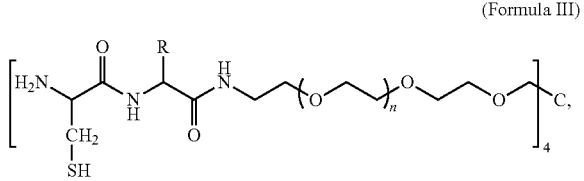

wherein each "n" has a value in the range of from 0 to 200, and wherein R is selected from the group consisting of H, CH₂CH₂COOH, CH₂COOH,

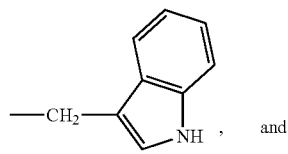

(CH₂)₃NH(NH)CNH₂, the method comprising coupling a protected cysteine dipeptide with an amine-terminated 4-armed poly(ethylene glycol), wherein the macromonomer is formed. In a preferred embodiment the protected cysteine dipeptide is selected from the group consisting of Boc-Cys(Trt)-OH or Boc-Cys(Trt)-AA-OH and the amine-terminated 4-armed poly(ethylene glycol) is PEG4.

In a fourth embodiment, the invention provides a method of synthesizing a macromonomer having the structure:

(Formula IV)

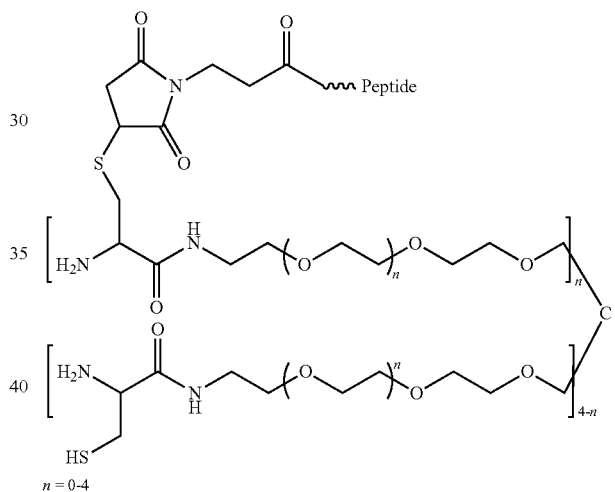

n = 0-4 wherein each "n" has a value in the range of from 0 to 200, the method comprising reacting a 4-armed PEG-cysteine with at least one peptide and a 4-armed PEG thioester, wherein the macromonomer is formed. In a preferred embodiment, the peptide is a maleimide-terminated peptide selected from the group consisting of collagen, fibrinogen, albumin, and fibrin, polysaccharides and glycosaminoglycans such as GRGDSPG-NH₂ (SEQ ID NO: 1) or OEG2-FEWTPGWYQPY-NH₂ (SEQ ID NO: 2).

The present invention also provides methods of use of the biocompatible hydrogels disclosed herein. In a first embodiment the invention provides a method of encapsulating a biological sample with biomaterials. The method comprises a) preparing a biocompatible hydrogel according to the following structure:

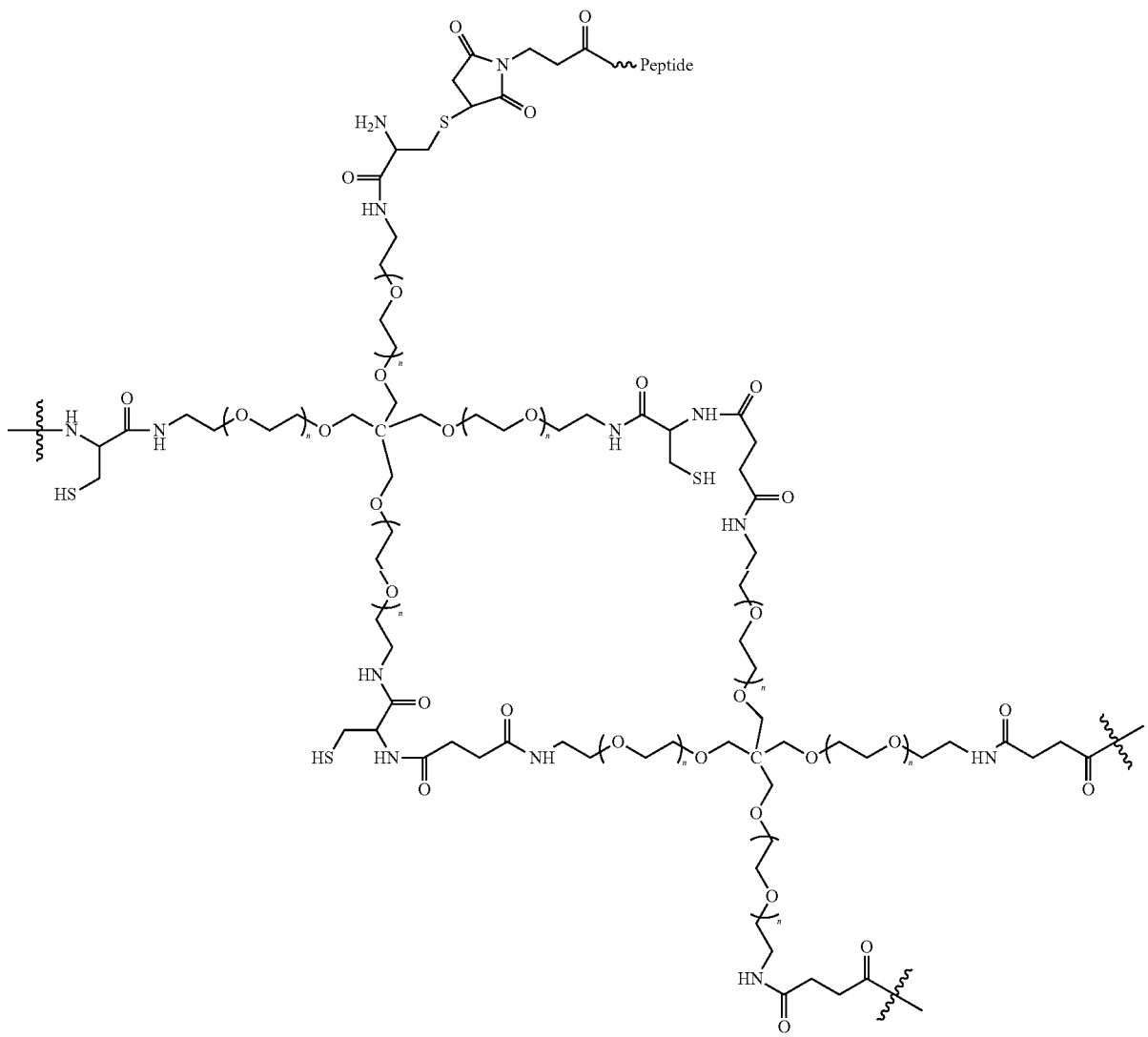

(Hydrogel VII)

wherein each "n" has a value of 0 to 200 and wherein the peptide is a maleimide terminated peptide; b) reacting the biocompatible hydrogel with a biomaterial to form a modified biocompatible hydrogel; and c) contacting the biological sample with the modified biocompatible hydrogel, wherein the hydrogel surrounds and encapsulates the sample. In a preferred embodiment the biomaterial is an anti-inflammatory peptide, such as an inhibitor of cell surface IL-1 receptor. In a further preferred embodiment the IL-1 receptor has sequence FEWTPGWYQPY (SEQ ID NO: 2) wherein the terminus is modified with an amine group $NH_2$.

The present invention has many advantages. For instance, the inventors show herein that the NCL crosslinked synthetic polymer hydrogels of the present invention can be biodegradable and functionalized with bioactive compounds, and if the crosslinking is sufficiently rapid, the hydrogel can form in-situ from a liquid precursor. The methods of synthesis described herein are also advantageous compared to other methods of hydrogel synthesis, as they utilize mild reaction conditions, do not require initiators or other potentially harmful compounds, and form thiol functional groups on the polymer hydrogel network as a result of rearrangement during NCL reaction. (Thiol functional groups increase bioadhesion and enhance the permeation of polymers in oral delivery of biomacromolecules (Bernkop-Schnurch, 2003), and they can further be used as a convenient location for functionalization of the hydrogel with bioactive compounds for tissue regeneration and drug delivery).

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION OF THE INVENTION

Figure 1:
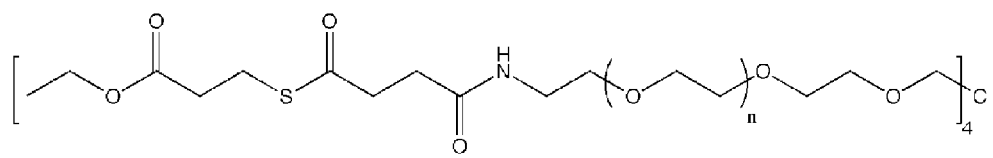
FIG. 1. Novel biocompatible macromonomers according to Formulas I-IIIa-e.
Figure 1:
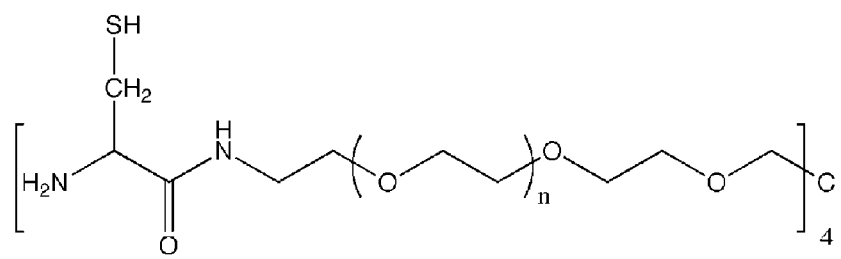
Figure 1:
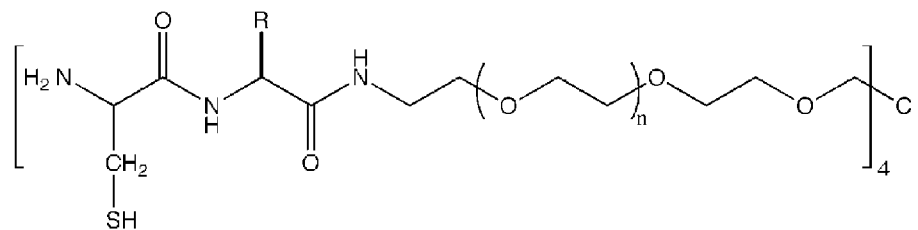

The present invention provides novel biocompatible macromonomers, biocompatible hydrogels, methods of synthesis and methods of use thereof.

I. In General

In the specification and in the claims, the terms "including" and "comprising" are open-ended terms and should be interpreted to mean "including, but not limited to . . . " These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

The present invention provides novel biocompatible macromonomers, biocompatible hydrogels, methods of synthesis and methods of use thereof. The biocompatible hydrogels of the present invention are prepared using native chemical ligation (NCL), in which a thioester readily reacts with a N-terminal thiol (cysteine) through transesterification and rearrangement to form an amide bond through a five-member ring intermediate.

A. Biocompatible Macromonomers

The present invention surprisingly provides new biocompatible thioester-polymer and N-terminal cysteine-polymer macromonomers. By "biocompatible" we mean a macromonomer that does not have toxic or injurious effects on biological systems and exhibits minimal local inflammatory response in surrounding tissues. For instance, the polyethylene glycol core of the preferred embodiment of the present macromonomers is well recognized as being biocompatible, as they are non-immunogenic and resistant to nonspecific protein and cell adhesions. The macromonomers of the present invention are useful in a wide variety of applications, including, for instance, tissue repair, wound healing, drug delivery, preventing surgical adhesions, as coatings on medical devices, and thin adherent hydrogels on biosensors and chip-based diagnostic devices for genomic and proteomic assays.

In one embodiment, the invention provides a biocompatible macromonomer comprising the structure:

(Formula I)

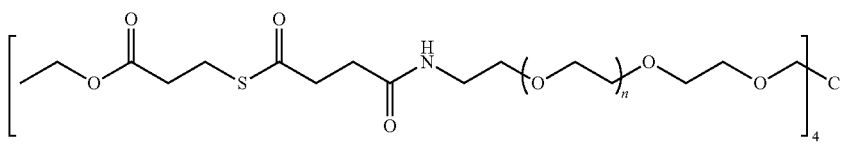

wherein each "n" has a value in the range of from 0 to 200. Each "n" represents the polymeric core of the present macromonomer, and does not have to be the same value. In a preferred embodiment each "n" has a value ranging from 10 to 400, more preferably from 20 to 300, and further more preferably from 50 to 200. For instance, in a preferred example, the polymeric core represents 10 to 400 units of polyethylene glycol (PEG), with a total molecular weight (MW) ranging from 500 to 30,000 kDa. In other preferred embodiments the total MW of the polymeric core ranges from about 1,000 to about 20,000 kDa. While PEG comprises the polymeric core in a preferred embodiment, alternative polymeric cores including but not limited to linear or branched biocompatible polymers that can be similarly functionalized may also be used in the macromonomer of the present invention. By "functionalized" we mean modifying any linear or branched biocompatible polymer with N-terminal cysteine peptides as side chain functional groups or endgroups, or similar polymers functionalized with thioesters. In a preferred embodiment, where PEG comprises the polymeric core of the macromonomer, there are four arms ("n") emanating from the center of the macromonomer of the present invention. However, in alternative embodiments, the polymeric core could comprise six to eight or even ten to twenty different arms emanating from the center of the macromonomer.

In another embodiment, the invention provides a biocompatible macromonomer comprising the structure:

(Formula II)

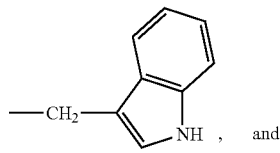

wherein each "n" has a value in the range of from 0 to 200. Each "n" represents the polymeric core of the present macromonomer, and does not have to be the same value. In a preferred embodiment each "n" has a value ranging from 10 to 400, more preferably from 20 to 300, and further more preferably from 50 to 200. For instance, in a preferred example, the polymeric core represents 10 to 400 units of polyethylene glycol (PEG), with a total molecular weight (MW) ranging from 500 to 30,000 kDa. In other preferred embodiments the total MW of the polymeric core ranges from about 1,000 to about 20,000 kDa. While PEG comprises the polymeric core in a preferred embodiment, alternative polymeric cores including but not limited to linear or branched biocompatible polymers that can be similarly functionalized may also be used in the macromonomer of the present invention. By "functionalized" we mean modifying any linear or branched biocompatible polymer with N-terminal cysteine peptides as side chain functional groups or endgroups, or similar polymers functionalized with thioesters. In a preferred embodiment, where PEG comprises the polymeric core of the macromonomer, there are four arms ("n") emanating from the center of the macromonomer of the present invention. However, in alternative embodiments, the polymeric core could comprise six to eight or even ten to twenty different arms emanating from the center of the macromonomer.

In another embodiment, the invention provides a biocompatible macromonomer comprising the structure:

(Formula III)

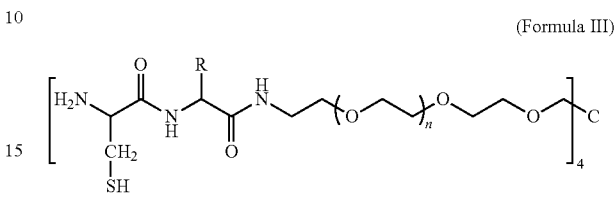

wherein each "n" has a value in the range of from 0 to 200. Each "n" represents the polymeric core of the present macromonomer, and does not have to be the same value. In a preferred embodiment each "n" has a value ranging from 10 to 400, more preferably from 20 to 300, and further more preferably from 50 to 200. For instance, in a preferred example, the polymeric core represents 10 to 400 units of polyethylene glycol (PEG), with a total molecular weight (MW) ranging from 500 to 30,000 kDa. In other preferred embodiments the total MW of the polymeric core ranges from about 1,000 to about 20,000 kDa. While PEG comprises the polymeric core in a preferred embodiment, alternative polymeric cores including but not limited to linear or branched biocompatible polymers that can be similarly functionalized may also be used in the macromonomer of the present invention. By "functionalized" we mean modifying any linear or branched biocompatible polymer with N-terminal cysteine peptides as side chain functional groups or endgroups, or similar polymers functionalized with thioesters. In a preferred embodiment, where PEG comprises the polymeric core of the macromonomer, there are four arms ("n") emanating from the center of the macromonomer of the present invention. However, in alternative embodiments, the polymeric core could comprise six to eight or even ten to twenty different arms emanating from the center of the macromonomer.

In a preferred embodiment, R is selected from the group consisting of H, $CH_2CH_2COOH$, $CH_2COOH$,

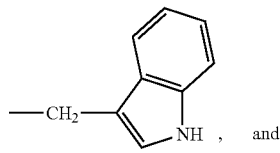

, and $(CH_2)_3NH(NH)CNH_2$. However, R can be any amino acid side chain, including but not limited to all natural and non-natural amino acid side chains that might add a desired biological or physical property, as well as any peptide.

In another embodiment, the invention provides a biocompatible macromonomer comprising the structure:

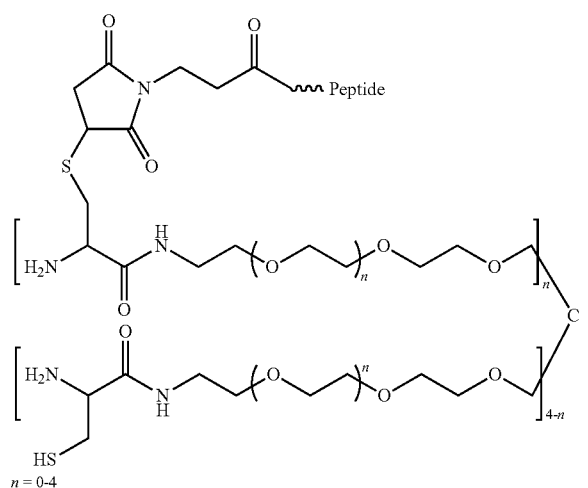

(Formula IV)

n = 0-4 wherein each "n" has a value in the range of from 0 to 200. wherein each "n" has a value in the range of from 0 to 200. Each "n" represents the polymeric core of the present macromonomer, and does not have to be the same value. In a preferred embodiment each "n" has a value ranging from 10 to 400, more preferably from 20 to 300, and further more preferably from 50 to 200. For instance, in a preferred example, the polymeric core represents 10 to 400 units of polyethylene glycol (PEG), with a total molecular weight (MW) ranging from 500 to 30,000 kDa. In other preferred embodiments the total MW of the polymeric core ranges from about 1,000 to about 20,000 kDa. While PEG comprises the polymeric core in a preferred embodiment, alternative polymeric cores including but not limited to linear or branched biocompatible polymers that can be similarly functionalized may also be used in the macromonomer of the present invention. By "functionalized" we mean modifying any linear or branched biocompatible polymer with N-terminal cysteine peptides as side chain functional groups or endgroups, or similar polymers functionalized with thioesters. In a preferred embodiment, where PEG comprises the polymeric core of the macromonomer, there are four arms ("n") emanating from the center of the macromonomer of the present invention. However, in alternative embodiments, the polymeric core could comprise six to eight or even ten to twenty different arms emanating from the center of the macromonomer.

The peptide of the present invention is preferably a maleimide-terminated peptide or protein selected from the group consisting of collagen, fibrinogen, albumin, and fibrin, polysaccharides and glycosaminoglycans, although other types of biomolecules may also be used, such as growth factors, antibodies, oligosaccharides, DNA, RNA etc. For instance, in one embodiment, the peptides are GRGDSPG (SEQ ID NO: 1) or OEG2-FEWTPGWYQPY (SEQ ID NO: 2) wherein both peptides are modified with an amine group at the terminus end —$NH_2$, or anti-diabetic polypeptides glucagon-like peptide 1 and exendin-4.

B. Biocompatible Hydrogels

The present invention surprisingly provides new biocompatible hydrogels comprising covalently crosslinked thioester-polymer (Formula I) and N-terminal cysteine-polymer macromonomers (Formulas II-III) as described above. By "biocompatible" we mean a hydrogel that does not have toxic or injurious effects on biological systems. The hydrogels of the present invention are useful in a wide variety of applications, including, for instance, medically useful devices or implants that can release bioactive compounds in a controlled manner for local, systemic, or targeted drug delivery; medically useful devices or implants for use as surgical adhesion prevention barriers, implantable wound dressings, scaffolds for cellular growth for tissue engineering or as surgical tissue adhesives or sealants; biomaterials for preventing transplant rejection; and other medically useful applications such as hydrogel coatings for preventing bacterial infection of medical device surfaces, and coatings for chip-based assays of DNA, RNA or proteins.

In one embodiment, the invention comprises a biocompatible hydrogel according to the structure:

(Hydrogel I)

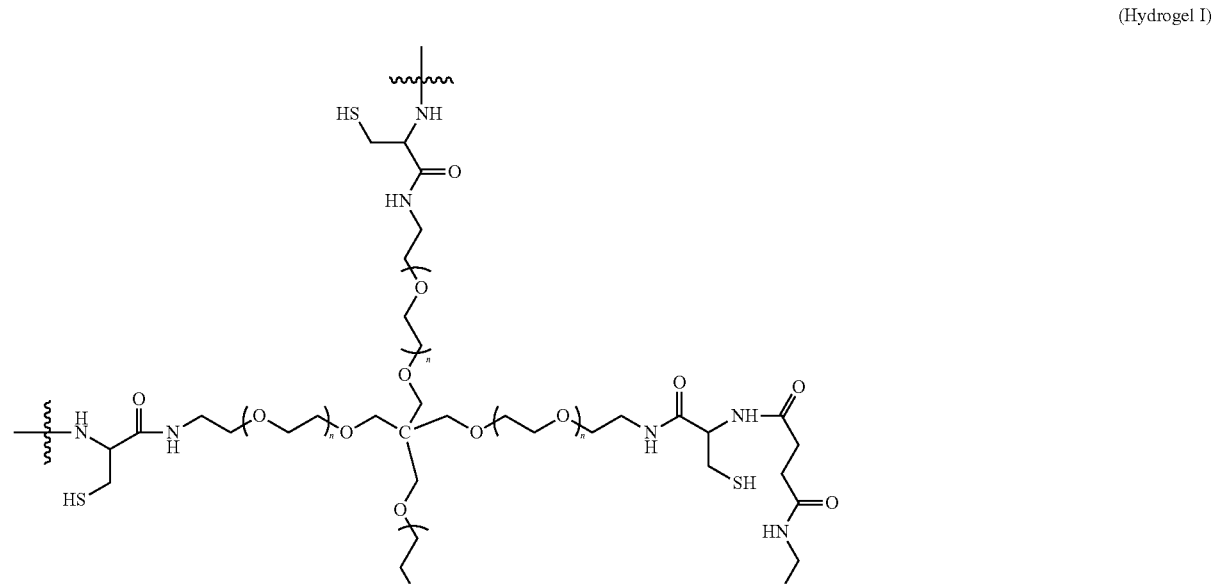

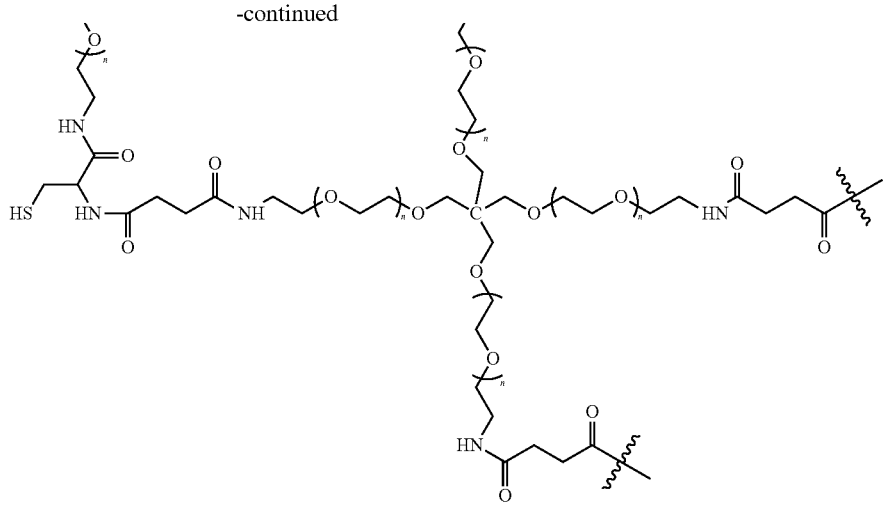

wherein each "n" has a value in the range of from 0 to 200. Hydrogel I is formed by covalently crosslinking macromonomers I and II through NCL. Each "n" represents the polymeric core of the present macromonomer, and does not have to be the same value. In a preferred embodiment each "n" has a value ranging from 10 to 400, more preferably from 20 to 300, and further more preferably from 50 to 200. For instance, in a preferred example, the polymeric core represents 10 to 400 units of polyethylene glycol (PEG), with a total molecular weight (MW) ranging from 500 to 30,000 kDa. In other preferred embodiments the total MW of the polymeric core ranges from about 1,000 to about 20,000 kDa. While PEG comprises the polymeric core in a preferred embodiment, alternative polymeric cores including but not limited to linear or branched biocompatible polymers that can be similarly functionalized may also be used in the macromonomer of the present invention. By "functionalized" we mean modifying any linear or branched biocompatible polymer with N-terminal cysteine peptides as side chain functional groups or end-groups, or similar polymers functionalized with thioesters. In a preferred embodiment, where PEG comprises the polymeric core of the macromonomer, there are four arms ("n") emanating from the center of the macromonomer of the present invention. However, in alternative embodiments, the polymeric core could comprise six to eight or even ten to twenty different arms emanating from the center of the macromonomer. Equivalent amounts of the macromonomers are preferred, although other ratios of macromonomers are envisioned, including but not limited to ratios ranging from 0.25:1, 0.5:1, 0.75:1, 1:1, 1.25:1, 1.5:1, 2:1, etc.

In alternate embodiments, the invention comprises a biocompatible hydrogel formed by covalently crosslinking macromonomers according to Formulas I and III through NCL wherein each "n" has a value ranging from 0 to 200. Equivalent amounts of the macromonomers are preferred, although other ratios of macromonomers are envisioned, including but not limited to ratios ranging from 0.25:1, 0.5:1, 0.75:1, 1:1, 1.25:1, 1.5:1, 2:1, etc.

For instance, where the second macromonomer has a structure according to Formula III:

(Formula III)

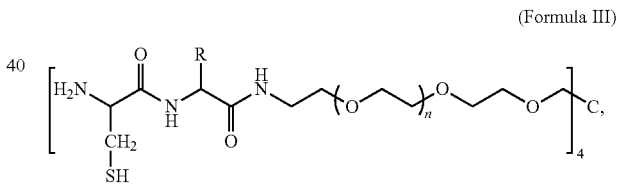

wherein "R" is hydrogen, a hydrogel according to the following structure is formed:

(Hydrogel II)

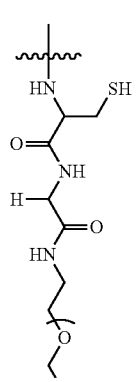

-continued
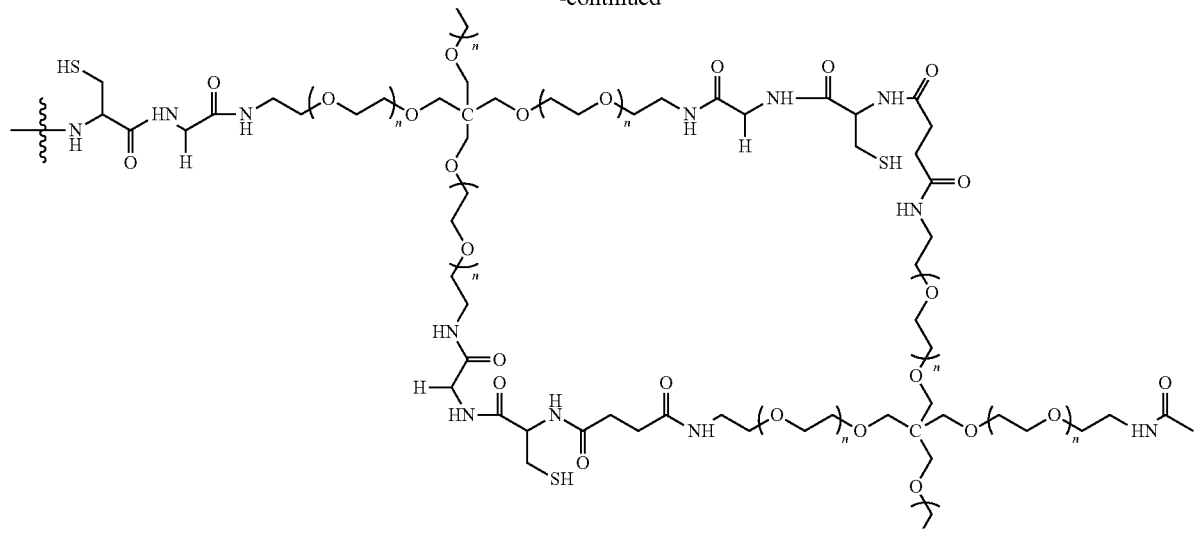
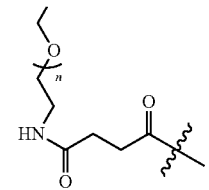
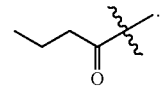
When "R" is CH₂CH₂COOH, a hydrogel according to the following structure is formed:
(Hydrogel III)
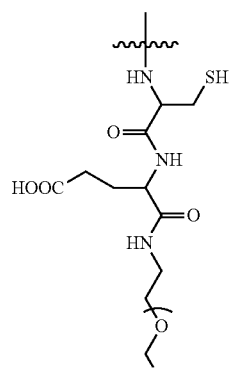

-continued
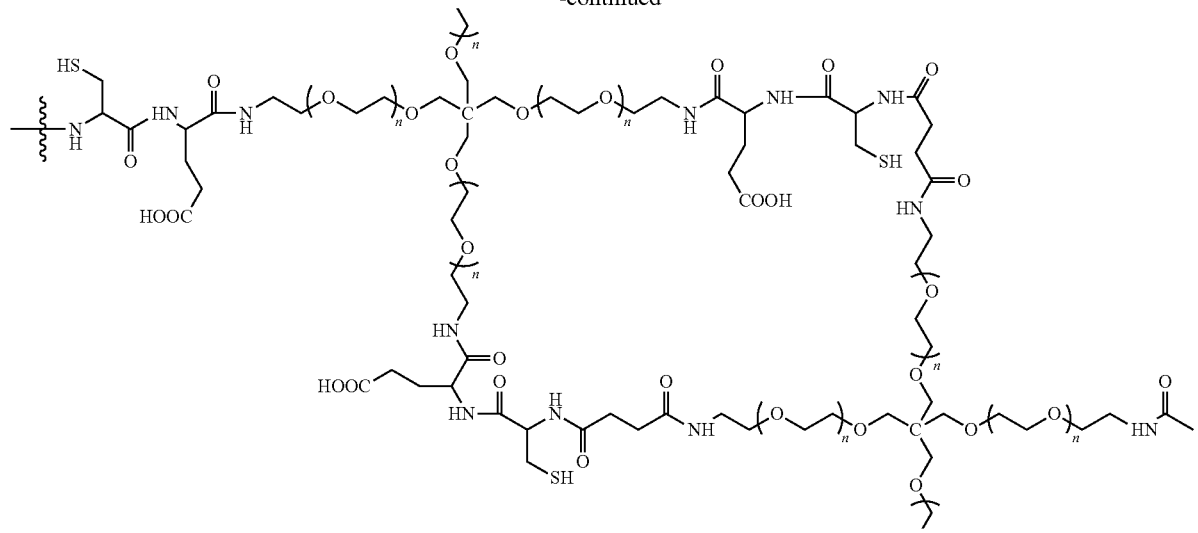
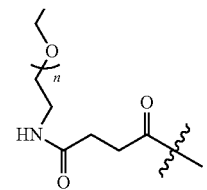
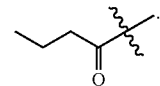
When "R" is CH₂COOH, a hydrogel according to the following structure is formed:
(Hydrogel IV)
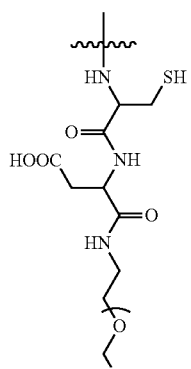

-continued
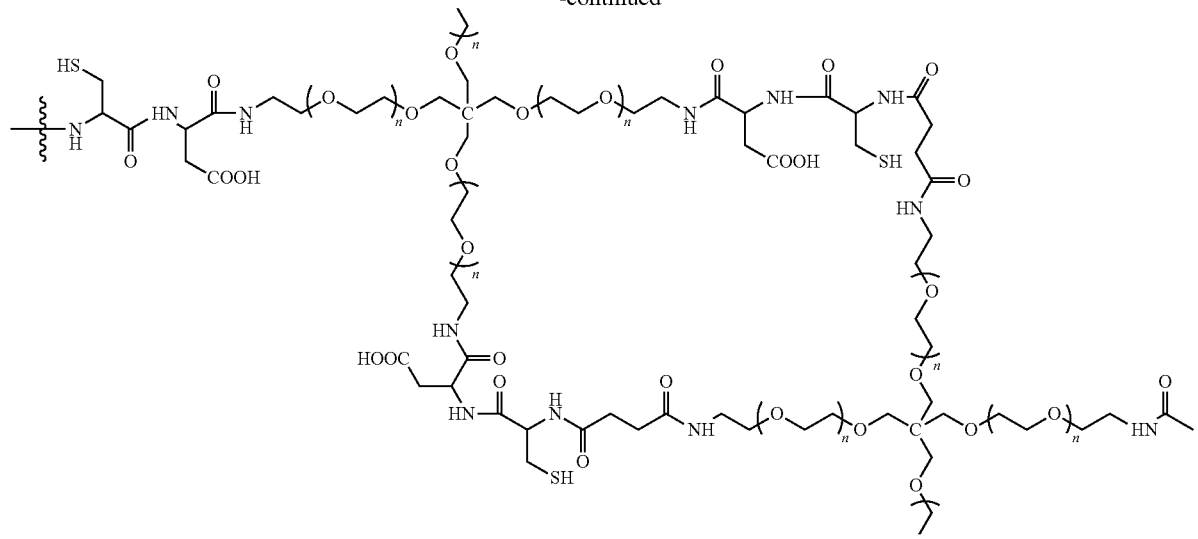
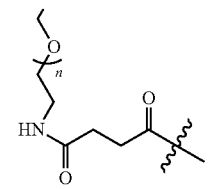
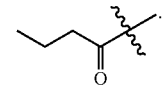
When "R" is
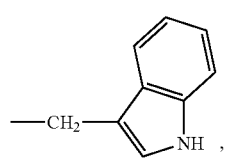
a hydrogel according to the following structure is formed:
(Hydrogel V)
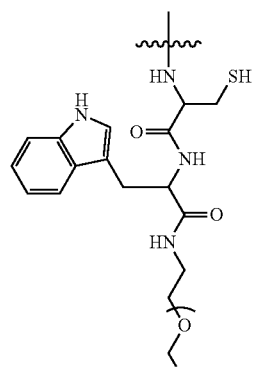

-continued
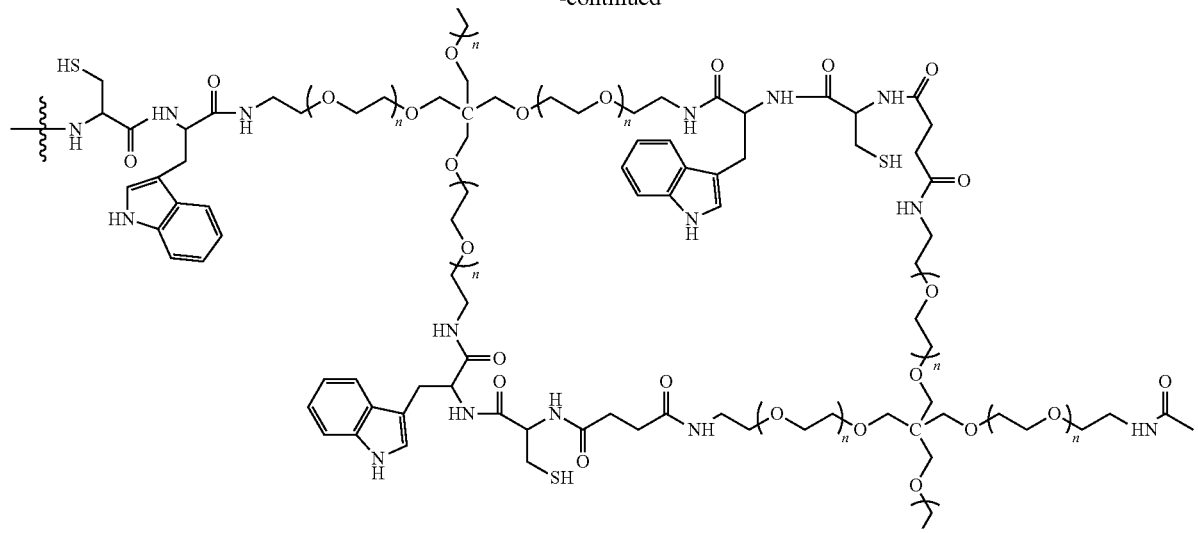
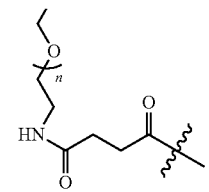
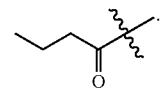
When "R" is (CH₂)₃NH(NH)CNH₂, a hydrogel according to the following structure is formed:
(Hydrogel VI)
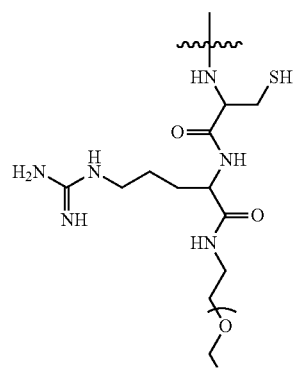

-continued

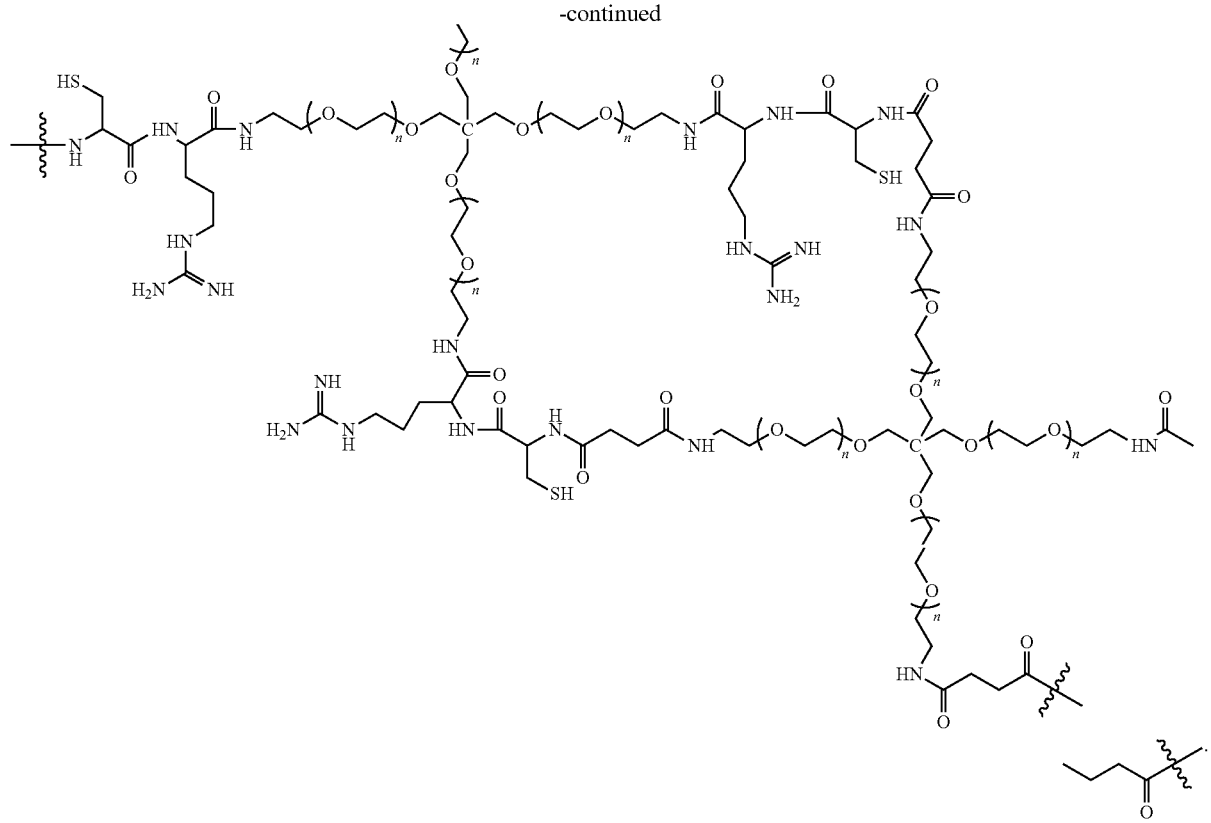

The present invention also provides methods of synthesis of the biocompatible macromonomers described above. In a first embodiment, the invention provides a method of synthesizing a macromonomer having the structure:

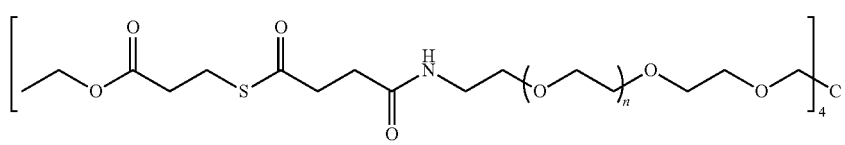

(Formula I)

wherein each "n" has a value in the range of from 0 to 200, the method comprising the steps of (a) preparing a thioester; and (b) coupling the thioester with an amine-terminated 4-armed poly(ethylene glycol), wherein the macromonomer is formed. In a preferred embodiment, the thioester is selected from the group consisting of

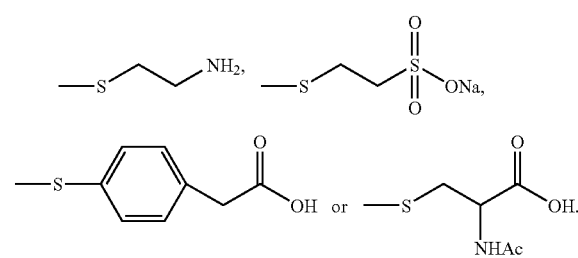

C. Methods of Synthesis

Figure 16:
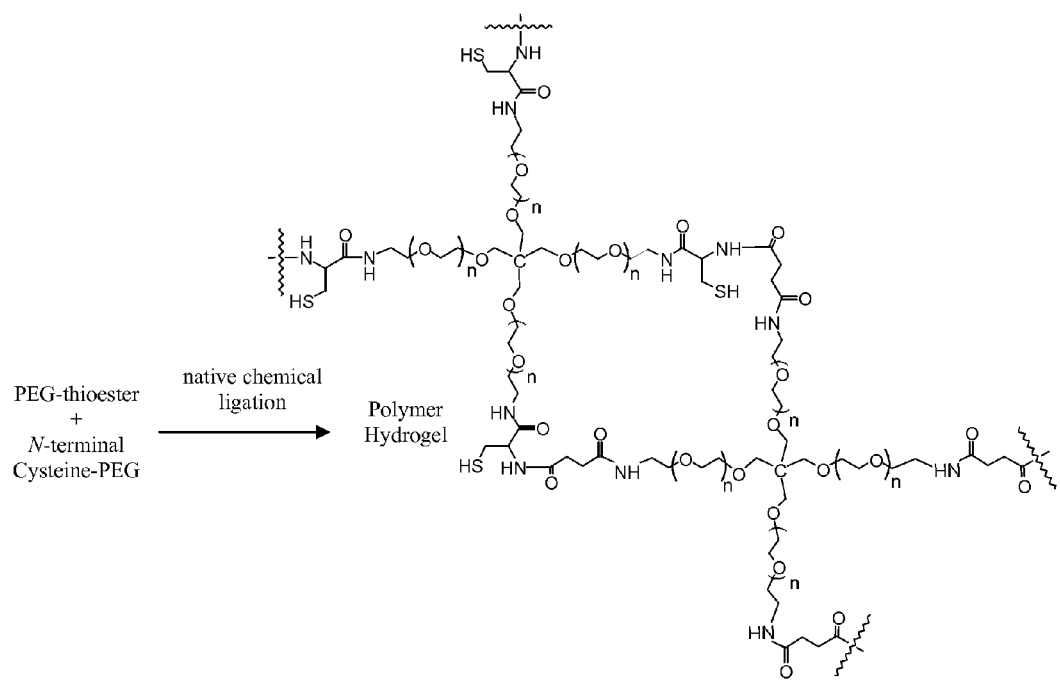
FIG. 16. Synthesis of Hydrogel I.

The invention also provides novel methods of synthesis of the biocompatible macromonomers and hydrogels described above. In general, the inventors exploited NCL to form covalently crosslinked polymer macromonomers under physiological conditions (FIG. 1). The macromonomers were then covalently crosslinked using NCL (FIG. 16) to form biocompatible hydrogels. The reaction conditions described herein lead to rapid hydrogel formation by NCL, and the viscoelastic behavior of the hydrogels was measured by oscillatory rheology (FIGS. 5-9).

The methods comprise crosslinking 4-armed PEG cysteine (4A-PEG-Cys) and 4-armed PEG thioester (4A-PEG-ThE) through NCL to form a biocompatible hydrogel. The advantages of this methods as compared to other synthetic hydrogel formation techniques are that the reaction is very specific and biocompatible. The covalent crosslinking is mostly limited between the cystine and thioester groups on the PEG molecules, whereas in other hydrogel forming methods crosslinking can also occur between the synthetic macromers and biological components such as cell surface proteins and agents in the culture media. The hydrogel formation occurs under mild physiological conditions (pH 7-9), bearing a minimal toxicity to the cells during encapsulation. Furthermore, the resultant hydrogel presents thiol groups that promote cell adhesion inside the hydrogel network and their mild reductive properties can also be used to protect encapsulated cells from oxidative stress.

The methods of macromonomer and hydrogel formation described herein provide biocompatible macromonomers and hydrogels which are easily modified with bioactive materials to improve functions of encapsulated cells such as supporting cell growth, and the development and secretion of cellular products upon biological stimulus. By "bioactive" we mean a substance that has or cause an effect on in biological samples. In this work, the macromonomers and hydrogels were functionalized with peptides, although other bioactive materials such as proteins, growth factors, DNA, RNA. Peptides were functionalized through the Michael Addition reaction between 4A-PEG-ThE and maleimide-terminated peptides prior to the crosslinking between 4A-PEG-Cys and 4A-PEG-ThE. This reaction is quantitative and fast, providing a good control over the density of peptides attached to the resulted hydrogel. Such strategy works well when the physiological effects of peptides on cells can be achieved at low immobilization density. For example, presence of the cell adhesion peptide GRGDSPG at 1% of the total cystine groups used for hydrogel formation was sufficient to support cell adhesion in our case.

However, other methods of functionalization are also incorporated in the scope of this invention. For instance, other methods of functionalization may be used if more peptides need to be presented (above 10% of total cysteine groups on 4A-PEG-Cys). One of these methods is to use peptide-incorporated Cys-PEG macromonomers (bioactive peptide conjugated between Cys and PEG moiety on one or multiple arms of PEG4) to form the hydrogel by NCL and present peptides on high densities. Alternatively, peptide-incorporated PEG-Cys macromers (peptide-conjugated PEGs with N-terminal Cys) also be used to form the hydrogel by NCL and present peptides on high densities. Crosslinking polymers through NCL allows the use of multiple strategies known to the art for hydrogel functionalization according to the present invention.

In one embodiment, the invention provides a method of synthesizing a biocompatible macromonomer comprising the structure:

wherein each "n" has a value in the range of from 0 to 200, the method comprising preparing a thioester and coupling the thioester with an amine-terminated 4-armed poly(ethylene glycol). In a preferred embodiment the thioester is ethyl 3-mercaptopropionate, although other thioesters including but not limited to

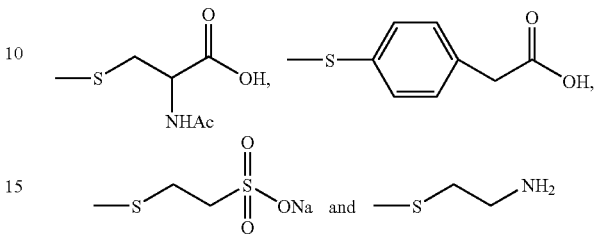

are encompassed in the scope of this invention. In a preferred embodiment the amine-terminated 4-armed poly(ethylene glycol) is PEG4, although other poly(ethylene glycols) may also be used.

In another embodiment, the invention provides a method of synthesizing a biocompatible macromonomer comprising the structure:

(Formula II)

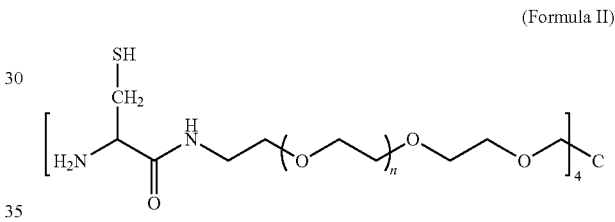

wherein each "n" has a value in the range of from 0 to 200, the method comprising coupling cysteine with an amine-terminated 4-armed poly(ethylene glycol). In a preferred embodiment the amine-terminated 4-armed poly(ethylene glycol) is PEG4, although other poly(ethylene glycols) may also be used.

In another embodiment, the invention provides a method of synthesizing a biocompatible macromonomer comprising the structure:

(Formula III)

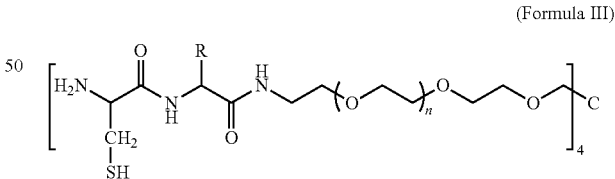

wherein R is selected from the group consisting of H, CH₂CH₂COOH, CH₂COOH, (Formula I)

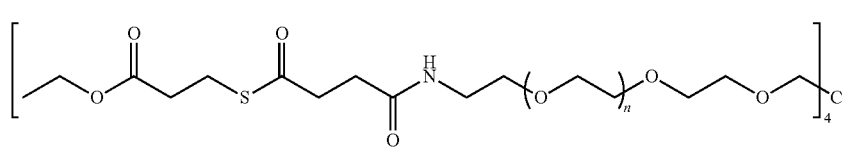

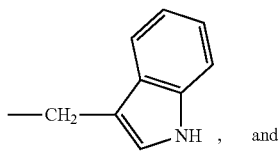

$(CH_2)_3NH(NH)CNH_2$ and wherein each "n" has a value in the range of from 0 to 200, the method comprising coupling a protected cysteine dipeptide with an amine-terminated 4-armed poly(ethylene glycol). In a preferred embodiment the protected cysteine dipeptide is selected from the group consisting of Boc-Cys(Trt)-OH or Boc-Cys(Trt)-AA-OH, although other dipeptides may be used. In a preferred embodiment the amine-terminated 4-armed poly(ethylene glycol) is PEG4, although other poly(ethylene glycols) may also be used.

In another embodiment, the invention provides a method of synthesizing a biocompatible macromonomer comprising the structure:

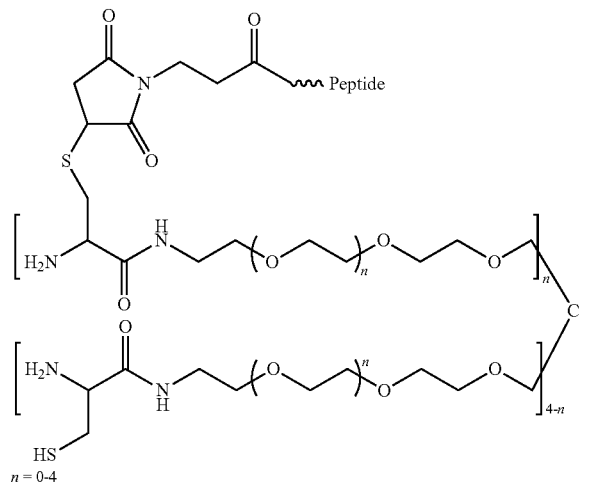

(Formula IV)

$n = 0\text{-}4$ wherein each "n" has a value in the range of from 0 to 200, the method comprising reacting a 4-armed PEG-cysteine with at least one peptide and a 4-armed PEG thioester. In a preferred embodiment the peptide is a maleimide-terminated peptide selected from the group consisting of collagen, fibrinogen, albumin, and fibrin, polysaccharides and glycosaminoglycans, although other types of peptides may also be used. For instance, in one embodiment, the peptides are GRGDSPG (SEQ ID NO: 1) or OEG2-FEWTPGWYQPY (SEQ ID NO: 2), wherein both peptides are modified at the terminus end with and amine group —$NH_2$.

D. Methods of Use

The biocompatible macromonomers and hydrogels of the present invention are useful in a wide variety of medically useful devices and implants. For instance, the biocompatible macromonomers of the present invention are useful in applications ranging from tissue repair, wound healing, drug delivery, preventing surgical adhesions, as coatings on medical devices, and thin adherent hydrogels on biosensors and chip-based diagnostic devices for genomic and proteomic assays.

The biocompatible hydrogels of the present invention are useful in forming medically useful devices or implants that can release bioactive compounds in a controlled manner for local, systemic, or targeted drug delivery. Further, the biocompatible hydrogels are useful in forming medically useful devices or implants for use as surgical adhesion prevention barriers, implantable wound dressings, scaffolds for cellular growth for tissue engineering or as surgical tissue adhesives or sealants. Further still, the biocompatible hydrogels are useful in forming peptide-functionalized hydrogels which can protect transplanted tissue from rejection, specifically, the peptide-functionalized hydrogels can protect pancreatic islet cells from inflammatory response post-transplantation.

In one embodiment, the present invention provides a method of encapsulating a biological sample with biomaterials comprising preparing a biocompatible hydrogel according to the following structure:

(Hydrogel I)

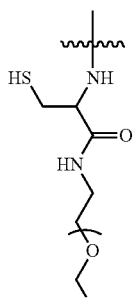

-continued

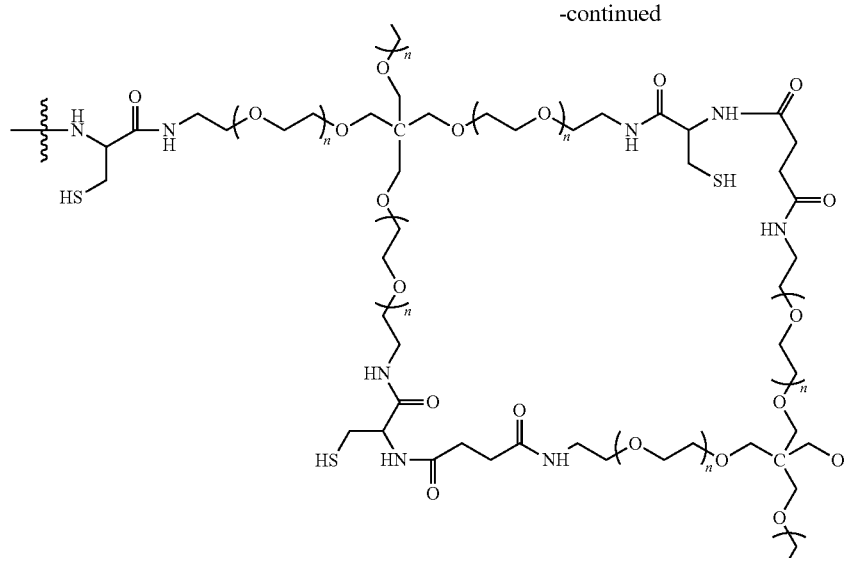
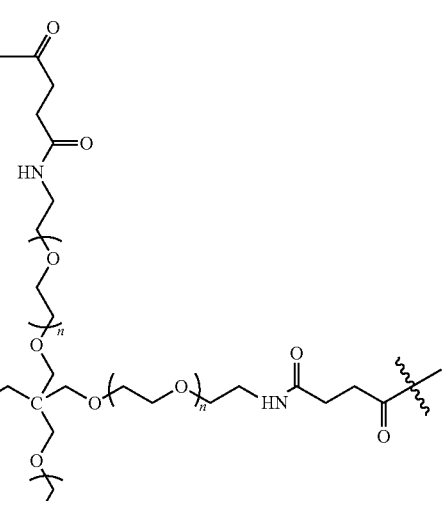
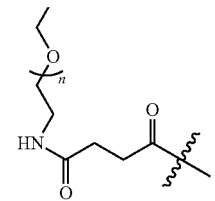

reacting the biocompatible hydrogel with a biomaterial to form a modified biocompatible hydrogel and contacting the biological sample with the modified biocompatible hydrogel, wherein the hydrogel surrounds and encapsulates the sample. By "biological sample" we mean to include a specimen or culture obtained from any source. Biological samples can be obtained from animals (including humans) and encompass fluids, solids, tissues, and gases. Biological samples include blood products, such as plasma, serum and the like. Such examples are not however to be construed as limiting the sample types applicable to the present invention.

By "biomaterials" we mean materials selected from the group consisting of anti-inflammatory agents, cell function promoting agents, various artificial implants, pacemakers, valves, catheters, and membranes (e.g., a dialyzer), as well as synthetic polymers such as polypropylene oxide (PPO) and polyethylene glycol (PEG). In a further preferred embodiment the biomaterial is an anti-inflammatory peptide such as an inhibitor of cell surface IL-1 receptor.

In a preferred embodiment the hydrogel has the following structure:

(Hydrogel VII)

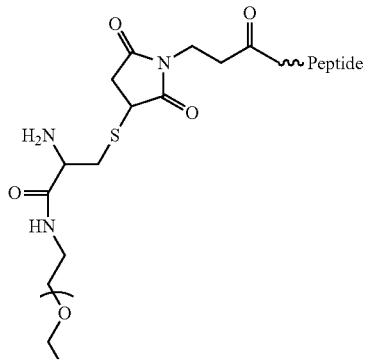

-continued

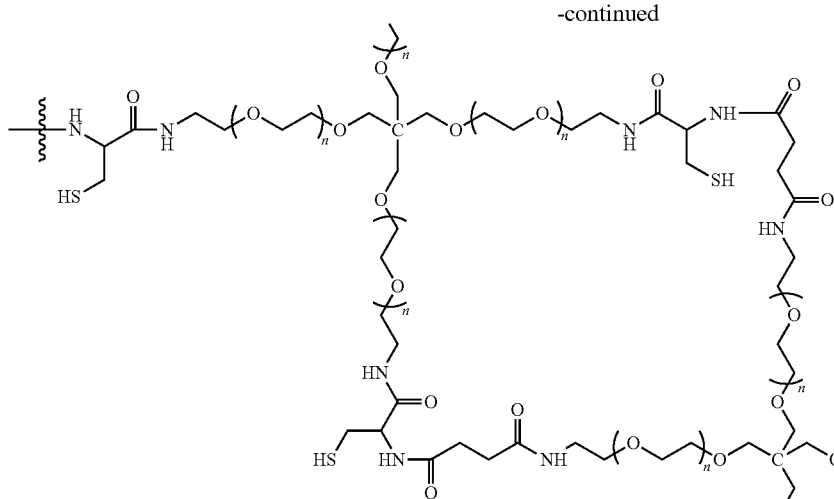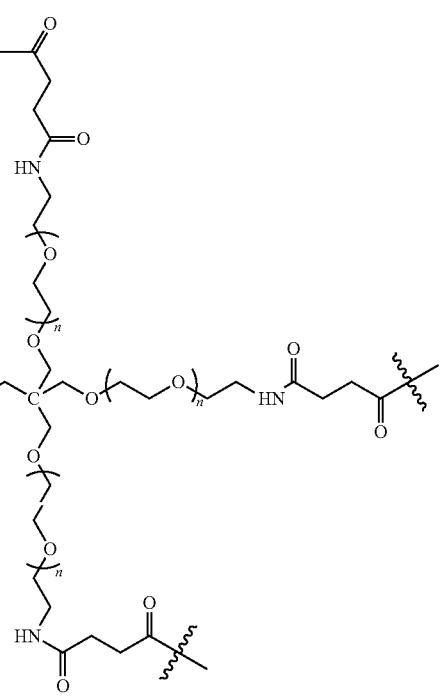

wherein each "n" has a value in the range of from 0 to 200, the method comprising reacting a 4-armed PEG-cysteine with at least one peptide and a 4-armed PEG thioester. In a preferred embodiment the peptide is a maleimide-terminated peptide selected from the group consisting of collagen, fibrinogen, albumin, and fibrin, polysaccharides and glycosaminoglycans, although other types of peptides may also be used. For instance, in one embodiment, the peptides are GRGDSPG (SEQ ID NO: 1) or OEG2-FEWTPGWYQPY (SEQ ID NO: 2) wherein both peptides are modified at the terminus end with an amine group —NH$_2$, i.e., GRGDSPG-NH$_2$ and. OEG2-FEWTPGWYQPY-NH$_2$ D. Kits In an alternate embodiment of the invention, a kit for preparing the biocompatible macromonomers and hydrogels of the present invention is provided. In one embodiment, the kit comprises a biocompatible macromonomer according to at least one of Formulas I-IV and instructions for use.

In a preferred embodiment, the kit comprises a powdered form of at least one of the biocompatible macromonomer according to one of Formulas I-IV, wherein the powdered macromonomer is hydrated by the user for immediate use, such as in a dual syringe device to form a precursor liquid that rapidly gels. Optionally, the kit may contain a solution for dissolving the macromonomer.

In another preferred embodiment, the kit comprises at least one of the biocompatible hydrogels according to one of Hydrogels I-VII discussed above and instructions for use.

In another preferred embodiment, the kit comprises a powdered form of at least one of the biocompatible hydrogels according to one of Hydrogels I-VII discussed above, wherein the powdered hydrogels are hydrated by the user for immediate use, such as in a dual syringe device to form a precursor liquid that rapidly gels. Optionally, the kit may contain a solution for dissolving the hydrogel.

In an alternate embodiment, the kit comprises a biocompatible hydrogel according to the present invention formulated, delivered and stored for use in physiologic conditions.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention. Alternatively, the instructional material can be shipped separately from the container or provided on an electronically accessible form on a internet website with the intention that the instructional material and the biocompatible hydrogel be used cooperatively by the recipient.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Methods of Synthesis

A. Synthesis of Ethyl 3-Mercaptopropionate-Succinic Acid (EMPSA)

Figure 2:
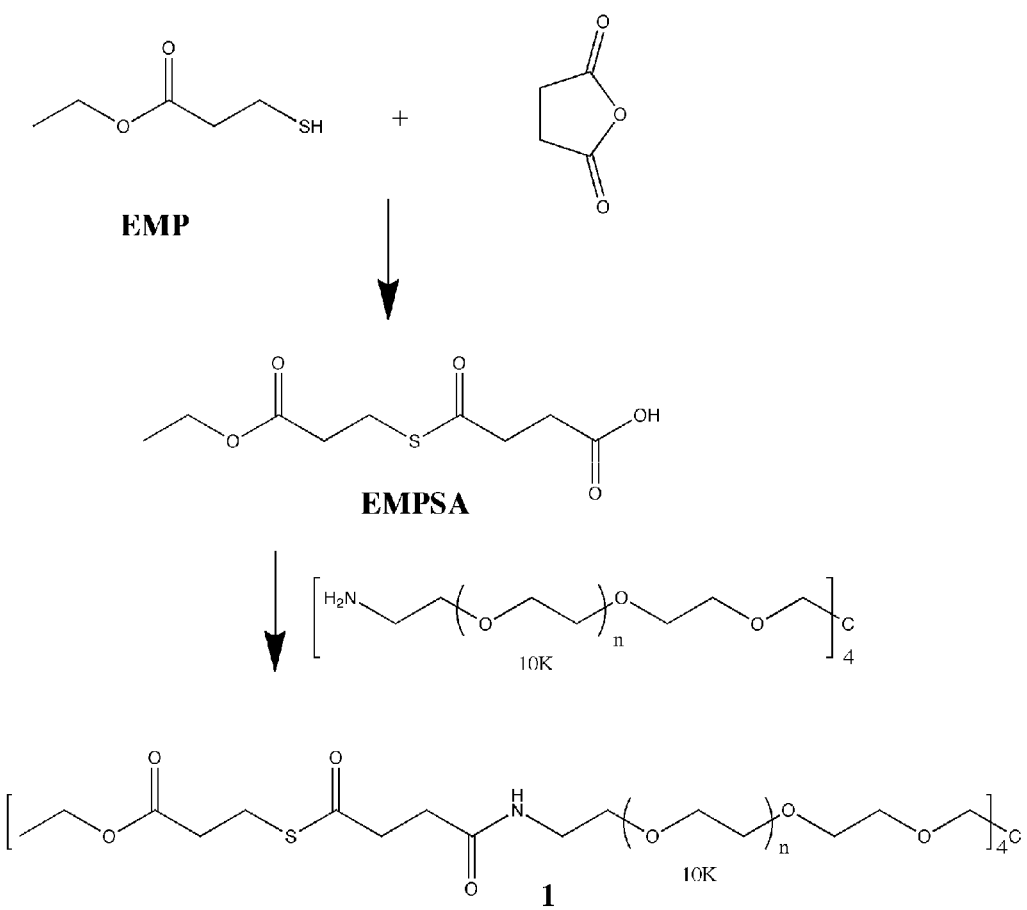
FIG. 2. Synthesis of macromonomers according to Formula I.

As shown in FIG. 2, Ethyl 3-mercaptopropionate (2.95 g, 22 mmol) was added under argon to a stirring solution of succinic anhydride (2.0 g, 20 mmol) and DMAP (122 mg, 1 mmol) in 25 ml of acetonitrile-pyridine (9:1). The reaction mixture was stirred at room temperature overnight. The solution was concentrated under reduced pressure and dried in vacuo. The residue was dissolved in 50 ml of EtOAc. The EtOAc solution was washed with 0.1 N HCl aqueous solution 30 ml×3, H$_2$O×3, dried over anhydrous MgSO$_4$. After filtration, the solution was concentrated to dry under reduced pressure and in vacuo. $^1$H NMR (CDCl$_3$, 500 MHz) δ 10.23 (s, br), 4.14 (2H, q, J=7.0 Hz, —C$\underline{H}_2$—CH$_3$), 3.13 (2H, t, J=7.0 Hz, —S—C$\underline{H}_2$—), 2.88 (2H, t, J=7.0 Hz, —S—CO—C$\underline{H}_2$—), 2.69 (2H, t, J=7.0 Hz, —S—CH$_2$—C$\underline{H}_2$—), 2.62 (2H, t, J=7.0 Hz, —C$\underline{H}_2$—COOH), 1.25 (3H, t, J=7.0 Hz, —CH$_2$—C$\underline{H}_3$).

B. Synthesis of Macromonomer-Formula I

Specifically, a solution of EMPSA (0.234 g, 1 mmol) in DCM (2 ml) was added into a vial containing PEG4A (1 g, 0.4 mmol of amine) and BOP (0.221 g, 1 mmol), followed by addition of DIEA (0.348 ml, 2 mmol). The mixture was vortexed for 5 min, and rocked for 2 hrs. The reaction was monitored by silica gel TLC (solvent system DCM-MeOH—HOAc=100:3:1). The spots on the TLC plate were visualized by spray of 1% ninhydrin solution in ethanol containing 3% HOAc and heat at 105° C. The purification of the product was performed by dilution with MeOH to a final volume of 50 ml. The solution was shaken well and frozen at −20° C. The precipitate was collected by centrifugation (−9° C., 6000 rpm, 20 min) and decanting the solvent. The purification cycle of four steps of dissolution in MeOH at room temperature, freeze at −20° C., centrifugation at −9° C. and decanting the MeOH was repeated for four times, and followed by precipitation with diethyl ether and dried in vacuo (FIG. 2). The ninhydrin test of the purified product gave a yellowish solution. $^1$H NMR (CDCl$_3$, 500 MHz) δ 4.15 (2H, q, J=7.0 Hz, —CH$_2$—CH$_3$), 3.79-3.41 (m, —O—CH$_2$—CH$_2$—O—), 3.12 (2H, t, J=7.0 Hz, —S—CH$_2$—), 2.92 (2H, t, J=7.0 Hz, —S—CO—CH$_2$—), 2.61 (2H, t, J=7.0 Hz, —S—CH$_2$—CH$_2$—), 2.52 (2H, t, J=7.0 Hz, —CH$_2$—COOH), 1.26 (3H, t, J=7.0 Hz, —CH$_2$—CH$_3$).

C. Synthesis of Macromonomer N-terminal Cysteine-PEG4A Conjugates 2, 3a-e

Figure 3:
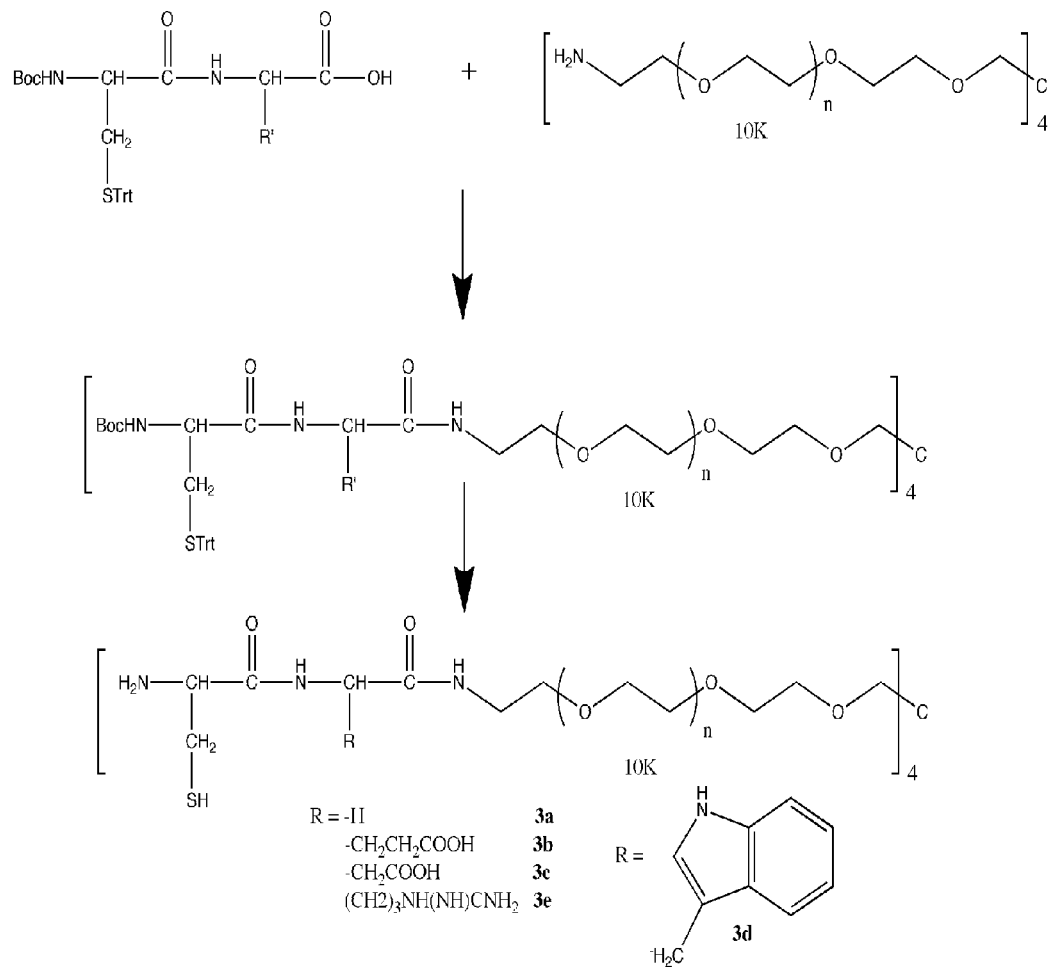
FIG. 3. Synthesis of macromonomers according to Formulas II-IIIa-3.

In this example, the inventors describe the synthesis of macromonomers according to Formulas II-IIIa-e, N-terminal Cysteine-PEG4A Conjugates 2, 3a-e (FIG. 3). Briefly, Boc-Cys(Trt)-OH (150 µmol), PyBop (150 µmol) and 20 µL NMM were dissolved in 5 mL DCM. The mixture was stirred for 10 minutes at room temperature and 4-armed PEG amine (30 µmol) was added. The final reaction mixture was stirred for 10 hrs at room temperature. Solvents were removed on a rotavap and minimal methanol was added to dissolve the oily residue. The methanol solution was kept at −20° C. for 8 hrs and white precipitates were collected by centrifugation at −10° C. The crude intermediate was dissolved in 5 mL TFA-ITS-H$_2$O (95:2.5:2.5) and stirred for 3 hrs at RT to carry out the deprotection of the side chain and amine group of cysteine conjugated to PEG macromers. The solvent was removed and crude cysteine-terminated 4-armed PEG was purified by preparative reversed phase high performance liquid chromatography (RP-HPLC).

Similarly, to make thioester terminated 4-armed PEG, equal equivalents of EMPSA, PyBop and NMM were dissolved in DCM prior to addition of 0.2 equivalent of 4-armed PEG amine. The reaction mixture was stirred for 12 hrs and the solvent was removed on a rotavap to give a pale-yellow oily residue. Minimal amount of methanol was added to dissolve the residue and the solution was kept at −20° C. for 2 hrs and white precipitates were collected by centrifugation at −10° C. The crude thioester-terminated 4-armed PEG was purified by preparative RP-HPLC.

A solution of Boc-Cys(Trt)-OH, or protected dipeptides Boc-Cys(Trt)-AA-OH (0.25 mmol), in DCM (2 ml) was added into a vial containing PEG4A (0.5 g, 0.2 mmol of amino group) and BOP (0.11 g, 0.25 mmol), followed by addition of DIEA (44 µl, 0.25 mmol). The mixture was vortexed for 5 min, subsequently rocked for 2 hrs, and concentrated under N$_2$ flow. The residue was dissolved in 50 ml of MeOH, and frozen at −20° C. The precipitate was collected by centrifugation (−9° C., 6000 rpm, 20 min) and decanting the solvent. The purification cycle of four steps of dissolution in MeOH at room temperature, freeze at −20° C., centrifugation at −9° C. and decanting the MeOH was repeated for four times, and followed by precipitation with diethyl ether and dried in vacuo. The analysis of the products by silica gel TLC (solvent system DCM-MeOH—HOAc=100:3:1) gave single spot on the origin and no spot from Boc-Cys(Trt)-OH, or protected dipeptides. The ninhydrin test of the purified product gave a yellowish solution. Proton NMR (CDCl$_3$, 500 MHz) spectra of the protected cysteine-PEG4A conjugates confirmed their structures.

Protected cysteine-PEG4A conjugates were then treated with 30 ml of TFA containing TIS (1 ml) and EDT (1 ml) at room temperature for 2 hr, and concentrated under reduced pressure, respectively. The residue was dissolved in 50 ml of MeOH, and frozen at −20° C. The precipitate was collected by centrifugation (−9° C., 6000 rpm, 20 min) and decanting the solvent. The purification cycle of four steps of dissolution in MeOH at room temperature, freeze at −20° C., centrifugation at −9° C. and decanting the MeOH was repeated for four times, and followed by precipitation with diethyl ether and dried in vacuo to generate the conjugates 2, 3a-e TFA salt. Ninhydrin test gave a dark blue color, indicating that the Boc protection group was removed. Finally, the conjugates 2, 3a-e TFA salt was dissolved in 0.1 M NH$_4$HCO$_3$ aqueous solution (25 ml) bubbled with argon for 20 min, frozen at −20° C., and lyophilized to produce the salt-free conjugates 2, 3a-e.

D. Synthesis of Protected Peptide Fragments

Figure 4:
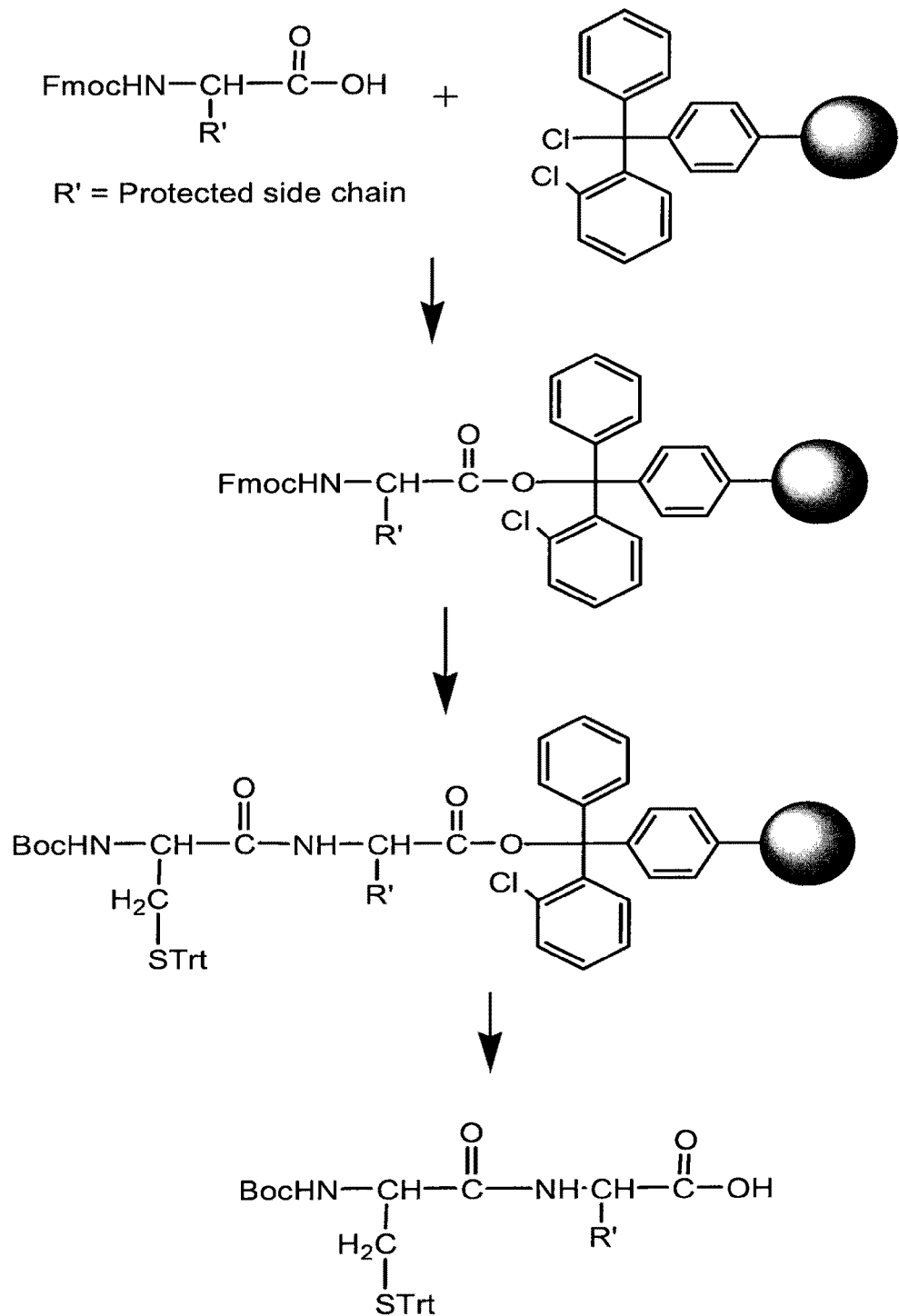
FIG. 4. Synthesis of Protected Cysteine dipeptides.
Figure 5:
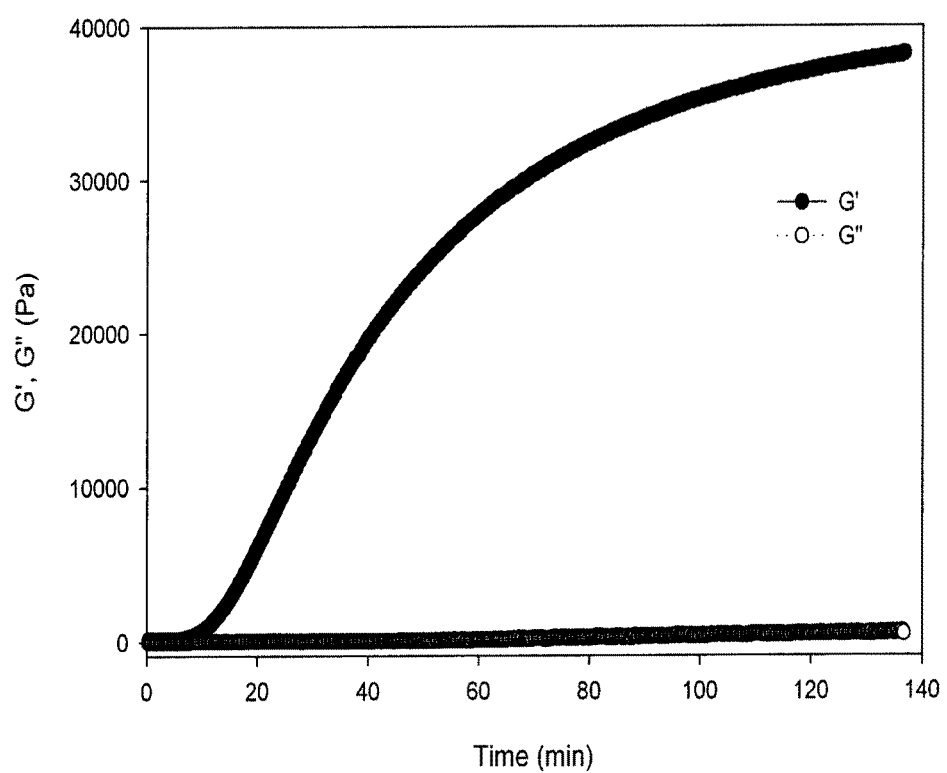
FIG. 5. Oscillatory rheology of hydrogel formation by NCL. Time test was performed at a constant oscillation frequency of 1 Hz and constant strain of 1%, at a controlled temperature (20° C.) by mixing 1 (20%, w/v) and 3b (20%, w/v).
Figure 6:
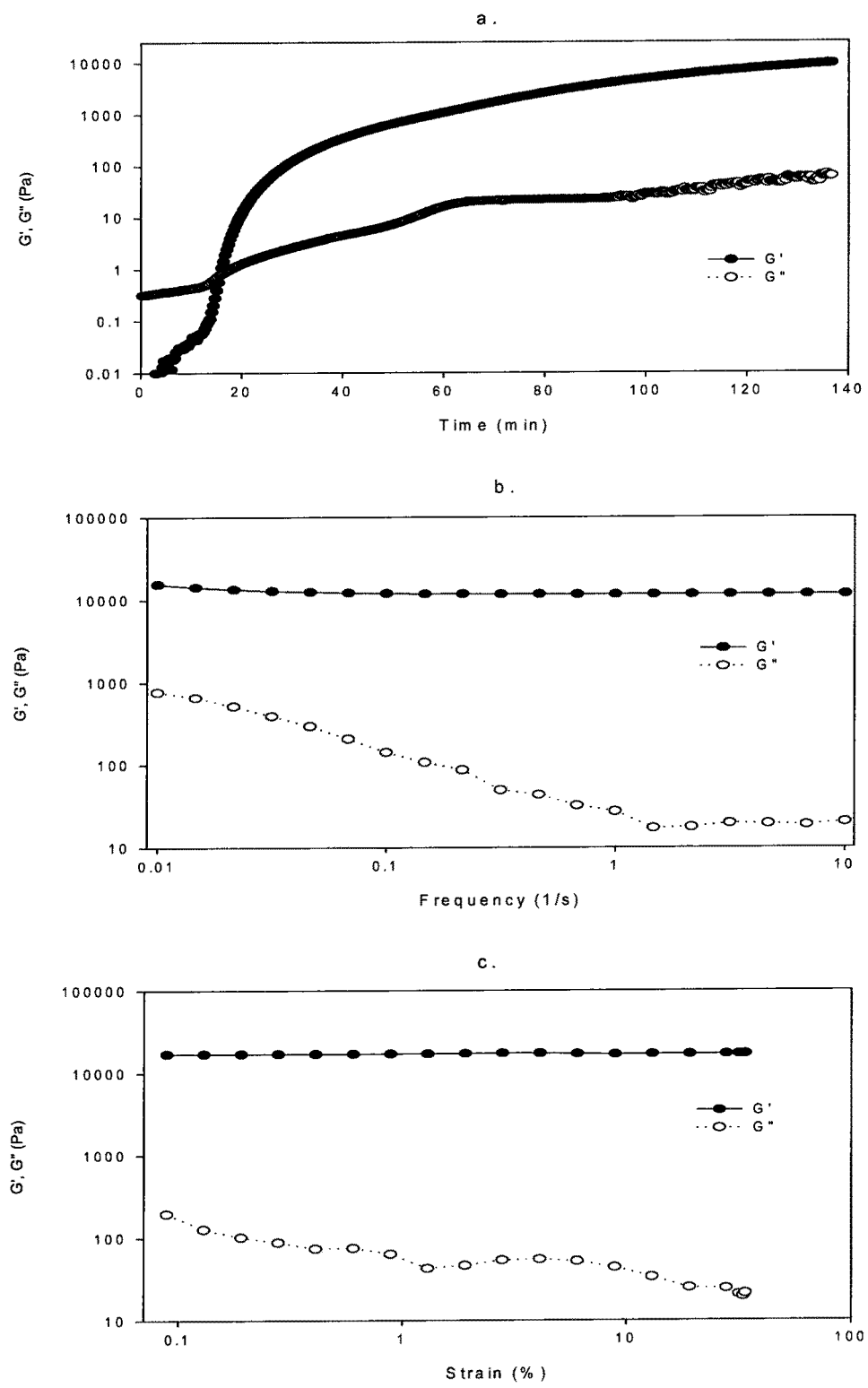
FIG. 6. Oscillatory rheology of hydrogel formed by mixing 20% EMPSA-PEG4A 1 and 20% Cys-Asp-PEG4A 3c in 100 mM $NH_4HCO_3$, pH 8.3. a. storage modulus versus time during crosslinking; b. frequency sweep at 1% strain after 60 minutes crosslinking at 20° C.; c. strain sweep at 1 Hz frequency after frequency sweep experiment. G'=storage modulus; G"=loss modulus.
Figure 7:
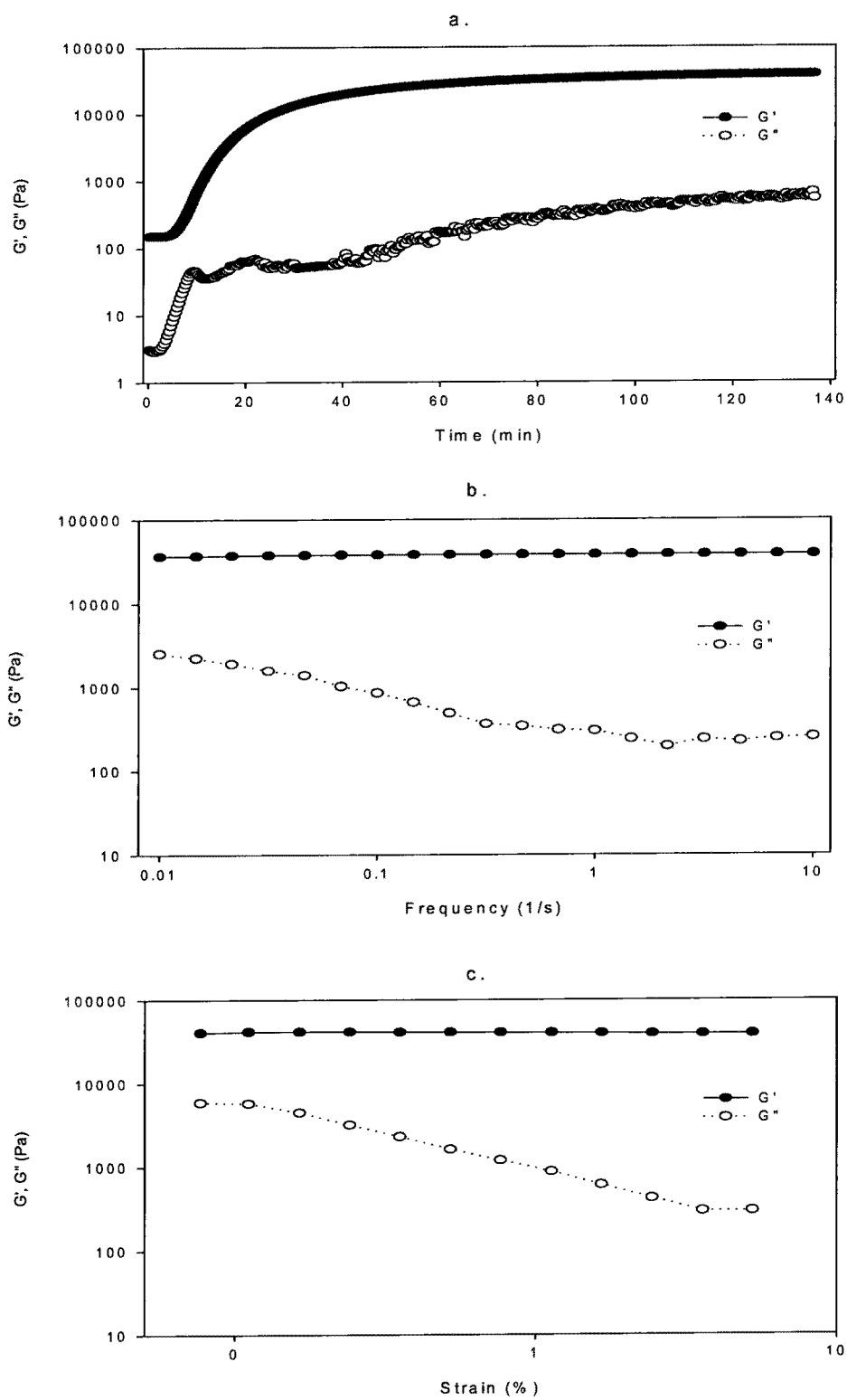
FIG. 7. Oscillatory rheology of hydrogel formed by mixing 20% EMPSA-PEG4A 1 and 20% Cys-Asp-PEG4A 3b in 100 mM $NH_4HCO_3$, pH 8.3. a. storage modulus versus time during crosslinking; b. frequency sweep at 1% strain after 60 minutes crosslinking at 20° C.; c. strain sweep at 1 Hz frequency after frequency sweep experiment. G'=storage modulus; G"=loss modulus.

Fully protected dipeptide Boc-Cys(Trt)-Gly-OH, Boc-Cys(Trt)-Glu(OtBu)-OH, Boc-Cys(Trt)-Asp(OtBu)-OH, Boc-Cys(Trt)-Trp(Boc)-OH, Boc-Cys(Trt)-Arg(Pbf)-OH were synthesized manually as protected peptide fragments by Fmoc strategy on a 2-chlorotrityl chloride resin (FIG. 4). A typical procedure of solid-phase synthesis was performed with 2-chlorotrityl chloride resin (1.0 g, 1.55 mmol/g). The solution of Fmoc-amino acid-OH (1 mmol) dissolved in DCM (10 mL) and DIEA (1 mL) was added to a reaction vessel containing 1.0 g of 2-chlorotrityl chloride resin (1.55 mmol) and rocked for 30 min, followed by washing with DMF three times. The resin was treated with DCM-MeOH-DIEA (8:1:1) for 20 min. and washed with DMF three times. Fmoc was removed by treatment with 20% piperidine in DMF for 20 min and washed with DMF four times. The ninhydrin test of the resin showed positive result. Boc-Cys(Trt)-OH (0.92 g, 2 mmol) and BOP (0.88 g, 2 mmol) were dissolved in DCM (8 mL), followed by addition of DIEA (522 µL, 3 mmol). After 10 min, the solution was added to the resin and rocked for 2 hrs, followed by washing with DMF and MeOH, three times each. The resin was dried in vacuo and ninhydrin test of the resin gave a yellowish color. Then, protected peptide fragments were obtained by treatment of the resin with 1% TFA in dichloromethane (DCM), and the cleaved peptide sequences were confirmed by MALDI TOF-MS analysis. The analysis of the products by silica gel TLC (solvent system DCM-MeOH—HOAc=100:3:1) gave single spot on the plate.

E. Synthesis of Peptides for Functionalizing Hydrogels

Figure 10:
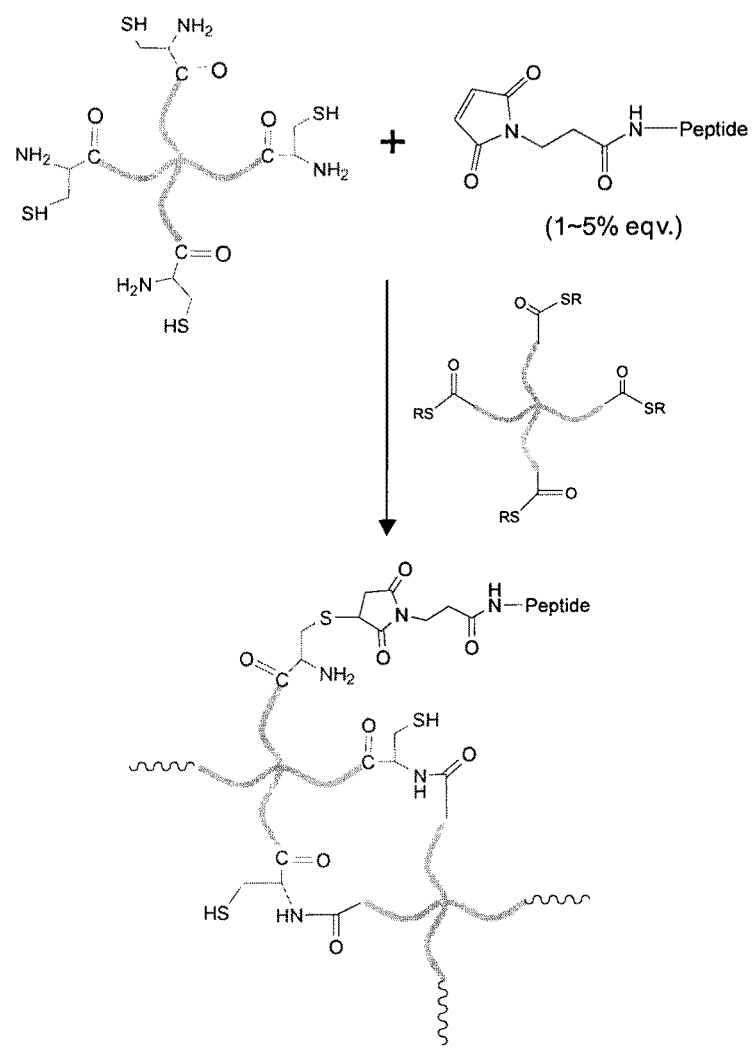
FIG. 10. Presence of functional peptides on hydrogels formed by native chemical ligation. Prior to mixing 4-armed PEG-Cys (A) and 4-armed PEG-ThE (B) to form hydrogel, maleimide-terminated peptides are used to modify 1~5% cysteine groups of PEG-Cys. The finally resulted hydrogel presents peptides at defined densities.

Maleimide-terminated peptides MA-GRGDSPG-NH$_2$ (SEQ ID NO: 1) and MA-OEG$_2$-FEWTPGWYQPY-NH$_2$ (SEQ ID NO: 2) were synthesized using standard solid phase peptide synthesis protocols on Rink amide resin (0.69 meq/g)

at 0.1 mmol scale (FIG. 10). Each coupling step was carried out by mixing 3 equivalents of Fmoc protected amino acids, PyBop and NMM with the resin beads for 4 hours on a rocker. After the resin beads were washed thoroughly with DMF, 20% piperidine in DMF was used to deprotect Fmoc group to expose the amine groups on the beads for next coupling step. After the last amino acid was conjugated, maleimide-OSU ester (2 eqv.) in DMF was used to attach the maleimide moieties to the N-terminal of resin-bound peptides. Cleavage of the maleimide-terminated peptides from the resin and deprotection of the amino acid side chains was accomplished by treating the resin with 95% (v/v) TFA, 2.5% H2O and 2.5% TIS for 2 hours at room temperature, after Which the cleaved peptides were collected by filtering and rinsing resins several times with TFA. Solvent was removed using a rotary evaporator; the product residues were dissolved in a minimal amount of TFA and precipitated with cold ether and by centrifugation at 4° C. The product pellets were dissolved in deionized water, frozen and lyophilized. Crude products were purified by preparative RP-HPLC.

Synthesis of Biocompatible Hydrogels

A. Methods and Materials.

4-armed PEG with amine end groups ($\overline{M}_w$=10 k) (PEG4A) was purchased from SunBio PEG Shop. 3-Mercaptopropionic acid ethyl ester was purchased from TCI America (Portland, Oreg.). 2-ClTrt chloride resin (1.55 mmol/g), BOP and HOBt were purchased from Peptide International (Louisville, Ky.). Protected amino acids were purchased from NovaBiochem (La Jolla, Calif.). Acetonitrile and MeOH were from Burdick and Jackson. TFA and ether were from J. T. Baker. Succinic anhydride, DMF, DIEA, piperidine, DMAP, ninhydrin and tris(2-carboxyethyl) phosphine hydrochloride (TCEP) were purchased from Aldrich Chemical Company (Milwaukee, Wis.).

B. Gel Formation.

In this example, the inventors evaluated gel formation of the hydrogels by mixing thioester-polymer bioconjugate 1 in pure water (solution A) and one of the N-terminal cysteine-polymer bioconjugates 2, 3a-e in a buffer solution (solution B). Hydrogels were formed by adding solution B into a test tube (100×13 mm) containing solution A and a moving stirring bar (10×3 mm). Unless otherwise indicated, the mixtures were equimolar in thioester-polymer and N-terminal cysteine-polymer. Using a stopwatch, the gel formation time was recorded when movement of the stir bar stopped as a result of gel formation.

TABLE 1

Effect of polymer concentration, stoichiometry, buffer and temperature on gel formation of 1 and 2 by NCL.

| Test | $C^1$ | Buffer system | $R^2$ | T (° C.) | Gelation time |
|---|---|---|---|---|---|
| 1 | 2 | GIBCO PBS | 1:1 | 23 | 3 days |
| 2 | 5 | 0.1 M PBS, pH 7.6 | 1:1 | 23 | 2 hrs |
| 3 | 5 | 0.1 M PBS, pH 7.6 | 1:2 | 23 | 2 hrs |
| 4 | 5 | 0.1 M Phosphate, pH 7.6 | 1:1 | 23 | 2 hrs |
| 5 | 5 | 0.1 M Phosphate, pH 7.6 | 1:2 | 23 | 2 hrs |
| 6 | 20 | 0.1 M PBS, pH 7.6 | 1:1 | 37 | 25 min |
| 7 | 20 | 0.1 M PBS, pH 7.6 | 1:1 | 23 | 35 min |
| 8 | 20 | 50 mM Tris buffer, pH 8.2 | 1:1 | 23 | >60 min |
| 9 | 20 | 50 mM Tris buffer, pH 8.2 | 1:1 | 37 | >60 min |
| 10 | 20 | 0.1 M NaHCO$_3$, pH 8.3 | 1:1 | 23 | 15 min |
| 11 | 20 | 0.1 M NaHCO$_3$, pH 8.3 | 1:1 | 37 | 6 min |

[1]Total polymer concentration (%, w/v).
[2]Molecular ratio of 1 to 2 (TFA salt of 2 was used throughout).

C. Effect of Buffer System, Bioconjugate Concentration and Temperature

In this example, the inventors optimized the conditions for hydrogel formation by investigating a limited number of combinations of buffer system, bioconjugate concentration and temperature using thioester-polymer 1 and the TFA salt of N-terminal cysteine-polymer 2. The results showed that the hydrogel formation time was significantly affected by buffer system, bioconjugate concentration and reaction temperature (Table 1). Among the conditions tested, the hydrogel formed fastest (~6 min) at a total polymer concentration of 20% (w/v) in 0.1 M sodium bicarbonate buffer pH 8.3 at 37° C. In a control experiment, 20% of cysteine-polymer bioconjugate 2 in sodium bicarbonate buffer pH 8.3 became a viscous solution within three hours and a gel overnight at room temperature. However, the gel of 2 was readily soluble after addition of equal volume of 20 mM tricarboxyethylphosphine (TCEP) in water or 100 mM 2-mercaptoethanol in water, suggesting gelation via disulfide bond formation. In contrast, the hydrogel resulting from mixing 1 and 2 had a pH value ~7 and was stable after addition of an equal volume of 20 mM TCEP in water or 100 mM 2-mercaptoethanol in water. From this result it can be concluded that after mixing solutions of 1 and 2, the hydrogel was formed mainly by cross-linking through NCL rather than through disulfide bond formation.

D. Effects of pH and Bioconjugate Composition

In this example, the inventors optimized the conditions for hydrogel formation by investigating a limited number of combinations of pH and polymer bioconjugate chemical composition. Twenty percent of thioester-polymer 1 was mixed in water with twenty percent N-terminal cysteine-polymer bioconjugates 2, 3a-e (in either TFA salt or salt-free form) dissolved in sodium bicarbonate buffer (Table 2). All hydrogels derived from the salt-free bioconjugates 2, 3a-e had higher measured pH values (~8) and lower gel times compared to their corresponding TFA salt bioconjugates, demonstrating that pH value within the same buffer system can have a significant influence on the gel time.

With respect to the composition of the N-terminal cysteine-polymer, the similar gel formation times for 2 and 3a indicated that insertion of a neighboring Gly residue between the N-terminal Cys and the polymer had little effect on the reactivity of the cysteine. Similarly, insertion of a basic residue (Arg, 3e) between the N-terminal Cys and the polymer also had little effect on gel time. However, a neighboring Trp residue with an aromatic indole side-chain group resulted in significantly slower hydrogel formation although the presence of a flanking Trp residue increased the tendency of the N-terminal Cys residue to undergo rapid disulfide bond formation upon dissolution in buffer (test 5, Table 2). This interpretation is supported by lack of immediate disulfide gel formation and slow NCL gel formation in the presence of TCEP and/or 2-mercaptoethanol (tests 6 and 7, Table 2). Surprisingly, two acidic amino acid residues were found to have opposite effects on gel time. A neighboring Glu residue had a mild accelerating effect on NCL gel formation whereas an Asp residue in the same location nearly doubled the gel time.

TABLE 2

Gel formation for equimolar mixtures of 1 with different N-terminal cysteine-polymers*

| Test | N-terminal cysteine-polymer | $GT^1$ | $GT^2$ |
|---|---|---|---|
| 1 | Cys-PEG4A, 2 | 5'30" | 3'47" |
| 2 | Cys-Gly-PEG4A, 3a | 5'40" | 3'42" |
| 3 | Cys-Glu-PEG4A, 3b | 4'40" | 3'30" |
| 4 | Cys-Asp-PEG4A, 3c | 7'20" | 6'34" |
| 5 | Cys-Trp-PEG4A, 3d | 8'05" | Gel[3] |

TABLE 2-continued

Gel formation for equimolar mixtures of 1 with different N-terminal cysteine-polymers*

| Test | N-terminal cysteine-polymer | GT[1] | GT[2] |
|------|-----------------------------|-------|-------|
| 6 | Cys-Trp-PEG4A, 3d | | 9'43"[4] |
| 7 | Cys-Trp-PEG4A, 3d | | 11'41"[5] |
| 8 | Cys-Arg-PEG4A, 3e | n/d | 3'38" |

*20% 1 in $H_2O$ and 20% N-terminal cysteine-polymer (2, 3a-e) in 0.2 M $NaHCO_3$ pH 8.3 at 37° C.
[1]Gelation time with TFA salt of N-terminal cysteine-polymer.
[2]Gelation time with salt-free N-terminal cysteine-polymer.
[3]Salt-free N-terminal cysteine-polymer gelled immediately after addition of $H_2O$ and vortex.
[4]Salt-free N-terminal cysteine-polymer was dissolved in 20 mM TCEP aqueous solution and 1 in 0.2M $NaHCO_3$.
[5]Salt-free N-terminal cysteine-polymer was dissolved in 200 mM 2-mercaptoethanol aqueous solution and 1 in 0.2M $NaHCO_3$.
n/d: not determined.

E. Viscoelastic Behavior of Hydrogels

To characterize the viscoelastic behavior of the hydrogels formed by NCL, two hydrogel systems (1/3b and 1/3c) were chosen based on preliminary gelation experiments and analyzed further by oscillatory rheology. Oscillatory rheological experiments were performed with a Paar Physica MCR300 Rheometer with a Peltier device to control temperature at 20° C. using a stainless steel cone/plate fixture (50 mm in diameter, 1° cone). In a typical experiment, the bioconjugate solutions were prepared as follows: Solution A 10% or 20% of EMPSA-PEG4A 1 in water and Solution B 20% of salt-free 3c, or 10% and 20% of salt-free 3b in 0.2 M $NH_4HCO_3$ aqueous solution, pH 8.3. 500 µl each of solution A and solution B were added into a vial. After vortexing, 590 µl of the solution was immediately loaded onto the thermostated rheometer plate (20° C.), and the top cone (50 mm in diameter, 1° cone) was positioned to hold the solution in a 0.05 mm gap at the center between the cone and plate. After moisturized Kimwipes paper was applied to surround the cone/plate fixture for evaporation control, data were collected every 20 s over 140 min. The time dependence of the viscoelastic behavior measured at a constant oscillation frequency of 1 Hz and constant strain of 1%, at a controlled temperature (20° C.). The time dependent changes in storage modulus (G') and loss modulus (G") for all NCL hydrogels tested were characteristic of elastic hydrogel formation (FIGS. 5-6) as indicated by a low initial G', a G'/G" crossover point representing a theoretical gel condition, followed by rapid increase in G' to a plateau value as the NCL reaction becomes complete (Kavanagh, 1998; Ross-Murphy, 1994).

Figure 8:
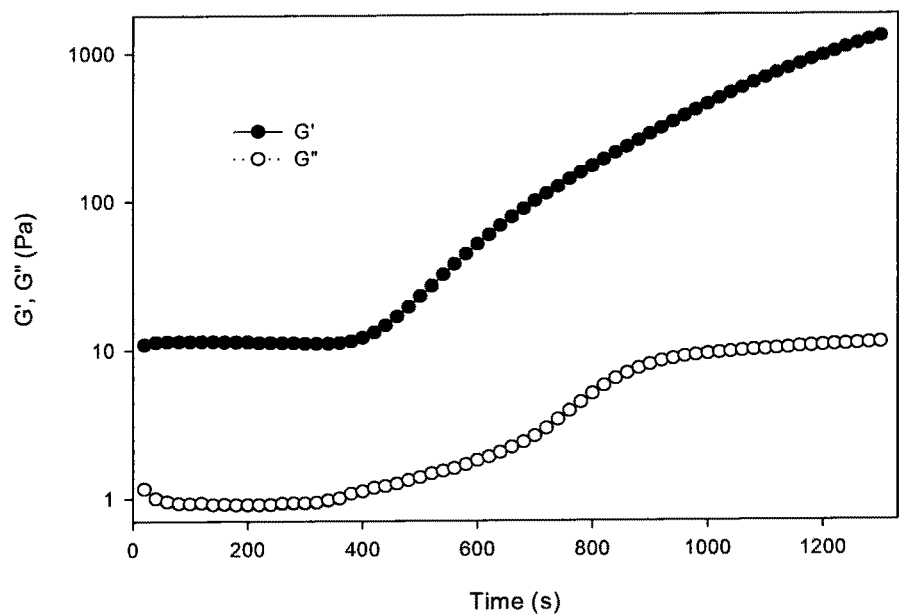
FIG. 8. Oscillatory rheology of hydrogel formed by mixing 10% EMPSA-PEG4A 1 and 10% Cys-Asp-PEG4A 3b in 100 mM $NH_4HCO_3$, pH 8.3. storage modulus versus time during crosslinking; G'=storage modulus; G"=loss modulus.
Figure 9:
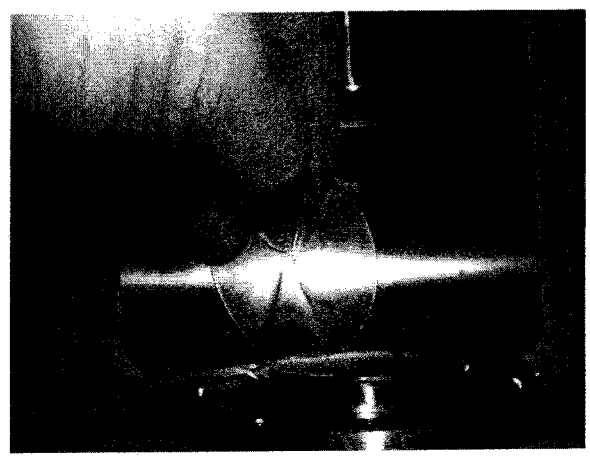
FIG. 9. Picture of hydrogel formed by mixing 20% EMPSA-PEG4A 1 and 20% Cys-Asp-PEG4A 3b in 100 mM $NH_4HCO_3$, pH 8.3 after oscillatory rheology.

For the mixture of 1 and 3c the characteristic crossover point was reached after 10 min however for the mixture of 1 and 3b gel formation was so rapid that the crossover point was missed when the rheological measurements started (G'>G") (FIG. 7), as was the case even when the polymer concentration was decreased to 10% (FIG. 8). The difference in observed rheological gel time between NCL hydrogels formed from 3b and 3c is consistent with the results reported in Table 2. The stiffness of the fully cured NCL hydrogels was remarkably high as illustrated by a plateau modulus value of nearly 40 kPa for the mixture of 1 and 3b (FIG. 9). The measurements of the storage modulus and loss modulus were taken at 20° C. in the oscillatory mode at 1 Hz frequency and 1% strain during crosslinking (FIGS. 6a-8a). After the gelation experiment, a frequency sweep experiment was performed from 0.01 Hz to 10 Hz with 19 data points at 1% strain (FIGS. 6b-7b). Finally, a strain sweep experiment was performed with strain from 1% to 100% at 1 Hz frequency (FIGS. 6c-7c).

Methods of Use

A. MIN 6 Cell Encapsulation in Hydrogels Formed by NCL

Mouse insolinoma cell line MIN 6 was a gift from Dr. Dixon Kaufman's lab in the Department of Surgery at Northwestern University. Cells were cultured in the DMEM medium containing 15% FBS, penicillin, strepmycin and 50 µM MCE at 37° C. under 5% $CO_2$. Cells between passage number 25 and 28 were used for all the studies in this work.

Prior to cell encapsulation, cells were detached from tissue culture plates with a 0.25% trypsin-EDTA solution and resuspended in DMEM at a cell density of $4 \times 10^5$/mL. 20 µL solution of 4A-PEG-Cys in DMEM (pH 7.4, w/v 10%) was added to a mini-dialysis tube immersed in 1 mL DMEM, then 40 ul of the cell suspension was then added to the tube followed by addition of 20μl solution of 4A-PEG-ThE in DMEM (pH 7, w/v 10%) lastly.

To form hydrogels presenting functional peptides, maleimide-terminated peptides were added to the solution of PEG-Cys at a molar ratio of 1:25 (MA-peptide: PEG-Cys) prior to mixing cells with PEG-Cys and PEG-ThE. The mixture was incubated at 37° C. for 30 minutes to form hydrogel disks (8 mm O.D.×1 mm thick) were formed with cells embedded in. These hydrogel disks were rinsed 3 times by incubating the gels in fresh DMEM for 5 minutes each time and then immersed in the cell growth medium for culture at 37° C. under 5% $CO_2$. Culture medium was changed every 2 days.

B. Immunoisolation of Encapsulated MIN 6 Cells from T-Lymphocytes

The immunoisolating property of the hydrogels provided herein was tested by measuring cell viability upon co-culture with β-cell-specific cytotoxic T-lymphocytes. Transgenic T-lymphocytes were cultured and activated in 96-well plates in Dr. Xunrong Luo's lab following previously reported protocols. The T-cells were harvested by centrifugation to remove the culture media and resuspended in DMEM containing 15% FBS at a density of $10^6$ cells/mL. Hydrogels containing encapsulated MIN 6 cells were immersed in such T-cell suspension under gentle shaking for 24 hours. The hydrogels were removed and washed with fresh MIN 6 cell culture media followed by cell viability assay. For comparison, MIN 6 cells from regular cell culture were incubated with T-cell suspension for 24 hours. The media containing floating T-cells were removed and fresh culture media were used to wash the MIN 6 cells followed by cell viability assay.

C. Inhibitory Effects of Hydrogels on MIN 6 Cell Death Induced by Cytokines

Figure 11:
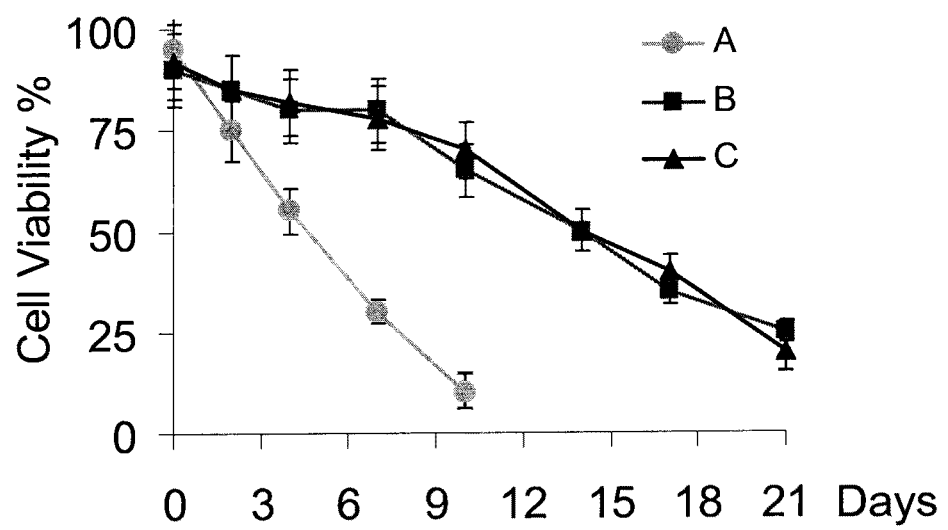
FIG. 11. Viability of MIN 6 cells encapsulated in hydrogels crosslinked by native chemical ligation. (A) non-modified hydrogel (B) 1% GRGDSPG modified hydrogel (C) hydrogel modified with 1% GRGDSPG and 1% IL-1RIP.

MIN 6 cells were encapsulated in non-modified or peptide-functionalized hydrogel disks as described above and cultured for 48 hours. Cell culture media was changed to serum-free DMEM (containing 1% FBS) and cells were equilibrated at 37° C. and 5% $CO_2$ for 30 minutes. Cytokine-containing medium was prepared with IL-1β (5 ng/ml), TNF-α (10 ng/ml) and INF-γ (25 ng/ml) in serum-free DMEM. The encapsulated cells were treated with such media at 37° C. for 2 hours and rinsed with serum-free DMEM followed by cell viability assay (FIG. 11).

D. Live/Dead Assays on Free and Encapsulated MIN 6 Cells

Figure 12:
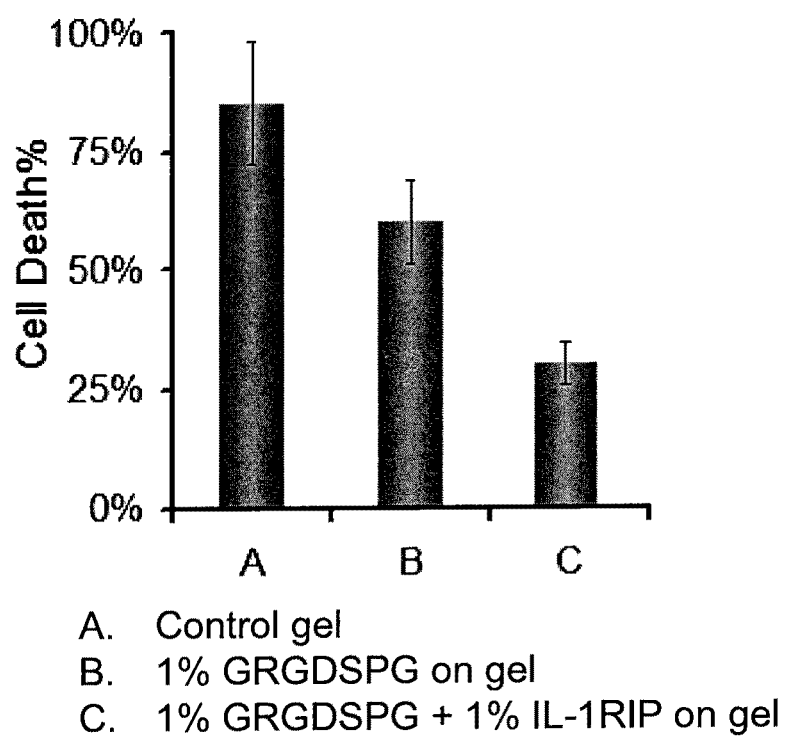
FIG. 12. Peptide-functionalized hydrogels protect MIN 6 cells from cytokine-induced cell death. 24 hours after encapsulation, cells were treated with a combination of IL-1β (5 ng/ml), TNF-α (10 ng/ml) and INF-γ (25 ng/ml) in serum-free DMEM for 1 hour. Fluorescent cell viability assay (calcein-AM for live and ethidium homodimer-1 for dead cells) was used to determine the amount of cell death.

MIN 6 cells cultured on tissue culture plates or encapsulated cells in hydrogel disks were incubated with a PBS solution containing calcein-AM (1 µM) and ethidium homodimer-1 (1 µM) for 30 minutes at 37° C. The cells were rinsed with PBS and imaged on an inverted fluorescence microscope. Cell viability was determined as the ratio of the number of live cells divided by the total number of live and dead cells (FIG. 12).

Encapsulation of Pancreatic Islets

A. Background

Islet transplantation is a very attractive option for restoring glycemic control in patients because it does not require major surgery and enables the potential storage of donor cells by cyropreservation. However, the major obstacles to islet transplantation are the availability of islets and the maintenance of islet functions. Islet encapsulation uses an immuno-protective biomaterial to create a perm-selective membrane around a group of islet cells, enabling islet transplantation in the absence of immunosuppression. Yet, encapsulated islet graft survival and function are still limited due to a lack of material biocompatibility, inefficient immunoprotection from small inflammatory factors and hypoxia.

Successful transplantation of pancreatic tissue has been demonstrated to be an efficient method of restoring glycemic control in type I diabetic patients. Pancreatic islet transplantation has been a very attractive method to restore glycemic control in type I diabetic patients. It does not require major surgery, but only a small implantation procedure with which an islet mass is delivered to the liver by intrapotal infusion. Islet tissue also has the advantage that it may be modulated prior to implantation to reduce the risk of rejection. However, as encountered in whole pancreas transplantation, the major obstacles for pancreatic islet transplantation include the requirement of immunosuppressive drugs to establish graft acceptance as well as the worldwide shortage of organ donors.

Encapsulation of pancreatic islets in semi-permeable materials has been investigated for islet transplantation in the absence of immunosuppressants. The immunoisolating materials around islet tissue can provide a protective barrier in order to allow allo- or xenotransplantation, which will presumably resolve the shortage of organ source. Numbers of natural and synthetic polymers have been applied to islet encapsulation and normoglycemia can be achieved in rodent and canine models and more recently, in humans. However, islet graft survival was always of limited duration. Graft failure is usually attributed to the following factors: (1) insufficient biocompatibility of materials used for encapsulation. For example, many studies have shown that purity and composition of alginate, a mostly widely-used material for islet encapsulation, substantially affect the survival of trapped islets. (2) Hypoxia, a problem due to the lack of vasculature recovery within/around the islets causing the limited supply of oxygen and nutrients to encapsulated cells. Materials with poor biocompatibility tend to attract nonspecific adsorption of protein and cells (fibroblast overgrowth) on the exterior of the capsules, which also largely reduces the exchange between the encapsulated islets and surroundings. Non-immunogenic and inert synthetic biomaterials seem to be better choices compared to natural materials. (3) Incomplete immunoprotection from small molecule cytokines and radicals. Capsule permeability desired for islet encapsulation should block the entry of large cells and antibodies (MW>75 KD) of the immune system but still allow the diffusion of nutrients and metabolic waste for cell growth to get into the capsules as well as insulin secreted from cells to get out of capsules. However, pro-inflammatory cytokines of low molecular weight such as IL-1β (17.5 KD) and TNF-α ((51 KD) can still get into the capsules and exert deleterious effects on β-cell function and vitality.

In this work, the inventors demonstrate the use of a novel hydrogel system for the encapsulation of islet cells. The hydrogels according to Formula IV are crosslinked in situ through native chemical ligation upon mixing cystine-terminated and thioester-terminated 4-armed PEG under physiological conditions. Such biocompatible hydrogels efficiently isolate encapsulated islet cells from immunocytes and allows straightforward attachment of bioactive molecules for modifying microenvironment around the trapped islet cells for improvement of cell survival and function. In particular, presence of a cytokine-inhibitory peptide on the hydrogel further protects the cells from damage induced by pro-inflammatory cytokines that are presumably permeable through the capsules, providing the resolution to the incomplete immunoprotection encountered in conventional islet encapsulation studies. The approach of using biocompatible material with anti-inflammatory properties is widely applicable in many other tissue/cell transplantation practices.

B. Materials 4-armed PEG amine (MW 10 KD) was purchased from Sunbio (Korea). Rink amide resin, PyBop and Fmoc protected amino acids were purchased from Novabiochem and Anaspec (San Diego, Calif.). 2-Ethylpropriate thiol from TCI (Canada). Maleimide-OSU active ester was purchased from TRC (Canada). Dichloromethane (DCM), dimethylformamide (DMF), acetonitrile (ACN), diethyl ether, N-methylmorphiline (NMM), methanol, piperidine, 2-mercaptoethanol (NICE), trifluoroacetic acid (TFA), triisopropylsilane (TIS) and α-cyano-4-hydroxycinnamic acid (CHCA) matrix were purchased from Sigma-Aldrich (Milwaukee, Wis., USA). Calcein-AM, and ethidium homodimer-1 were purchased from Molecular Probes (Eugene, Oreg., USA). Dulbecco's modified Eagle's medium, fetal bovine serum, penicillin/streptomycin, typsin-EDTA were obtained from American Type Culture Collection (Manassas, Va., USA). Transgenic T-lymphocytes was a gift from Dr. Xunrong Luo's lab in the Department of Surgery at Northwestern University.

C. Immunoprotecting β-cells

The ultimate goal of islet cell encapsulation in hydrogels is to provide islet transplants a protective barrier from the host immunorejection. Various hydrogels have been applied to isolate encapsulated islet cells from immunoreactive T-cells and high MW antibodies (MW≥75 KD), however, such immunoprotection proved to be rather incomplete because low MW inflammatory factors are still able to freely diffuse into the hydrogel and damage the encapsulated cells. At the permeability of hydrogels desired for free diffusion of nutrients and cell metabolic waste through the hydrogels and of insulin secreted from encapsulated cells to outside of hydrogels, free entry of pro-inflammatory cytokines such as IL-β, TNF-α and IFN-γ can not be blocked because these molecules have lower molecular weights that the MW cutoff value. The pro-inflammatory cytokines are critical in causing early islet graft injury and thus such incomplete protection really limited the success of islet encapsulation in clinic applications.

In this work, the inventors provide highly localized protection to islet cell transplants from the damage caused by cytokines infiltrated into the hydrogel capsules. A peptide inhibitor for cell surface IL-1 receptor (IL-1R) was attached covalently to hydrogel in which cells were trapped and therefore can block the interaction between cells and cytokines diffused to the vicinity. Such anti-inflammatory effect is highly localized to the encapsulated cell transplant and thus avoids the harmful side-effects encountered during the use of conventional immunosuppressive drugs following transplantation.

The IL-1R inhibitory peptide sequence -FEWTPGW-YQPY-NH$_2$ (IL-1RIP) (SEQ ID NO: 2) was designed based on a previously reported inhibitory peptide for IL-1R. MIN 6 cells cultured on surfaces presenting this peptide showed significantly reduced apoptosis when treated with a combination of IL-β, TNF-α and IFN-γ (data not shown), indicating the immobilized format of peptide can maintain its anti-inflammatory property. The inventors then examined the protecting effect on encapsulated cells of this peptide immobilized on hydrogels. Maleimide-terminated IL-1RIP was attached to hydrogels using Michael Addition reaction as described previously with the ratio of peptide: cystine varying from 1:99 to 5:95. The hydrogel-cell system was then treated with a serum-free medium containing a combination of IL-β, TNF-α and IFN-γ.

Compared to non-modified hydrogel capsules, the IL-RIP-modified hydrogel was able to reduce the death of encapsulated MIN 6 cells by 60% as shown in FIG. 12. This survival-promoting effect could be sufficiently achieved at a density of peptide on hydrogel at as low as 1% of total thiol groups. The inventors' data also implies that presence of the adhesion peptide (GRGDSPG-NH$_2$) only also inhibited cell death to some extent but co-presence of the two peptides protected the cells from cytokine-induced death to a much higher level.

The immunoisolating property of the hydrogel network formed through NCL was also tested by co-culture of encapsulated MIN 6 cells in hydrogel disk with cytotoxic T-lymphocytes. Islet-specific CD4+ T-lymphocyte cells were collected from transgenic mice and activated using BDC peptide. Co-culture of these activated CD4+ T-cells with free MIN 6 cells resulted in cell death, while cells encapsulated in hydrogel disks showed dramatically increased survival when treated with T-cells (FIG. 12). This demonstrates that the hydrogel barrier could efficiently protect MIN 6 cells from infiltration and fatal attack of immunoreactive T-lymphocytes.

D. Insulin-Releasing in Peptide-Modified Hydrogels

The failure of islet grafts following transplantation is due to not only the degeneration of β-cells upon time, but also the loss of ability to secret insulin in response to blood glucose changes. An optimal material used to encapsulate islet cells should be able to maintain the glucose-stimulated insulin release function of β-cells.

Figure 13:
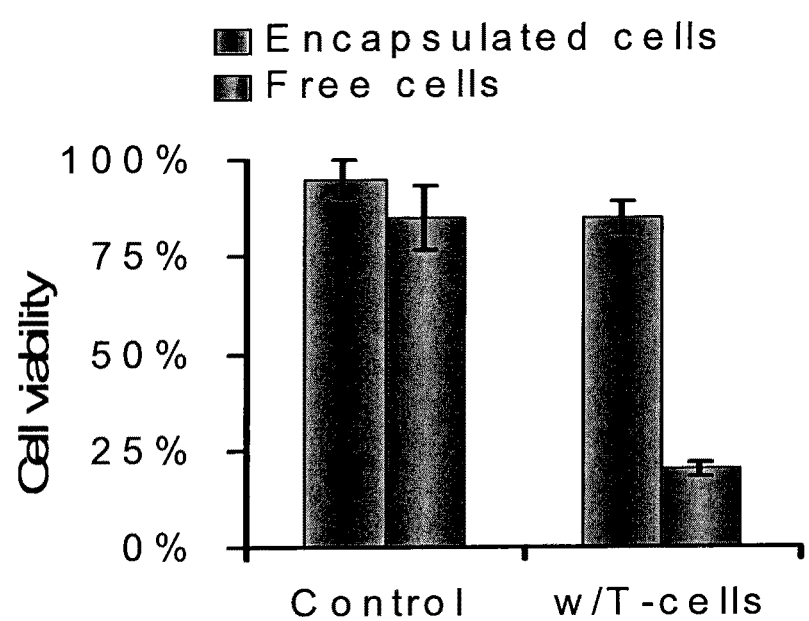
FIG. 13. Immunoisolation of MIN 6 cells from cytotoxic T-lymphocytes. Free MIN 6 cells and cells encapsulated in hydrogel capsules were co-cultured with β-cell specific CD4+ T-cells. Encapsulated MIN 6 cells had significantly increased viability compared to cells exposed freely to T-cells.
Figure 14:
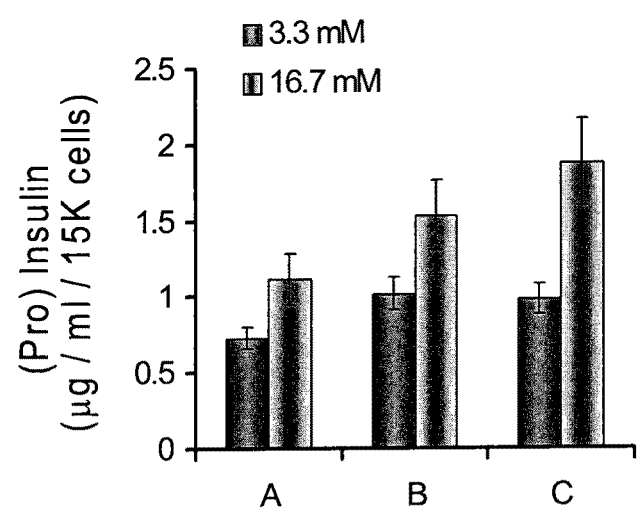
FIG. 14. Glucose-stimulated insulin release from encapsulated MIN 6 cells. Peptide-functionalized hydrogels did not affect the capability of cells to produce insulin in responsive to glucose concentration change from 3.3 mM to 16.7 mM; in particular, IL-1RIP peptide modified hydrogel increased the cell sensitivity for glucose stimulus.
Figure 15:
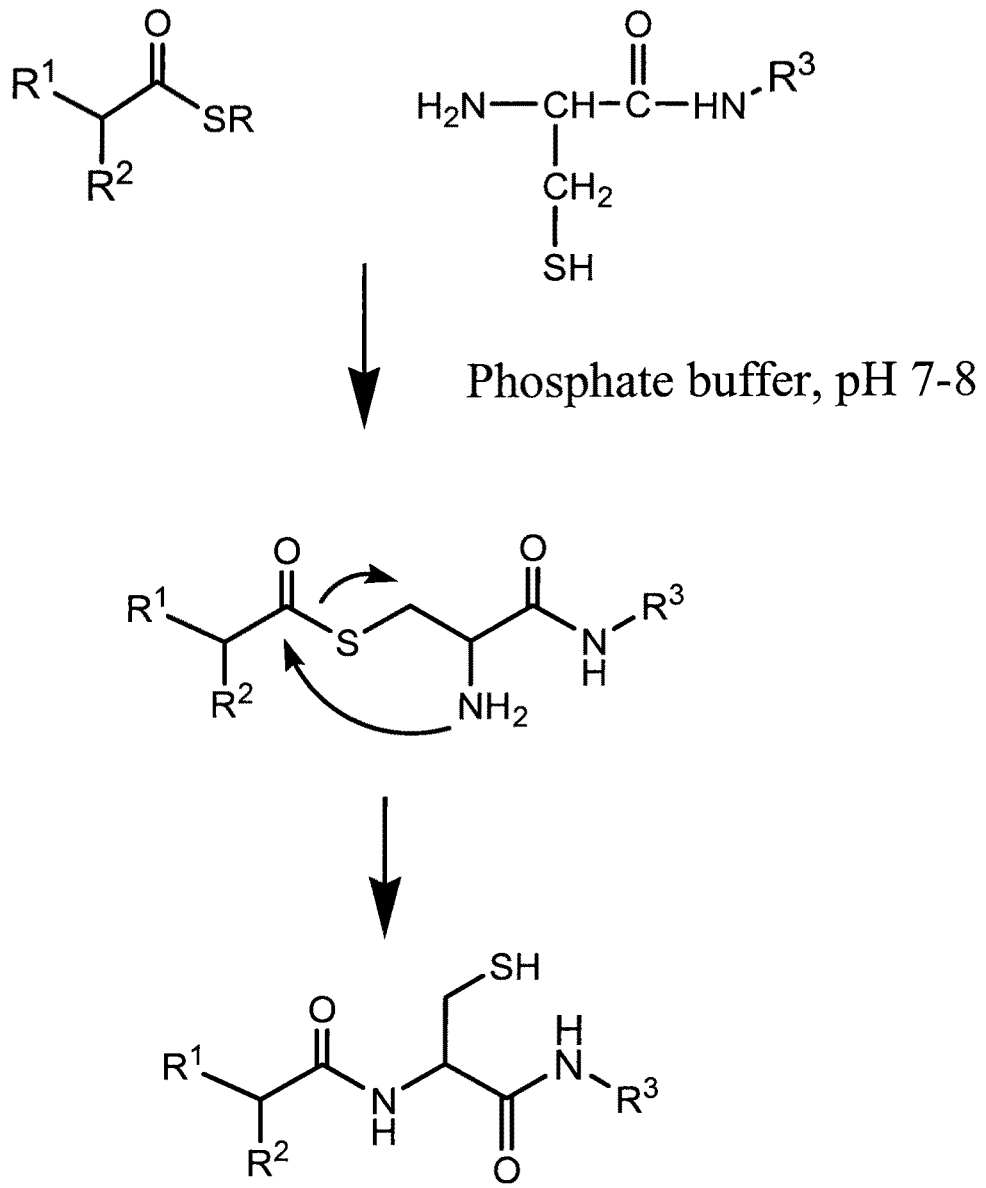
FIG. 15. Chemistry of Native Chemical Ligation.

The inventors examined the effects of the NCL hydrogel network on the insulin secretion from encapsulated MIN 6 cells. As FIG. 13 shows, MIN 6 cells trapped in hydrogel disks maintained their ability to release insulin responsive to the glucose challenge in the media from 3.3 mM to 16.7 mM. In particular compared to non-modified and GRGDSPG-modified gels, the presence of IL-1RIP on hydrogels seemed to sensitize the glucose-stimulated insulin secretion capability of encapsulated cells. (The inventors also observed the same property of soluble IL-RIP on MIN 6 insulin secretion. This property of IL-1 RIP has not been previously reported, the mechanism underneath is worth investigation.)

It should be noted that the above description, attached figures and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

REFERENCES

Akeson, et al., J. Biol. Chem., 1996, 271, 30517.
Ammon, et al., Biomaterials 2007, 28 (19), 3004-3011
Arnush, et al., J. Clin. Invest. 1998, 102(3), 516.
Barshes, et al., J. Leuk. Bio. 2005, 77, 587.
Bang, et al., Angew. Chem. Int. Edit. 2006, 45, 3985-3988.
Beck, et al., Nguyen Tissue Eng. 2007, 13, 589.
Bernkop-Schnurch, et al., J. Control. Release 2003, 93, 95-103.
Collier, et al., J. Am. Chem. Soc. 2001, 123, 9463-9464.
Cushing, et al., Science 2007, 316, 1133-1134.
Dawson, et al., Science 1994, 266, 776-779.
Dawson, et al., Annu. Rev. Biochem. 2000, 69, 923-960.
De Groot, et al., J. Surg. Res., 2004, 121,141-240.
DeVs, et al., Biomaterials, 1997, 18, 273.
Hennink, et al., Adv. Drug Deliv. Rev. 2002, 54, 13-36.
Hoffman, Adv. Drug Deliv. Rev. 2002, 54, 3-12.
Jackson, Nat. Med. 1996; 2, 637-638.
Jackson, Am. J. Surg. 2001, 182, 1S-7S.
Jakubowski, Nucleic Acids Res. 1995, 23, 4608-4615.
Jeong, et al., Nature 1997, 388, 860-862.
Johnson, et al., J. Am. Chem. Soc. 2006, 128, 6640-6646.
Kavanagh, et al., Prog. Polym. Sci. 1998, 23, 533-562.
Kemp, Biopolymers 1981, 20, 1793-1804.
Kumar, et al., Adv. Polym. Sci. 2002, 160, 45-117.
Lee, et al., Chem. Rev. 2001, 101, 1869-1879.
Luo, et al., Proc Natl Acad Sci USA. 2007, 104: 2821-2826
Macmillan, Angew. Chem. Int. Edit. 2006, 45, 7668-7672.
Morikawa, Am. J. Surg. 2001, 182, 29S-$^{35}$S.
Okano, Biorelated polymers and gels. Academic Press: Boston, 1998.
O'Shea, Sun Diabetes, 1986, 35, 943.
Peppas, Hydrogels in medicine and pharmacy. CRC Press: Boca Raton, Fla., 1987.
Peppas, et al., Adv. Mater. 2006, 18, 1345-1360.
Rabinovitch, et al., Biochem. Pharmacol, 1998, 55, 1139.
Ross-Murphy, Polymer Gels and Networks 1994, 2, 229-237.
Spotnitz, Am. J. Surg. 2001, 182, 8S-14S.
Sanborn, et al., Biomaterials 2002, 23, 2703-2710.
Sawhney, et al., Macromolecules 1993, 26, 581-587.
Stetsenko, et al., J. Org. Chem. 2000, 65, 4900-4908.
Tam, et al., Biopolymers 2000, 51, 311-332.
Teramura et al., Biomaterials, 2007, 28, 4818.
VanSchilfgaarde, et al., J. Mol. Med., 1999, 77, 199-205.
Wang, Nat. Biotech. 1997, 15, 358-362.
Wathier, et al., J. Am. Chem. Soc. 2004, 126, 12744-12745.
Weber, et al., J. Mol. Evol. 1979, 13, 193-202.
Wiegand, et al., Transplantation, 1993, 56, 1206.
Wieland, Chimia 1974, 28, 496-499.
Wieland, et al., Ann. Chem. 1953, 583, 129-149.

We claim:

1. A macromonomer comprising the structure:

(Formula I)

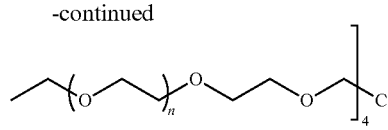

wherein each "n" has a value in the range of from 0 to 200.

2. A method of synthesizing a hydrogel comprising the structure:

-continued

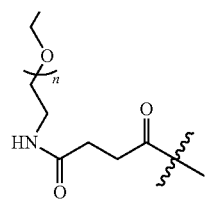

wherein each "n" has a value in the range of from 0 to 200, the method comprising covalently crosslinking through native chemical ligation an effective amount of the macromonomer of claim 1 with an effective amount of a second macromonomer having the structure:

(Formula II)

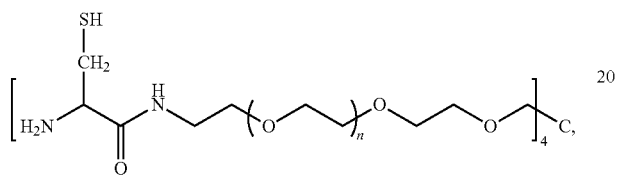

wherein each "n" has a value in the range of 0 to 200; whereby the hydrogel and a thiol byproduct are formed.

3. The method of claim 2 wherein equivalent amounts of the macromonomer of claim 1 and of the second macromonomer are used.

4. A method of synthesizing a biocompatible hydrogel comprising the structure:

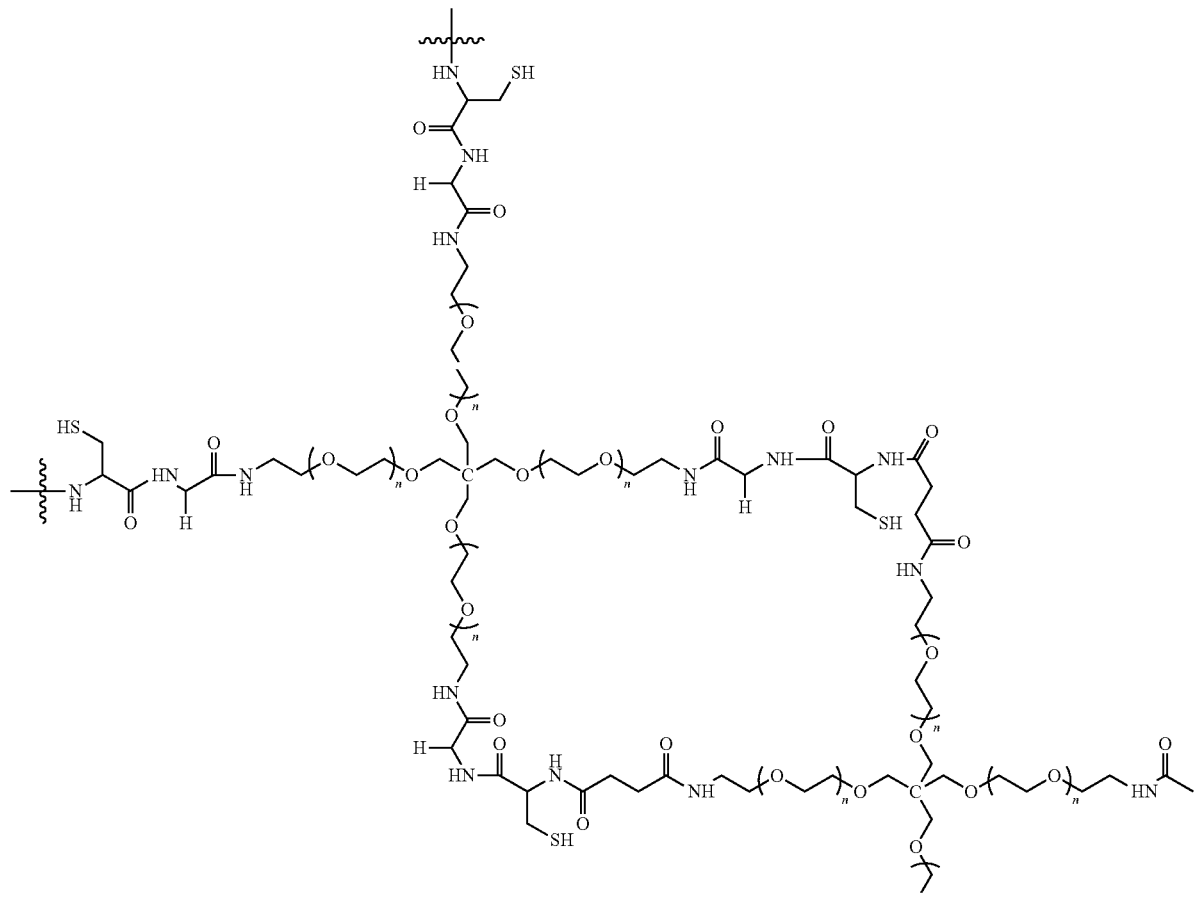

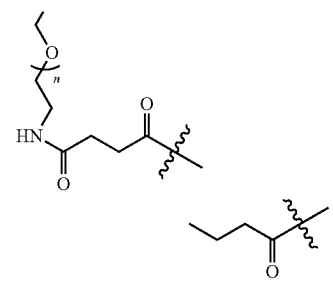

wherein each "n" has a value in the range of from 0 to 200, the method comprising covalently crosslinking through native chemical ligation an effective amount of the macromonomer of claim 1 with an effective amount of a second macromonomer having the structure:

(Formula III)

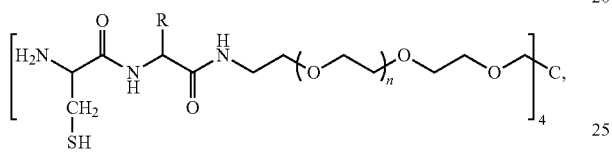

wherein each "n" has a value in the range of 0 to 200 and wherein R is hydrogen;
whereby the biocompatible hydrogel and a thiol byproduct are formed.

5. A method of synthesizing a biocompatible hydrogel comprising the structure:

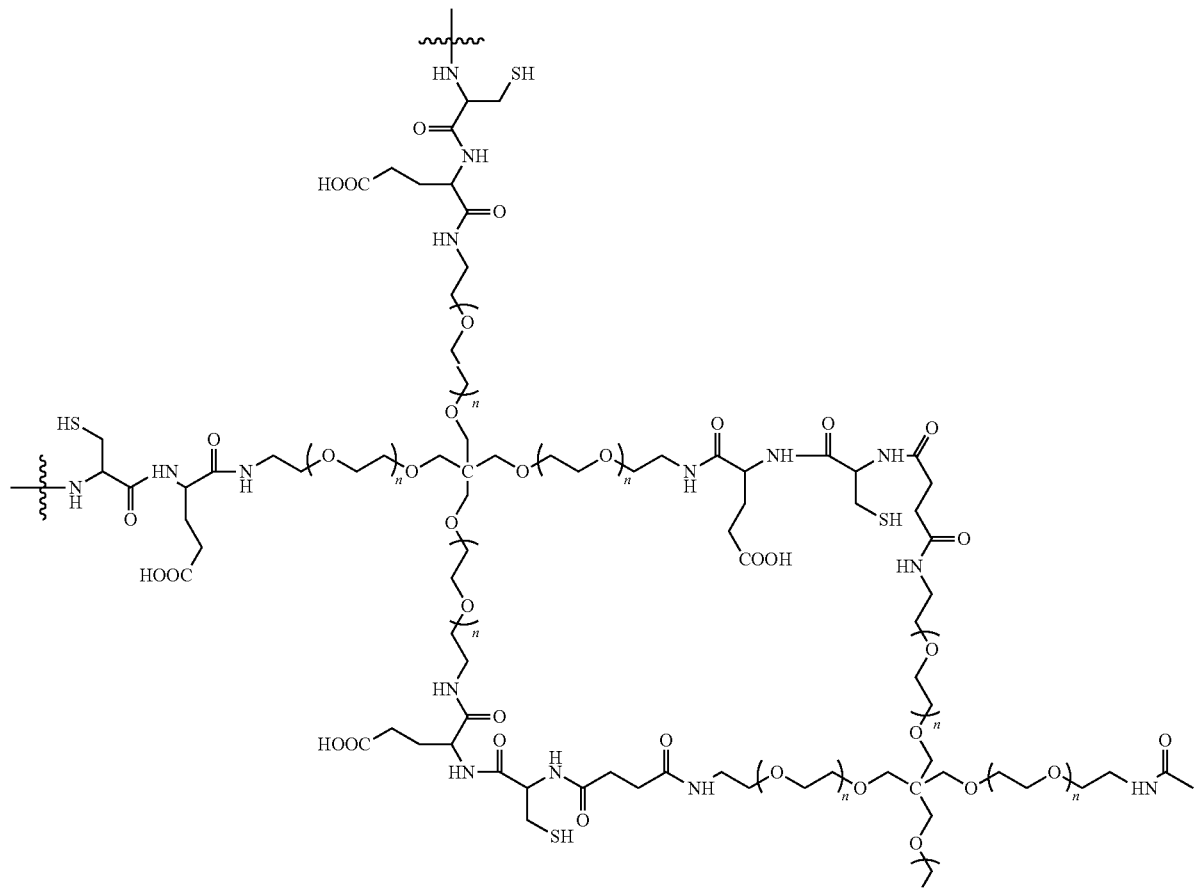

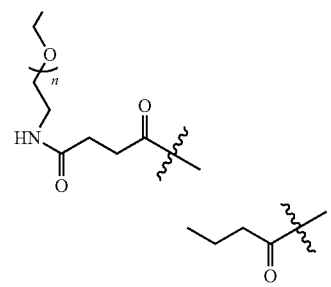

wherein each "n" has a value in the range of from 0 to 200, the method comprising covalently crosslinking through native chemical ligation an effective amount of the macromonomer of claim 1 with an effective amount of a second macromonomer having the structure:

(Formula III)

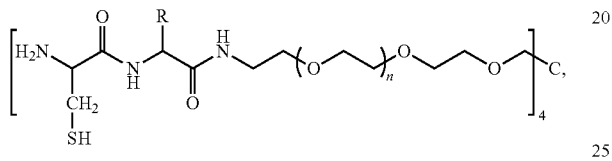

wherein each "n" has a value in the range of 0 to 200 and wherein R is $CH_2CH_7COOH$;

whereby the biocompatible hydrogel and a thiol byproduct are formed.

6. A method of synthesizing a biocompatible hydrogel comprising the structure:

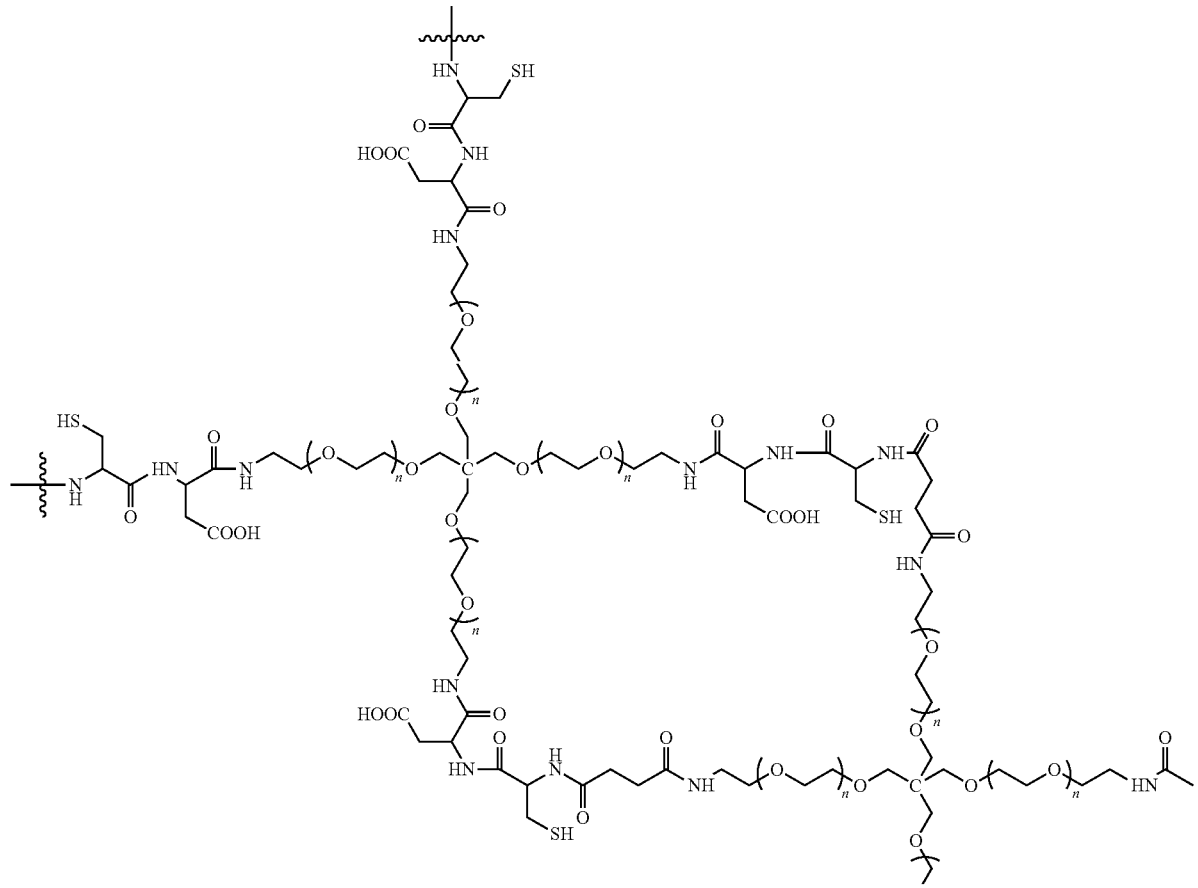

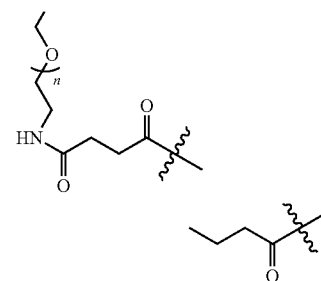

wherein each "n" has a value in the range of from 0 to 200, the method comprising covalently crosslinking through native chemical ligation an effective amount of the macromonomer of claim 1 with an effective amount of a second macromonomer having the structure:

(Formula III)

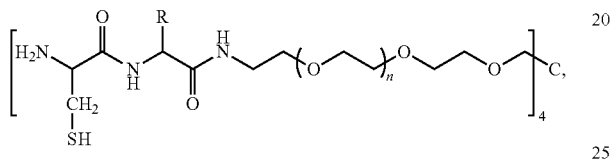

wherein each "n" has a value in the range of 0 to 200 and wherein R is $CH_2COOH$;

whereby the biocompatible hydrogel and a thiol byproduct are formed.

7. A method of synthesizing a biocompatible hydrogel comprising the structure:

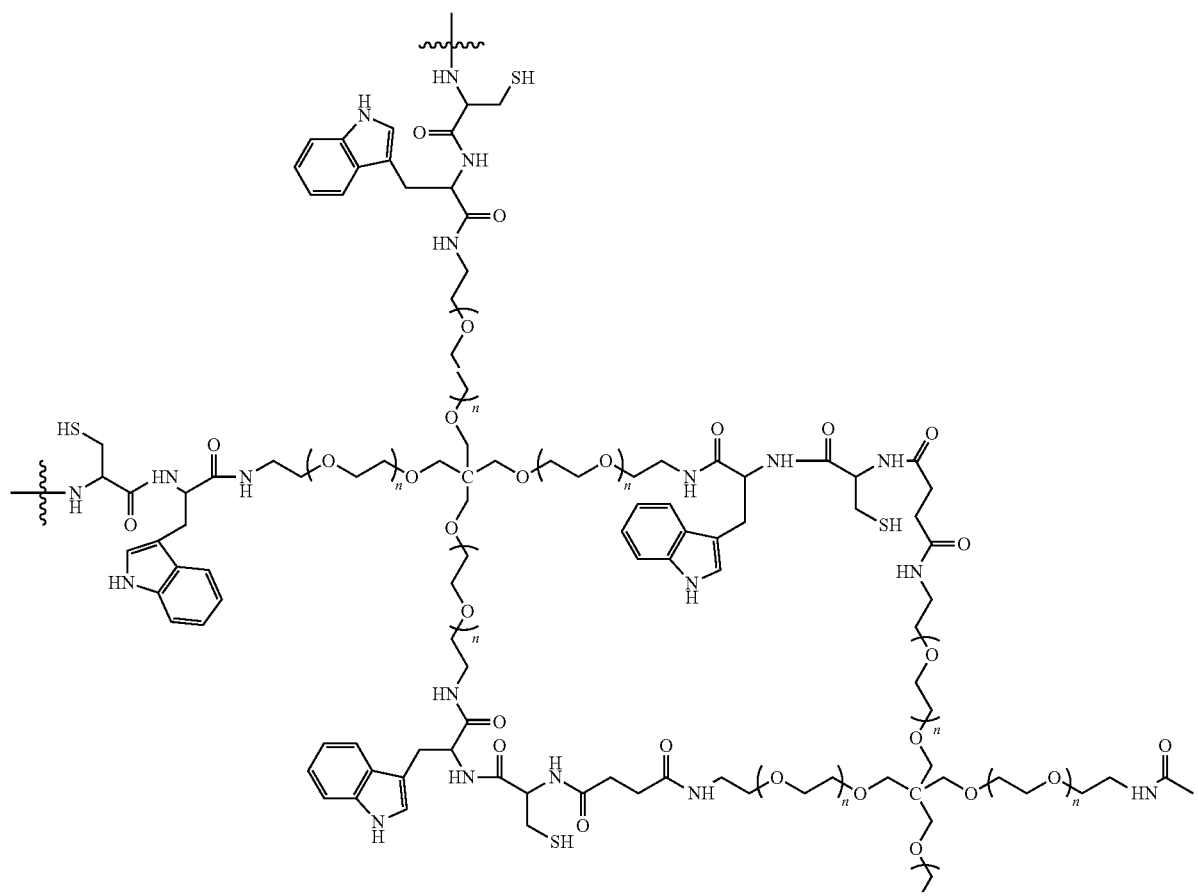

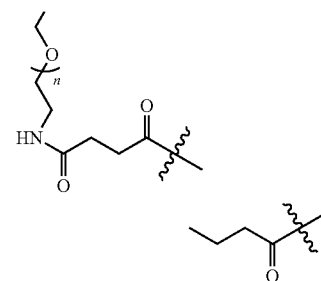

wherein each "n" has a value in the range of from 0 to 200, the method comprising covalently crosslinking through native chemical ligation an effective amount of the macromonomer of claim 1 with an effective amount of a second macromonomer having the structure:

(Formula III)

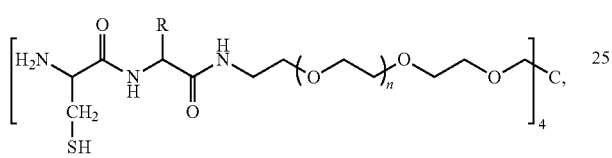

wherein each "n" has a value in the range of 0 to 200 and wherein R is

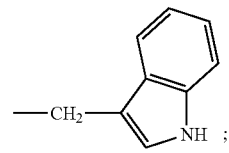

whereby the biocompatible hydrogel and a thiol byproduct are formed.

8. A method of synthesizing a biocompatible hydrogel comprising the structure:

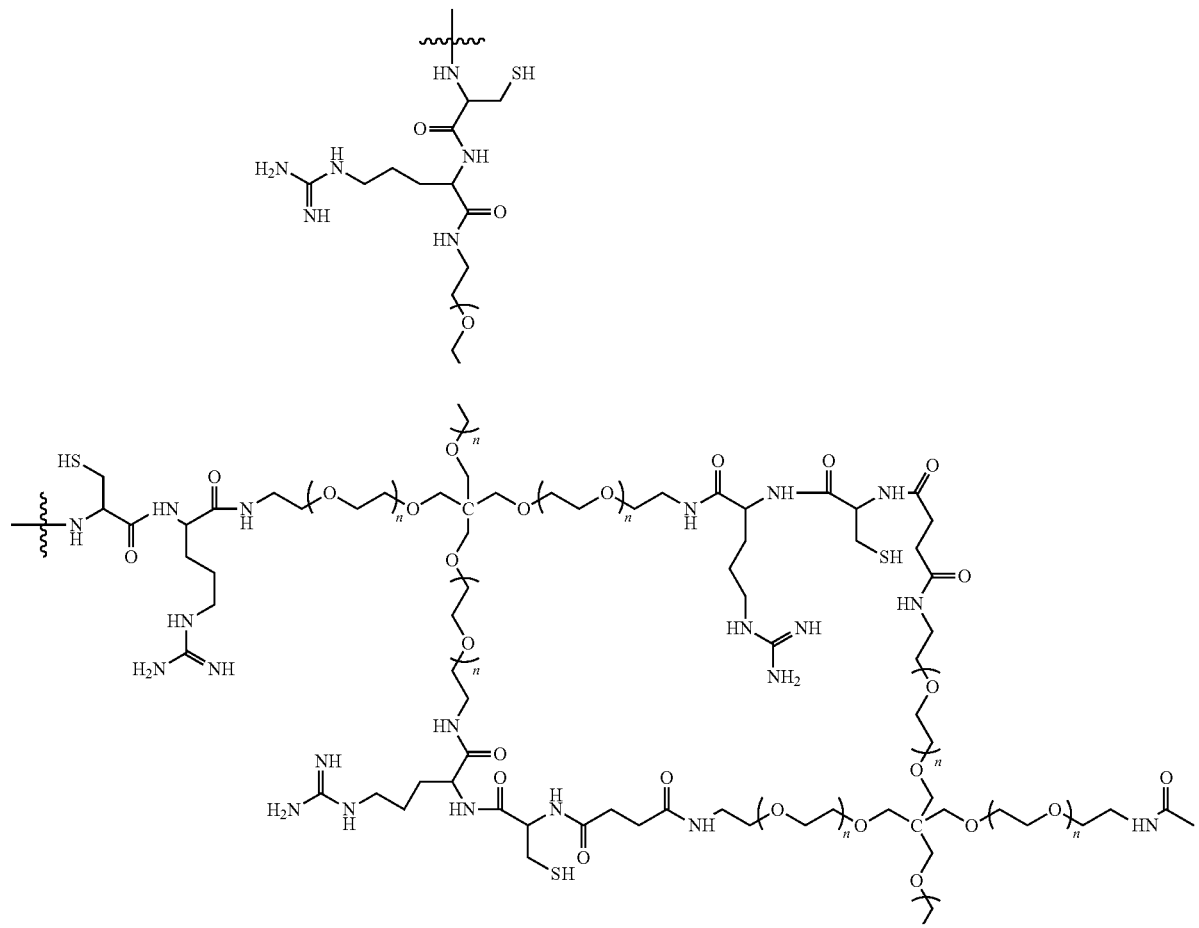

-continued

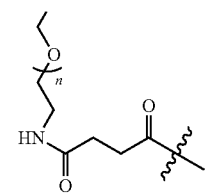

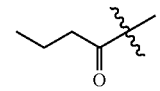

wherein each "n" has a value in the range of from 0 to 200, the method comprising covalently crosslinking through native chemical ligation an effective amount of the macromonomer of claim 1 with an effective amount of a second macromonomer having the structure:

(Formula III)

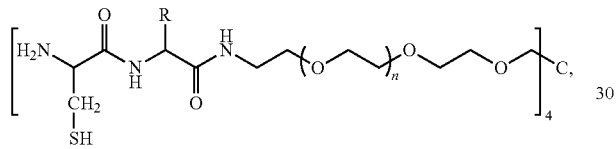

wherein each "n" has a value in the range of 0 to 200 and wherein R is $(CH_2)_3NH(NH)CNH_2$;

whereby the biocompatible hydrogel and a thiol byproduct are formed.

9. A method of synthesizing a macromonomer comprising the structure:

(Formula I)

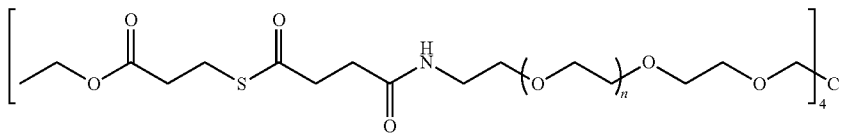

wherein each "n" has a value in the range of from 0 to 200, the method comprising:

(a) preparing a thioester, wherein the thioester is Ethyl 3-Mercaptoproprionate-Succinnic Acid (EMPSA); and (b) coupling the thioester with an amine-terminated 4-armed poly(ethylene glycol); wherein the macromonomer is formed.

10. A hydrogel produced by native chemical ligation of the macromonomer of claim 1 to a macromonomer having the formula:

(Formula II)

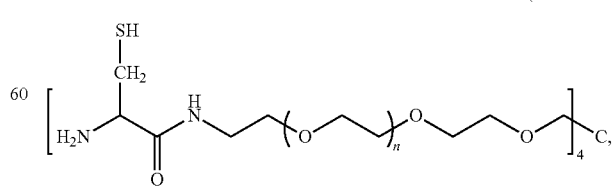

wherein each "n" has a value in the range of 0 to 200;

wherein the hydrogel comprises the following structure:

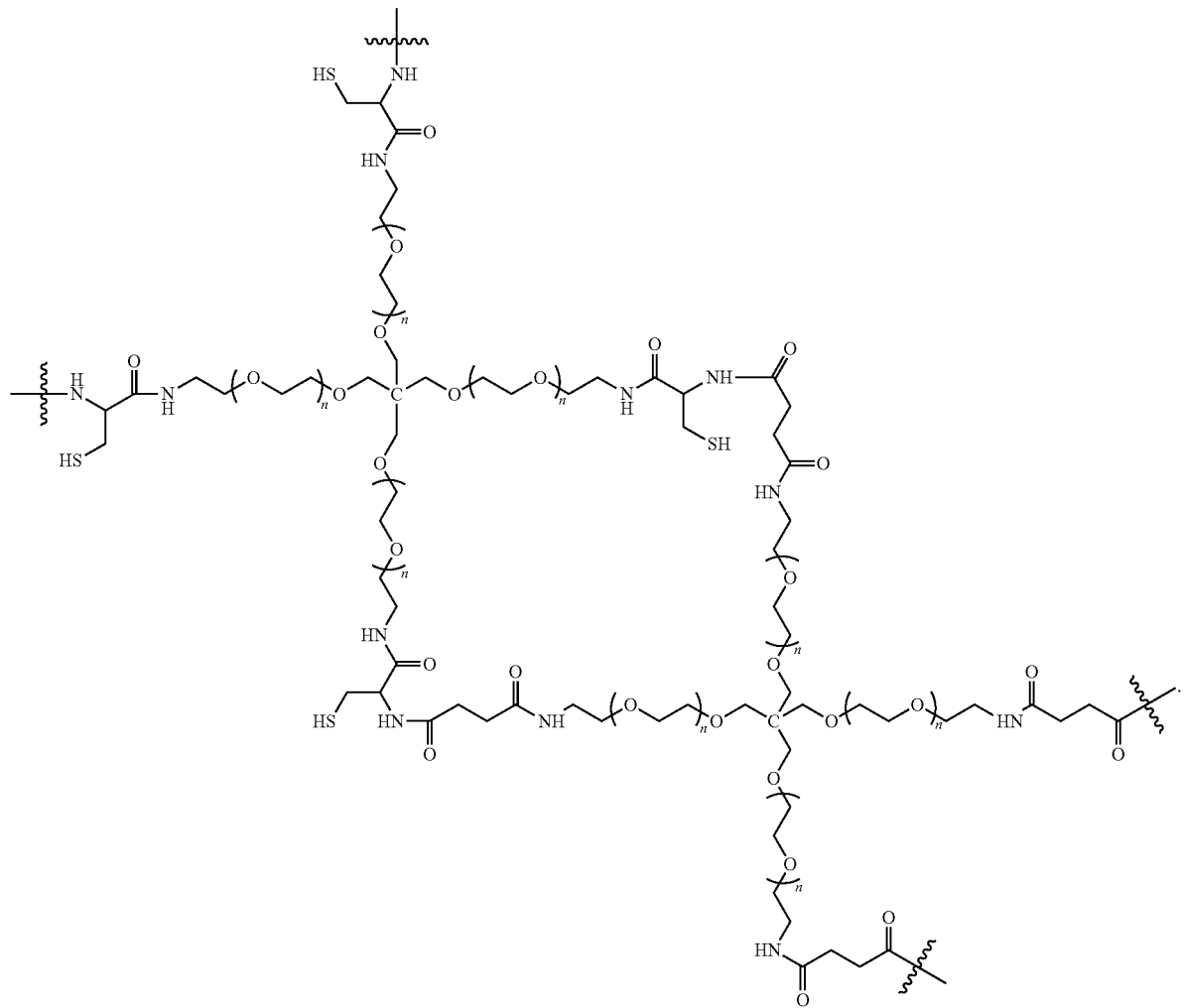
11. A hydrogel produced by native chemical ligation of the macromonomer of claim 1 to a macromonomer having the formula:
(Formula III)
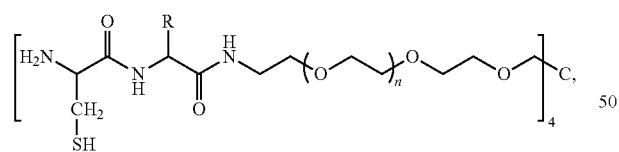
wherein each "n" has a value in the range of 0 to 200 and wherein "R" is selected from the group consisting of H, $CH_2CH_2COOH$, $CH_2COOH$, $(CH_2)_3NH(NH)CNH_2$ and
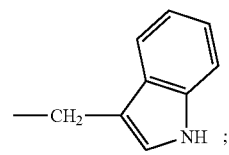
wherein the hydrogel comprises the following structure:
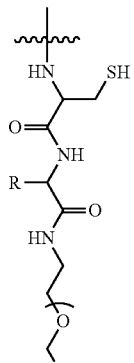

-continued
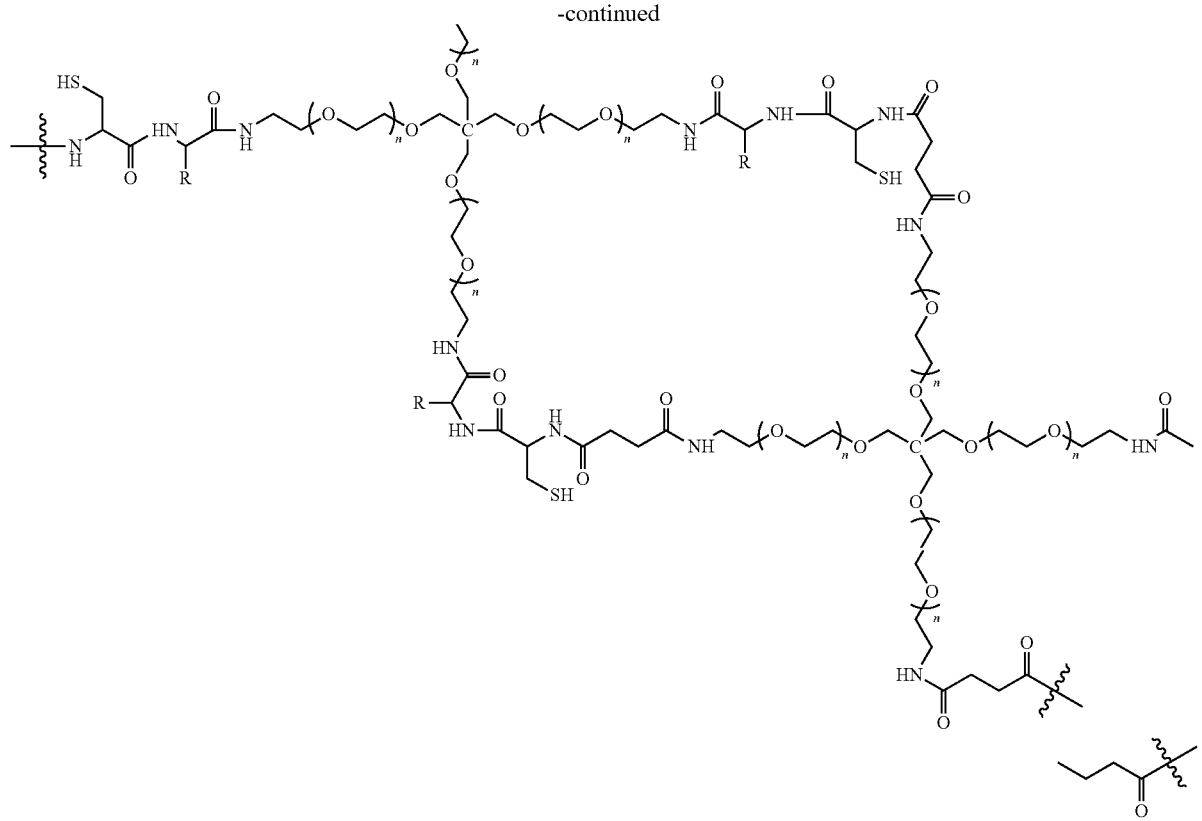
* * * * *